(12) United States Patent
Kaufman et al.

(10) Patent No.: US 8,183,344 B2
(45) Date of Patent: May 22, 2012

(54) INACTIVATION RESISTANT FACTOR VIII

(75) Inventors: Randal J. Kaufman, Ann Arbor, MI (US); Steven W. Pipe, Ypsilanti, MI (US)

(73) Assignee: University of Michigan, Ann Arbor, MI (US)

(*) Notice: Subject to any disclaimer, the term of this patent is extended or adjusted under 35 U.S.C. 154(b) by 0 days.

(21) Appl. No.: 11/455,116

(22) Filed: Jun. 16, 2006

(65) Prior Publication Data

US 2006/0293238 A1 Dec. 28, 2006

Related U.S. Application Data

(63) Continuation of application No. 10/383,206, filed on Mar. 6, 2003, now abandoned, which is a continuation-in-part of application No. 10/283,648, filed on Oct. 29, 2002, now abandoned, application No. 11/455,116, which is a continuation-in-part of application No. 10/974,534, filed on Oct. 26, 2004, now Pat. No. 7,459,534, which is a continuation of application No. 09/819,098, filed on Apr. 11, 2001, now Pat. No. 6,838,437, which is a continuation of application No. 08/980,038, filed on Nov. 26, 1997, now abandoned, which is a continuation-in-part of application No. PCT/US97/06563, filed on Apr. 24, 1997.

(60) Provisional application No. 60/016,117, filed on Apr. 24, 1996, provisional application No. 60/017,785, filed on May 15, 1996.

(51) Int. Cl.
 A61K 38/37 (2006.01)
 C07K 14/755 (2006.01)

(52) U.S. Cl. ........................ 530/383; 514/14.1

(58) Field of Classification Search .................. 435/356
 See application file for complete search history.

(56) References Cited

U.S. PATENT DOCUMENTS

| | | |
|---|---|---|
| 4,399,216 A | 8/1983 | Axel et al. |
| 4,599,308 A | 7/1986 | Hamer et al. |
| 4,745,051 A | 5/1988 | Smith et al. |
| 4,745,057 A | 5/1988 | Beckage et al. |
| 4,757,006 A | 7/1988 | Toole, Jr. et al. |
| 4,761,371 A | 8/1988 | Bell et al. |
| 4,868,112 A | 9/1989 | Toole, Jr. |
| 4,877,729 A | 10/1989 | Clark et al. |
| 4,879,224 A | 11/1989 | Wallner et al. |
| 4,879,236 A | 11/1989 | Smith et al. |
| 4,912,038 A | 3/1990 | Schilling, Jr. et al. |
| 5,004,803 A | 4/1991 | Kaufman et al. |
| 5,045,455 A | 9/1991 | Kuo et al. |
| 5,214,033 A | 5/1993 | Zimmerman et al. |
| 5,250,421 A | 10/1993 | Kaufman et al. |
| 5,422,260 A | 6/1995 | Kaufman et al. |
| 5,451,521 A | 9/1995 | Kaufman et al. |
| 5,563,045 A | 10/1996 | Pittman et al. |
| 5,661,008 A | 8/1997 | Almstedt et al. |
| 5,888,809 A | 3/1999 | Allison |
| 6,171,825 B1 | 1/2001 | Chan et al. |
| 6,683,159 B2 | 1/2004 | Kelley et al. |
| 6,838,437 B2 | 1/2005 | Kaufman et al. |
| 7,041,635 B2 | 5/2006 | Kim et al. |
| 7,459,534 B2 | 12/2008 | Kaufman et al. |
| 2004/0092442 A1 | 5/2004 | Kaufman et al. |
| 2004/0147436 A1 | 7/2004 | Kim et al. |
| 2006/0014683 A1 | 1/2006 | Kaufman et al. |

FOREIGN PATENT DOCUMENTS

| | | |
|---|---|---|
| EP | 295597 | 12/1988 |
| EP | 197901 | 7/1991 |
| EP | 1754718 | 2/2007 |
| WO | WO-86/06101 | 10/1986 |
| WO | WO-87/04187 | 7/1987 |
| WO | WO-87/06101 | 10/1987 |
| WO | WO-87/07144 | 12/1987 |
| WO | WO-88/03558 | 5/1988 |
| WO | WO-88/08035 | 10/1988 |
| WO | WO-91/07490 | 5/1991 |
| WO | WO-97/03194 | 1/1997 |
| WO | WO-97/03195 | 1/1997 |
| WO | WO-97/40145 | 10/1997 |

OTHER PUBLICATIONS

Bertina et al. "Mutation in blood coagulation factor V associated with resistance to activated protein C." Nature. May 5, 1994;369(6475):64-7.
Blond-Elguindi et al. "Affinity panning of a library of peptides displayed on bacteriophages reveals the binding specificity of BiP." Cell. Nov. 19, 1993;75(4):717-28.
Brinkhous et al. "Purified human factor VIII procoagulant protein: comparative hemostatic response after infusions into hemophilic and von Willebrand disease dogs." PNAS USA. Dec. 1985;82(24):8752-6.
Castaman et al. "Effectiveness of high-dose intravenous immunoglobulin in a case of acquired von Willebrand syndrome with chronic melena not responsive to desmopressin and factor VIII concentrate." Am. J. Hematol. Oct. 1992;41(2):132-6.
Cripe et al. "Structure of the gene for human coagulation factor V." Biochemistry. Apr. 21, 1992;31(15):3777-85.

(Continued)

Primary Examiner — Marsha Tsay
(74) Attorney, Agent, or Firm — Foley Hoag LLP

(57) ABSTRACT

The present invention provides novel purified and isolated nucleic acid sequences encoding procoagulant-active FVIII proteins. The nucleic acid sequences of the present invention encode amino acid sequences corresponding to known human FVIII sequences, wherein residue Phe309 is mutated. The nucleic acid sequences of the present invention also encode amino acid sequences corresponding to known human FVIII sequences, wherein the APC cleavage sites, Arg336 and Ile562, are mutated. The nucleic acid sequences of the present invention further encode amino acid sequences corresponding to known human FVIII sequences, wherein the B-domain is deleted, the von Willebrand factor binding site is deleted, a thrombin cleavage site is mutated, an amino acid sequence spacer is inserted between the A2- and A3-domains. Methods of producing the FVIII proteins of the invention, nucleotide sequences encoding such proteins, pharmaceutical compositions containing the nucleotide sequences or proteins, as well as methods of treating patients suffering from hemophilia, are also provided.

5 Claims, 35 Drawing Sheets

OTHER PUBLICATIONS

Dahlback et al. "Familial thrombophilia due to previously unrecognized mechanism characterized by poor anticoagulant response to activated protein C: prediction of a cofactor to activated protein C." PNAS USA Feb. 1, 1993;90(3):1004-8.

Dahlback et al. "Inherited resistance to activated protein C is corrected by anticoagulant cofactor activity found to be a property of factor V." PNAS USA Feb. 15, 1994;91(4):1396-400.

Davie et al. "The coagulation cascade: initiation, maintenance, and regulation." Biochemistry. Oct. 29, 1991;30(43):10363-70.

Dorner et al. "The relationship of N-linked glycosylation and heavy chain-binding protein association with the secretion of glycoproteins." J. Cell Biol. Dec. 1987;105(6 Pt 1):2665-74.

Dorner et al. "Increased synthesis of secreted proteins induces expression of glucose-regulated proteins in butyrate-treated Chinese hamster ovary cells." J. Biol. Chem. 1989;264(34):20602-7.

Dorner et al. "Protein dissociation from GRP78 and secretion are blocked by depletion of cellular ATP levels." PNAS USA Oct. 1990;87(19):7429-32.

Dorner et al. "Overexpression of GRP78 mitigates stress induction of glucose regulated proteins and blocks secretion of selective proteins in Chinese hamster ovary cells." EMBO J. Apr. 1992,11(4):1563-71.

Eaton et al. "Proteolytic processing of human factor VIII. Correlation of specific cleavages by thrombin, factor Xa, and activated protein C with activation and inactivation of factor VIII coagulant activity." Biochemistry. Jan. 28, 1986;25(2):505-12.

Fay et al. "von Willebrand factor mediates protection of factor VIII from activated protein C-catalyzed inactivation." J. Biol. Chem. Feb. 5, 1991;266(4):2172-7.

Fay et al. "Human factor VIIIa subunit structure. Reconstruction of factor VIIIa from the isolated A1/A3-C1-C2 dimer and A2 subunit." J. Biol. Chem. May 15, 1991;266(14):8957-62.

Fay et al. "Activated protein C-catalyzed inactivation of human factor VIII and factor VIIIa. Identification of cleavage sites and correlation of proteolysis with cofactor activity." J. Biol. Chem. Oct. 25, 1991;266(30):20139-45.

Fay et al. "Role of COOH-terminal acidic region of A1 subunit and in A2 subunit retention in human factor VIIIa." J. Biol. Chem. Aug. 25, 1993;268(24):17861-6.

Fay et al. "Factor VIIIa A2 subunit residues 558-585 represent a factor IXa interactive site." J. Biol. Chem. Aug. 12, 1994;269(32):20522-7.

Flynn et al. "Peptide binding and release by proteins implicated as catalysts of protein assembly." Science Jul. 28, 1989;245(4916):385-90.

Fulcher et al. "Proteolytic inactivation of human factor VIII procoagulant protein by activated human protein C and its analogy with factor V." Blood Feb. 1984;63(2):486-9.

Gitschler et al. "Characterization of the human factor VIII gene." Nature Nov. 22-28, 1984;312(5992):326-30.

Guinto et al. "The complete cDNA sequence of bovine coagulation factor V." J. Biol. Chem. Feb. 15, 1992;267(5):2971-8.

Healey et al. "Residues Glu2181-Val2243 Contain a Major Determinant of the Inhibitory Epitope in the C2 Domain of Human Factor VIII," Blood, 1998, 92(10):3701-9.

Jenny et al. "Complete cDNA and derived amino acid sequence of human factor V." PNAS USA Jul. 1987;84(14):4846-50.

Kane et al. "Cloning of a cDNA coding for human factor V, a blood coagulation factor homologous to factor VIII and ceruloplasmin." PNAS USA Sep. 1986;83(16):6800-4.

Kaufman et al. "Amplification and expression of sequences cotransfected with a modular dihydrofolate reductase complementary DNA gene." J. Mol. Biol. Aug. 25, 1982;159(4):601-21.

Kaufman et al. "Identification of the components necessary for adenovirus translational control and their utilization in cDNA expression vectors." PNAS USA Feb. 1985;82(3):689-93.

Kaufman et al. "Synthesis, processing, and secretion of recombinant human factor VIII expressed in mammalian cells." J. Biol. Chem. May 5, 1988;263(13):6352-62.

Kozutsumi et al. "The presence of malfolded proteins in the endoplasmic reticulum signals the induction of glucose-regulated proteins." Nature Mar. 31, 1988;332(6163):462-4.

Koedam et al. "Inactivation of human factor VIII by activated protein C. Cofactor activity of protein S and protective effect on von Willebrand factor." J. Clin. Invest. Oct. 1988;82(4):1236-43.

Lenting et al. "Identification of a binding site for blood coagulation factor IXa on the light chain of human factor VIII." J. Biol. Chem. Mar. 11, 1994;269(10):7150-5.

Leyte et al. "Sulfation of Tyr1680 of human blood coagulation factor VIII is essential for the interaction of factor VIII with von Willebrand factor." J. Biol. Chem. Jan. 15, 1991;266(2):740-6.

Lollar et al. "Structural basis for the decreased procoagulant activity of human factor VIII compared to the porcine homolog." J. Biol. Chem. Jul. 5, 1991;266(19):12481-6.

Lusky et al. "Characterization of the bovine papilloma virus plasmid maintenance sequences." Cell. Feb. 1984;36(2):391-401.

Mann et al. "Cofactor proteins in the assembly and expression of blood clotting enzyme complexes." Annu. Rev. Biochem. 1988;57:915-56.

Marquette et al. "A 110-amino acid region within the A1-domain of coagulation factor VIII inhibits secretion from mammalian cells." J. Biol. Chem. Apr. 28, 1995;270(17):10297-303.

Michnick et al. "Identification of individual tyrosine sulfation sites within factor VIII required for optimal activity and efficient thrombin cleavage." J. Biol. Chem. Aug. 5, 1994;269(31):20095-102.

Munro et al. "An Hsp70-like protein in the ER: identity with the 78 kd glucose-regulated protein and immunoglobulin heavy chain binding protein." Cell. Jul. 18, 1986;46(2):291-300.

Nesheim et al. "The effect of plasma von Willebrand factor on the binding of human factor VIII to thrombin-activated human platelets." J. Biol. Chem. Sep. 25, 1991;266(27):17815-20.

Ortel et al. "Structural model of human ceruloplasmin based on internal triplication, hydrophilic/hydrophobic character, and secondary structure of domains." PNAS USA Aug. 1984;81(15):4761-5.

Pipe et al., "Construction and characterization of inactivation resistant factor VIII," Blood, 88(10):441 (1996).

Pipe et al., "Characterization of a genetically engineered inactivation-resistant coagulation factor VIIIa." PNAS USA. Oct. 28, 1997;94(22):11851-6.

Pittman et al., "Proteolytic requirements for thrombin activation of anti-hemophilic factor (factor VIII)." Proc. Nat. Acad. Sc. 85:2429-33 (1988).

Pittman et al. "A2 domain of human recombinant-derived factor VIII is required for procoagulant activity but not for thrombin cleavage." Blood. Jan. 15, 1992;79(2):389-97.

Pittman et al. "Post-translational requirements for functional factor V and factor VIII secretion in mammalian cells." J. Biol. Chem. Jun. 24, 1994;269(25):17329-37.

Pittman et al. "Role of the B domain for factor VIII and factor V expression and function." Blood. Dec. 15, 1994;84(12):4214-25.

Saenko et al. "A novel mechanism for inhibition of factor VIII activity by an antibody with a C2 domain epitope, residues 2248-2285." Blood 1995;86 Abstr. 749.

Scandella et al. "Some factor VIII inhibitor antibodies recognize a common epitope corresponding to C2 domain amino acids 2248 thorough 2312, which overlap a phospholipid-binding site." Blood. Sep. 1, 1995;86(5):1811-9.

Shima et al. "Common inhibitory effects of human anti-C2 domain inhibitor alloantibodies on factor VIII binding to von Willebrand factor." Blood. 1995;86 Abstr. 748.

Shima et al. "Common inhibitory effects of human anti-C2 domain inhibitor alloantibodies on factor VIII binding to von Willebrand factor." Br. J. Haematol. Nov. 1995;91(3):714-21.

Stubbs et al. "cDNA cloning of a mouse mammary epithelial cell surface protein reveals the existence of epidermal growth factor-like domains linked to factor VIII-like sequences." PNAS USA Nov. 1990;87(21):8417-21.

Sun et al. "Blood coagulation factor Va abnormality associated with resistance to activated protein C in venous thrombophilia." Blood. Jun. 1, 1994;83(11):3120-5.

Svensson et al. "Resistance to activated protein C as a basis for venous thrombosis." N. Engl. J. Med. Feb. 24, 1994;330(8):517-22.

Swaroop, M. et al., "Mutation of Phe309Ser, a putative BIP binding site, enhances secretion of coagulation factor VIII," Blood, 88(10):441a (1996).

Takahashi et al, "Single-chain structure of human ceruloplasmin: the complete amino acid sequence of the whole molecule." PNAS USA. Jan. 1984; 81(2):390-4.

Toole et al. "Molecular cloning of a cDNA encoding human antihaemophilic factor." Nature. Nov. 22-28, 1984;312(5992):342-7.

Toole et al. "A large region (approximately equal to 95 kDa) of human factor VIII is dispensable for in vitro procoagulant activity." PNAS USA Aug. 1986;83(16):5939-42.

Toole, J. J. et al., "Exploration of structure-function relationships in human factor VIII by site-directed mutagenesis." Cold Spring Harbor Symposia on Quantitative Biology, 51(1):543-9 (1986).

Varadi et al. "Influence of factor V and factor Va on APC-induced cleavage of human factor VIII." Thromb. Haemost. Apr. 1995;73(4):730-1.

Varadi et al. "A chromogenic assay for activated protein C resistance." Br. J. Haematol. Aug. 1995;90(4):884-91.

Vehar et al. "Structure of human factor VIII." Nature. Nov. 22-28, 1984;312(5992):337-42.

Walker et al. "Inactivation of factor VIII by activated protein C and protein S." Arch. Biochem. Biophys. Jan. 1987;252(1):322-8.

Walker et al. "Identification of the binding site for activated protein C on the light chain of factors V and VIII." J. Biol. Chem. Jan. 25, 1990;265(3):1484-9.

Wood et al. "Expression of active human factor VIII from recombinant DNA clones." Nature. Nov. 22-28, 1984;312(5992):330-7.

Fay, Philip J., et al., "Model for the Factor VIIIa-dependent Decay of the Intrinsic Factor Xase," The Journal of Biological Chemistry, 271(11): 6027-6032 (Mar. 15, 1996).

Lee, Amy S., "Mammalian stress response: induction of the gluclose-regulated protein family," Cell Biology, 4:267-273 (1992).

Miao, Hongzhi Z., et al.; "Bioengineering of coagulation factor VIII for improved secretion," Blood, 103(9):3412-3419 (May 1, 2004).

Pittman, Debra D., et al.; "[14] Site-Directed Mutagenesis and Expression of Coagulation Factors VIII and V in Mammalian Cells," Methods in Enzymology, 222:236-260 (1993).

Running Deer, Jennifer, et al.; "High-Level Expression of Proteins in Mammalian Cells Using Transcription Regulatory Sequences from the Chinese Hamster EF-1α Gene," Biotechnology Progress, 20(3):880-889 (May 2004).

Shima, M., et al.; "An Arginine to Cysteine Amino Acid Substitution at a Critical Thrombin Cleavage Site in a Dysfunctional Factor VIII Molecule," Blood 74(5): 1612-1617 (Oct. 1989).

Wells, James A., "Additivity of Mutational Effects in Proteins," Biochemistry, 29(37):8509-8517 (Sep. 18, 1990).

Examiners Report for Australian Application No. 2007269233 mailed Mar. 19, 2010.

EP Search Report for EP10157809 dated May 21, 2010.

Partial EP Search Report for EP06004484 dated Jan. 9, 2007.

International Search Report for PCT/US07/72506 mailed Aug. 8, 2008.

Office Action for U.S. Appl. No. 12/252,024 dated Jan. 25, 2010.

Office Action for U.S. Appl. No. 12/758,457 dated Feb. 18, 2011.

Amano, Kagehiro, et al. "Mutation at either Arg336 or Arg562 in Factor VIII Is Insufficient for Complete Resistance to Activated Protein C (APC)—mediated Inactivation: Implications for the APC Resistance Test," Thromb Haemost, 79:557-63 (1998).

Newell, Jennifer L., et al. "Proteolysis at Arg[740] Facilitates Subsequent Bond Cleavages during Thrombin-catalyzed Activation of Factor VIII," The Journal of Biological Chemistry, 282(35):25367-375, (Aug. 31, 2007).

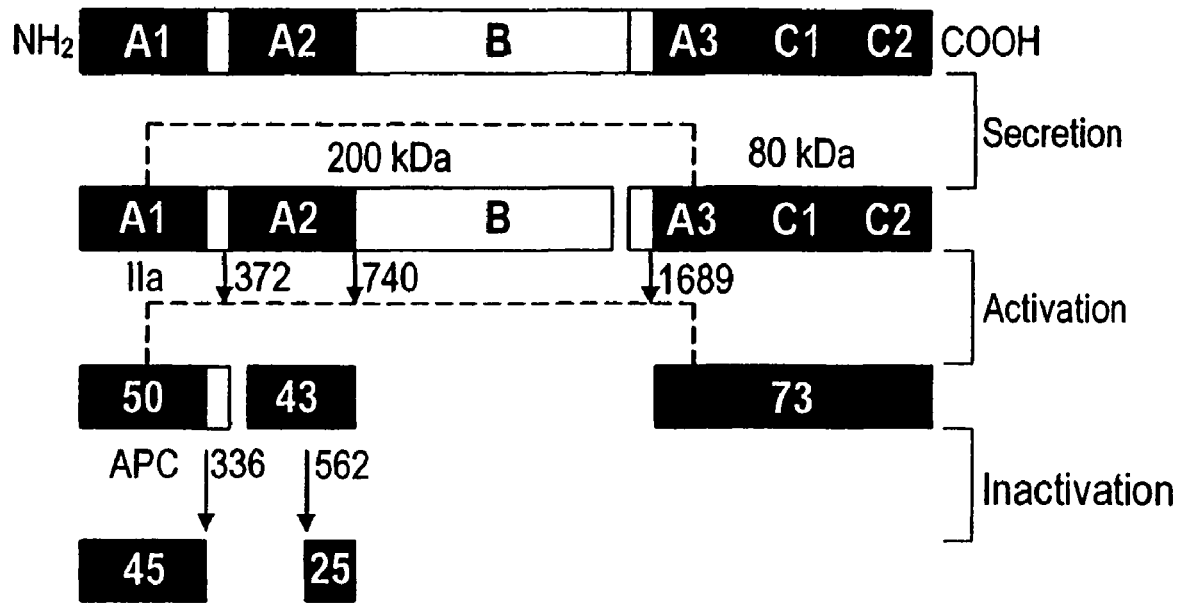
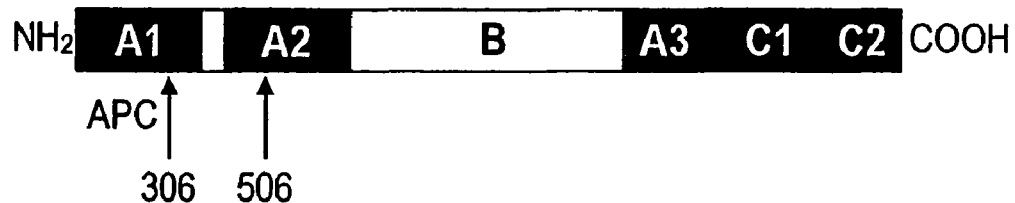
Fig. 1A

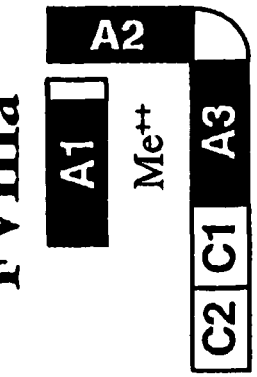
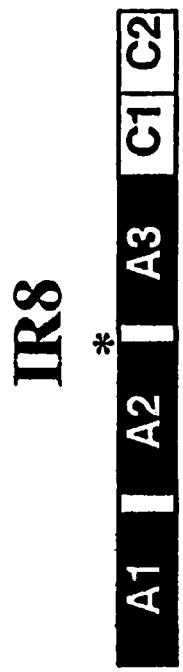
Fig. 1B

Activity in conditioned medium from transiently transfected COS-1 cells (compared to wild-type).

| Residue | FVIII Sequence<br>ITFLTAQTLLMDLGQFL LFCHISS<br>291                            314 | FVIII Activity |
|---|---|---|
| 7(F,L-A) | AA    A    AA AA | Not Detected |
| F293S | S | No Effect |
| F306W | W | No Effect |
| F306/309W,S | W   S | 1.6x ↑ |
| L,F308/309E,S | ES | 1.9x ↑ |
| Q,F305/309K,S | K    S | 2.0x ↑ |
| F309S | S | 1.9x ↑ |

Fig. 2

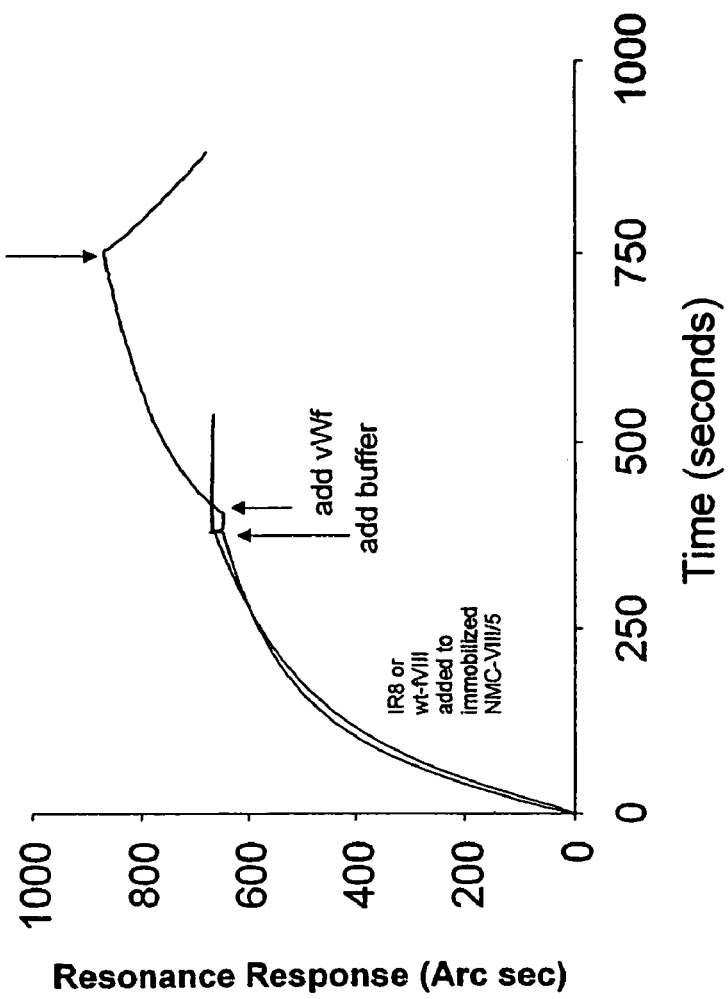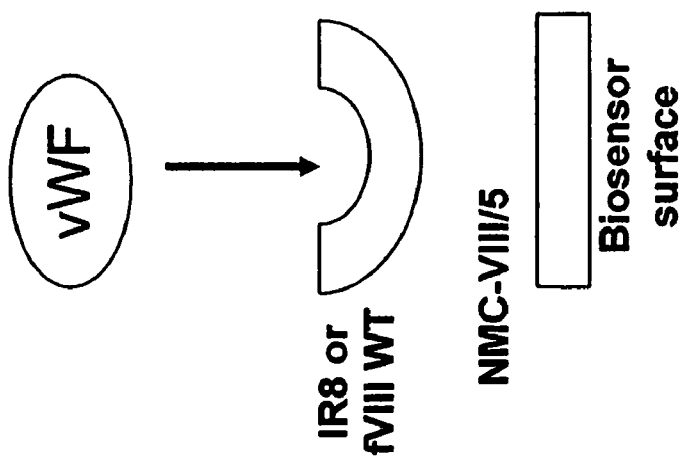
Fig. 23

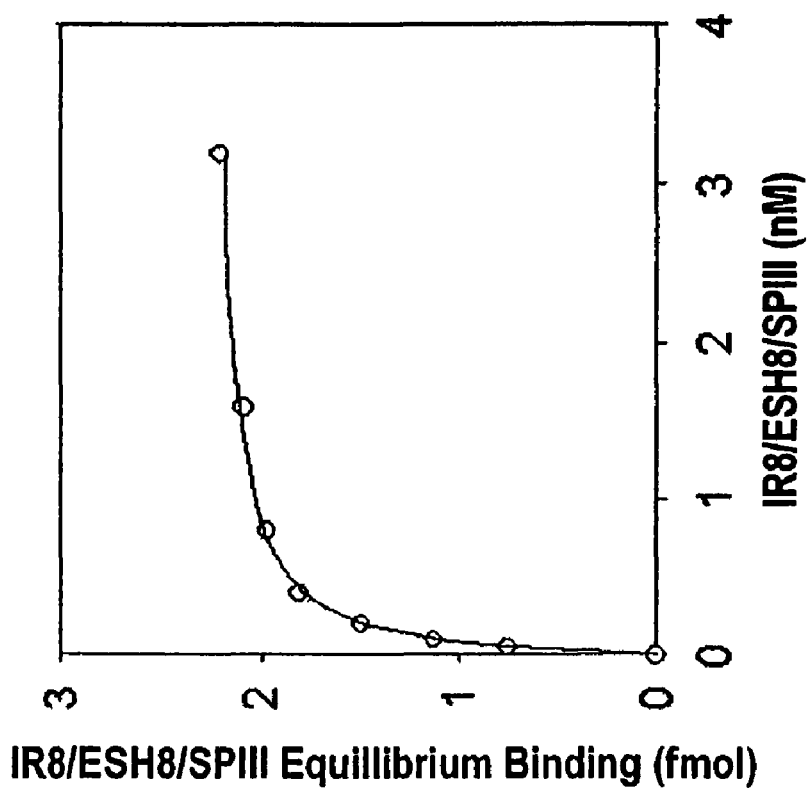
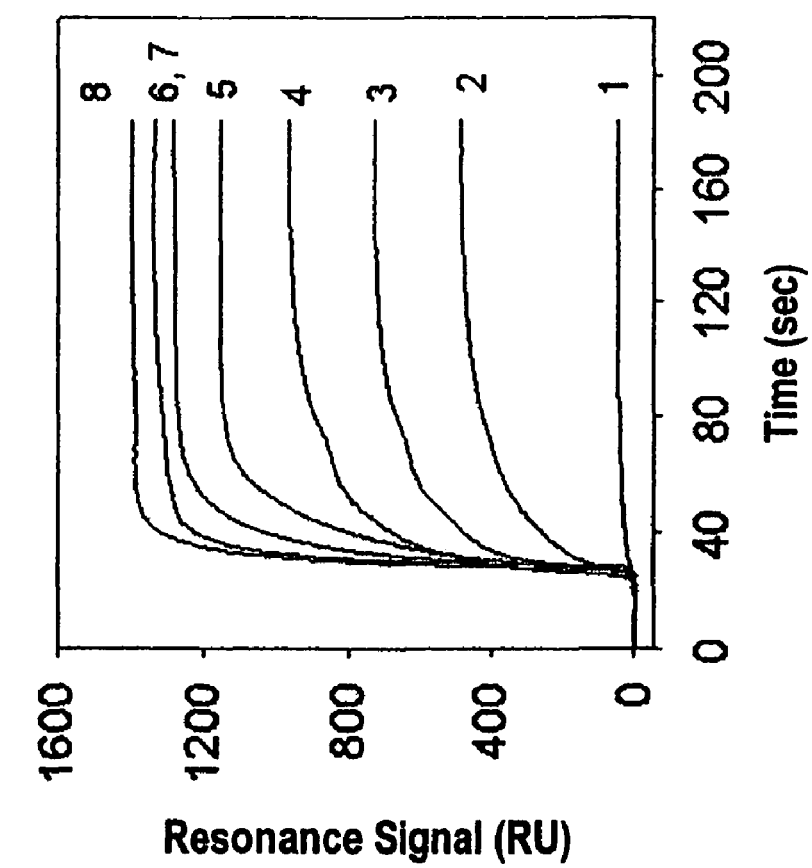
Fig. 25B
Fig. 25A

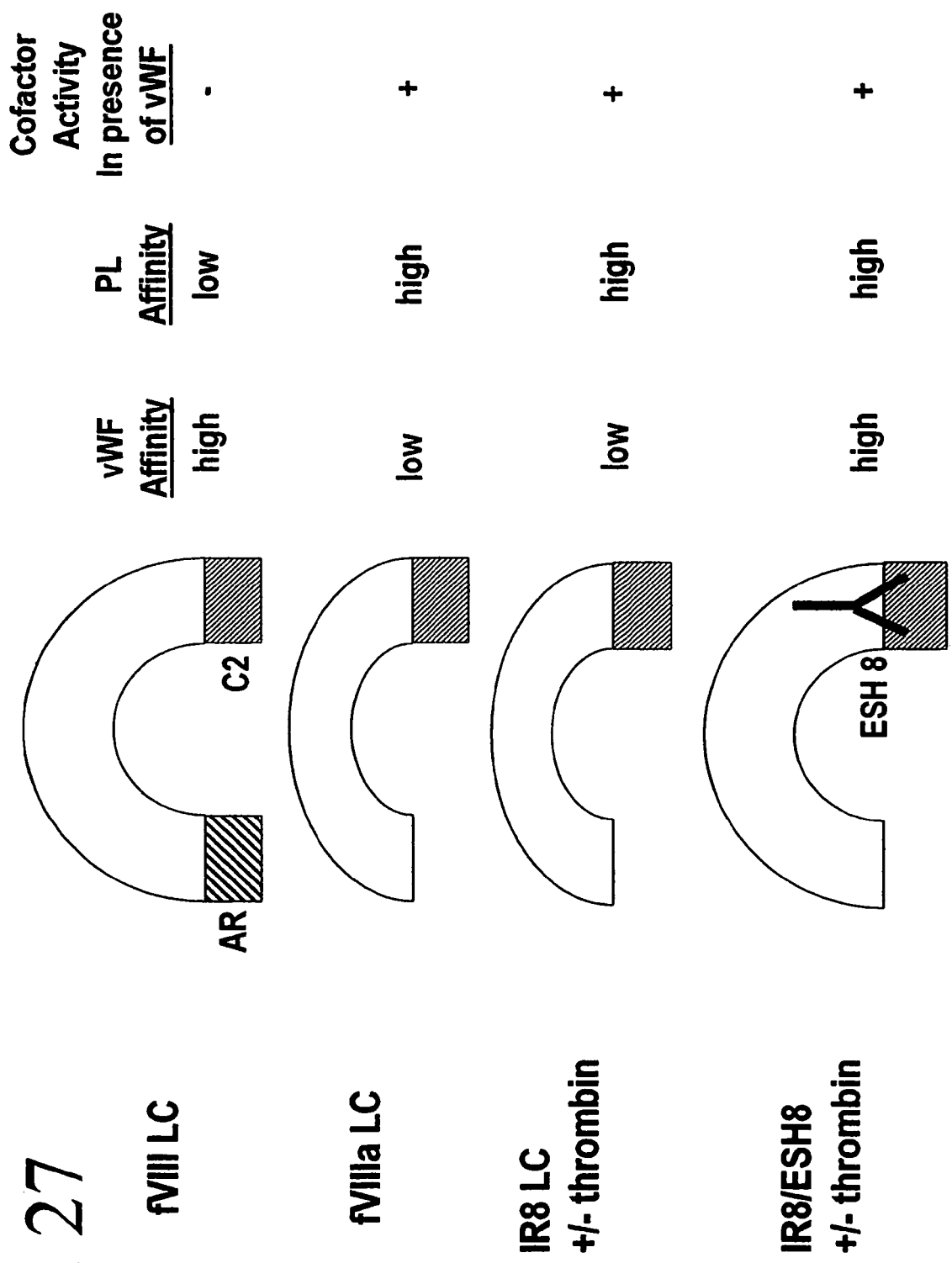

Average BDD-FVIII expression:   24 hr - 123 ng/ml
48 hr - 124 ng/ml

INACTIVATION RESISTANT FACTOR VIII

RELATED APPLICATIONS

This application is a continuation of U.S. patent application Ser. No. 10/383,206, filed Mar. 6, 2003, which is a continuation-in-part application of U.S. patent application Ser. No. 10/283,648, filed Oct. 29, 2002, both of which are expressly incorporated herein by reference. This application is also a continuation-in-part application of U.S. patent application Ser. No. 10/974,534, filed Oct. 26, 2004, which is a continuation of U.S. patent application Ser. No. 09/819,098, filed Apr. 11, 2001, which is a continuation of U.S. patent application Ser. No. 08/980,038, filed on Nov. 26, 1997, which claims priority under 35 U.S.C. §120 from PCT International Application No. PCT/US97/06563, filed Apr. 24, 1997, which claims priority to U.S. Ser. No. 60/016,117, filed Apr. 24, 1996 and U.S. Ser. No. 60/017,785, filed May 15, 1996, all of which are expressly incorporated herein by reference.

SPONSORSHIP

This invention was made with government support under HL057346, HL 053777, and HL052173 awarded by the National Institutes of Health. The government has certain rights in the invention.

FIELD OF THE INVENTION

The present invention relates generally to procoagulant-active proteins and more particularly, nucleotide sequences encoding factor VIII protein capable of secretion at levels higher than typically obtained with wild-type factor VIII, APC resistant factor VIII protein and inactivation resistant factor VIII protein.

BACKGROUND OF THE INVENTION

Human factor VIII:C (FVIII) is the coagulation factor deficient in the X-chromosome-linked bleeding disorder hemophilia A, a major source of hemorrhagic morbidity and mortality in affected males. Traditionally, hemophiliacs were treated with transfusions of whole blood. More recently, treatment has been with preparations of FVIII concentrates derived from human plasma. However, the use of plasma-derived product exposes hemophiliac patients to the possible risk of virus-transmissible diseases such as hepatitis and AIDS. Costly purification schemes to reduce this risk increases treatment costs. With increases in costs and limited availability of plasma-derived FVIII, patients are treated episodically on a demand basis rather than prophylactically. Recombinantly produced FVIII has substantial advantages over plasma-derived FVIII in terms of purity and safety, as well as increased availability and accordingly, much research effort has been directed towards the development of recombinantly produced FVIII.

Due to the labile nature of FVIII, especially following its activation, large and repeated doses of protein whether plasma or recombinantly-derived, must be administered to achieve a therapeutic benefit. However, the amount of FVIII protein the patient is exposed to has been correlated with the development of antibodies which inhibit its activity. In light of this known immunogenicity, one of the goals in developing new recombinant forms of FVIII for use as a therapeutic agent is the development of products that reduce or eliminate such an immune response.

FVIII functions in the intrinsic pathway of blood coagulation as a cofactor to accelerate the activation of factor X by factor IXa, a reaction that occurs on a negatively charged phospholipid surface in the presence of calcium ions. FVIII is synthesized as a 2351 amino acid single-chain polypeptide having the domain structure A1-A2-B-A3-C1-C2. Wehar, G. A. et al., *Nature* 312:337-342 (1984) and Toole, J. J. et al., *Nature* 312:342-347 (1984). The domain structure of FVIII is identical to that of the homologous coagulation factor, factor V (FV). Kane, W. H. et al., *PNAS (USA)* 83:6800-6804 (1986) and Jenny, R. J. et al., *PNAS (USA)* 84:4846-4850 (1987). The FVIII A-domains are 330 amino acids and have 40% amino acid identity with each other and to the A-domain of FV and the plasma copper-binding protein ceruloplasmin. Takahashi, N. et al., *PNAS (USA)* 81:390-394 (1984). Each C-domain is 150 amino acids and exhibits 40% identity to the C-domains of FV, and to proteins that bind glycoconjugates and negatively charged phospholipids. Stubbs, J. D. et al., *PNAS (USA)* 87:8417-8421 (1990). The FVIII B-domain is encoded by a single exon and exhibits little homology to any known protein including FV B-domain. Gitschier, J. et al., *Nature* 312:326-330 (1984) and Cripe, L. D. et al., *Biochemistry* 31:3777-3785 (1992).

FVIII is secreted into plasma as a heterodimer of a heavy chain (domains A1-A2-B) and a light chain (domains A3-C1-C2) associated through a noncovalent divalent metal ion linkage between the A1- and A3-domains. In plasma, FVIII is stabilized by binding to von Willebrand factor (vWF). More specifically, the FVIII light chain is bound by noncovalent interactions to a primary binding site in the amino terminus of von Willebrand factor. FVIII binds to phospholipid (PL) membranes, to vWF and to factor IXa via motifs localized to the C2 domain. Binding of FVIII to von Willebrand factor is mediated by epitopes within the terminal C2 domain as well as a contribution from the N-terminal acidic region (AR). PL binding is mediated by the terminal C2 domain. Previous work has demonstrated that the PL and vWF binding sites are overlapping and are competitive. Foster, P. A. et al., *Blood*, 75(10):1999-2004 (1990); Saenko, E. L. et al., *J. Biol. Chem.*, 269(15):11601-5 (1994); and Healey, J. F. et al., *Blood*, 92(10):3701-9 (1998).

It has also been shown that PL binding and vWF binding are mediated by two pairs of hydrophobic residues, each displayed at the tips of β-hairpin turns. Pratt, K. P. et al., *Nature*, 402(6760):439-42 (1999) and Barrow, R. T. et al., *Blood*, 97(1):169-74 (2001). The homologous hydrophobic residues in the C2 domain of factor V also contribute to PL binding. It is believed that the solvent-exposed hydrophobic residues of the FVIII C2 make specific contacts with both PL and factor IXa, rather than merely providing hydrophobic surface area.

Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa), also known as thrombin-activated factor VIII, thus consists of an A1-subunit associated through the divalent metal ion linkage to a thrombin-cleaved A3-C1-C2 light chain and a free A2 subunit associated with the A1 domain through an ion association (see FIG. 1A). Eaton, D. et al., *Biochemistry* 25: 505 (1986); Lollar, P. et al., *J. Biol. Chem.* 266: 12481 (1991); and Fay, P. J. et al., *J. Biol. Chem.* 266: 8957 (1991).

This FVIIIa heterotrimer is unstable and subject to rapid inactivation through dissociation of the A2 subunit under physiological conditions. A homology model (Pemberton, S. et al., *Blood* 89(7):2413-21 (1997)) of the triplicated A domains of FVIII predicts a pseudo-threefold axis at the tightly packed hydrophobic core with several interdomain interactions. These lie at the interface of A1-A2, A2-A3 and A1-A3. Hemophilia A mutations (R531H, A284E, S289L) within the predicted A1-A2 interface disrupt potential inter-subunit hydrogen bonds and have the molecular phenotype of increased rate of inactivation of FVIIIa due to increased rate of A2 subunit dissociation. Patients with these mutations exhibit a clinical phenotype here the FVIII activity by one-stage (1-st) assay is at least two-fold higher than by two-stage (2-st) assay.

FVa and FVIIIa are inactivated by Activated protein C (APC) in the presence of phospholipid and $CaCl_2$ and APC-resistance has been considered to be one of the major causes of hereditary thrombophilia. Dahlbäck, B. et al., *PNAS (USA)* 90: 1004 (1993). The molecular basis for the APC-resistance was attributed to resistance to PC cleavage and inactivation. Dahlbäck, B. et al., *PNAS (USA)* 91: 1396 (1994). Previous studies on the APC inactivation of FVIII noted the generation of a 45 kDa fragment (Fulcher, C. A. et al., *Blood* 63: 486 (1984)) derived from the amino-terminus of the heavy chain and was proposed to result from cleavage at Arg336. Eaton, D. et al., *Biochemistry* 25: 505 (1986). While the light chain of FVIII is not cleaved by APC, multiple polypeptides, representing intermediate and terminal digest fragments derived from the heavy chain, have been observed. Walker, F. J. et al., *Arch. Bioch. Biophys.* 252: 322 (1987). These fragments result from cleavage site locations at Arg336, the unction of the A1 and A2 domain, at Arg562, bisecting the A2 domain, and a site at the A2-B junction, likely at Arg740. Fay, P. J. et al., *J. Biol. Chem.* 266: 20139 (1991). APC cleavage of FVIII at residue 336 generates a 45 kDa fragment from the amino-terminus of the A1-domain and cleavage at residues 562 and 740 generates a 25 kDa fragment from the carboxy-terminus of the A2-domain (see FIG. 1A).

Previous transfection studies demonstrated that FVIII is 10-fold less efficiently secreted than FV. The inefficient secretion of FVIII correlates with binding to the protein chaperonin identified as the immunoglobulin binding protein (BiP), also known as the glucose-regulated protein of 78 kDa (GRP78) (Munro, S. et al., *Cell* 46:291-300 (1986)) within the lumen of the ER (Dorner, A. J. et al., *EMBO J.* 4:1563-1571 (1992)). BiP is a member of the heat-shock protein family that exhibits a peptide-dependent ATPase activity. Flynn, G. C. et al., *Science* 245:385-390 (1989). BiP expression is induced by the presence of unfolded protein or unassembled protein subunits within the ER. Lee, A. S., *Curr. Opin. Cell Biol.* 4:267-273 (1992) and Kozutsumi, Y. et al., *Nature* 332:462-464 (1988). It has been shown that high level FVIII expression induces BiP transcription. Dorner, A. J. et al., *J. Biol. Chem.* 264:20602-20607 (1989). In addition, FVIII release from BiP and transport out of the ER requires high levels of intracellular ATP. Dorner, A. J. et al., *PNAS (USA)* 87:7429-7432 (1990). In contrast, it has been found that FV does not associate with BiP and does not require high levels of ATP for secretion. Pittman, D. D. et al., *J. Biol. Chem.* 269: 17329-17337 (1994). Deletion of the FVIII-B-domain yielded a protein that bound BiP to a lesser degree and as more efficiently secreted. Dorner, A. J. et al., *J. Cell Biol.* 105:2665-2674 (1987). To evaluate whether the FVIII B-domain was responsible for BiP interaction, FV and FVIII chimeric cDNA molecules were constructed in which the B-domain sequences were exchanged. Pittman, D. D. et al., *Blood* 84:4214-4225 (1994). A FVIII hybrid harboring the B-domain of FV was expressed and secreted as a functional molecule, although the secretion efficiency of the hybrid was poor, similar to wild-type FVIII. Pittman, D. D. et al., *Blood* 84:4214-4225 (1994). This indicated that the difference in secretion efficiency between FV and FVIII was not directly attributable to specific sequences within the FVIII B-domain, the most divergent region between these homologous coagulation factors.

To determine whether specific amino acid sequences within FVIII A-domain inhibit secretion, chimeric proteins containing the A1- and A2-domains of FVIII or FV were studied. The chimeric protein containing the A1- and A2-domains of FV was secreted with a similar efficiency as wild-type FV. The complementary chimera having the A1- and A2-domains of FVIII was secreted with low efficiency similar to wild-type FVIII. These results suggested that sequences within the A1- and A2-domains were responsible for the low secretion efficiency of FVIII. An A1-domain-deleted FVIII molecule was constructed and secretion was increased approximately 10-fold compared to wild-type FVIII A2-domain-deleted FVIII. Expression of the FVIII A1-domain alone did not yield secreted protein, whereas expression of the FVIII A2-domain alone or the FV A1-domain or A2-domain alone directed synthesis of secreted protein. Secretion of a hybrid in which the carboxyl-terminal 110 amino acids of the A1-domain were replaced by homologous sequences from the FV A1-domain (226-336 hybrid FVIII) was also increased 10-fold compared to wild-type FVIII, however, the secreted protein was not functional, i.e. did not display procoagulant activity, and the heavy and light chains were not associated. Marquette, K. A. et al., *J. Biol. Chem.* 270:10297-10303 (1995). It would thus be desirable to provide a functional recombinant FVIII protein having increased secretion as compared to wild-type FVIII. It would also be desirable to provide a functional recombinant FVIII protein with increased secretion as well as increased specific activity.

Previous studies have demonstrated that the B-domain of FVIII is dispensable for FVIII cofactor activity. Genetically engineered FVIII molecules that have varying degrees of B-domain deletion (BDD) yield secreted single chain FVIII species in which no intracellular proteolysis of the primary translation product is observed. These BDD FVIII mutants are advantageous because they are more efficiently produced in mammalian cells. Functional characterization of these BDD FVIII molecules demonstrated that FVIII cofactor activity is retained if thrombin cleavage after Arg372, Arg740 and Arg1689 occurs. Therefore, any functional construction of FVIII genetically engineered thus far generates a FVIIIa heterotrimer following thrombin activation. The functional advantages of previous BDD FVIII constructs has therefore been limited by rapid dissociation of the non-covalently linked A2 subunit from FVIIIa.

It would thus be desirable to provide improved recombinant FVIII protein. It would also be desirable to provide FVIIIa protein that is resistant to activation. It would further be desirable to provide FVIIIa protein that is APC-resistant. It would also be desirable to provide FVIII protein having increased secretion as compared to wild-type FVIII. It would further be desirable to provide FVIII protein having increased secretion and APC-resistance. It would also be desirable to provide FVIII protein having increased secretion and inactivation resistance. It would also be desirable to provide a method of treating hemophiliac patients with improved recombinant FVIII. It would further be desirable to provide a method for treating hemophiliac patients via replacement therapy, wherein the amount of FVIII protein required to treat the patient is decreased.

SUMMARY OF INVENTION

The present invention provides novel purified and isolated nucleic acid sequences encoding procoagulant-active FVIII protein. In one embodiment, the nucleic acid sequences of the present invention encode amino acid sequences corresponding to known human FVIII sequences, wherein the A1-domain, specifically amino acid residue 309, phenylalanine, is mutated. In one embodiment, Phe309 is either deleted or substituted with any other amino acid residue, preferably serine. In another embodiment, the human FVIII sequences are B-domain deleted (BDD-FVIII). The resulting FVIII protein is capable of secretion at levels higher than typically obtained with wild-type FVIII and retains procoagulant activity.

In another embodiment, the nucleic acid sequences of the present invention encode FVIII B-domain mutants, wherein a portion of the B-domain is deleted. In particular, it has been shown that the addition of N-linked glycosylation sites can improve the secretion of BDD-FVIII up to 10-fold, as well as increase FVIII expression in vivo.

In a further embodiment, the secretion efficiency of a FVIII B-domain mutant comprising 226 amino acids at the amino-terminal end of the B domain and 6 consensus sites for N-linked glycosylation is further enhanced with the point mutation F309S.

In yet another embodiment, FVIII with minimal B domain content can provide more efficient expression in vitro and in vivo (FIG. 31).

In yet another embodiment, the nucleic acid sequences of the present invention encode amino acid sequences corresponding to known human FVIII sequences wherein APC cleavage sites have been mutated. In a preferred embodiment, amino acid residues 336 and 562 are mutated preferably from arginine to isoleucine and arginine to lysine, respectively. The resulting FVIII protein is APC resistant and thus for convenience, is generally referred to herein as "APC resistant FVIII."

In a further embodiment, the nucleic acid sequences of the present invention encode amino acid sequences corresponding to known human FVIII sequences wherein the B-domain is deleted, the von Willebrand factor (vWF) binding site is deleted, a thrombin cleavage site is mutated, and an amino acid sequence spacer is inserted between the A2- and A3-domains. In a preferred embodiment, the thrombin cleavage site Arg740 is mutated, preferably by substitution with alanine. In another preferred embodiment, the amino acid sequence spacer is the amino portion of the B-domain, preferably the 54 residues of the amino portion of the B-domain. In yet another preferred embodiment, one or both of the APC cleavage sites is mutated, as described herein. It has been surprisingly found that upon activation by thrombin, this protein is a heterodimer, wherein the A2-domain remains covalently associated with the light chain (see FIG. 1B). This heterodimer configuration is more stable than the wild-type heterotrimer configuration and has an approximate five-fold increase in specific activity compared to purified wild-type FVIII. Thus, in a preferred embodiment, the FVIII of the present invention is secreted as a single-chain polypeptide which, upon activation by thrombin, achieves an inactivation resistant FVIII heterodimer. For convenience, this novel FVIII of the present invention is generally referred to herein as "inactivation resistant FVIII."

In yet a further embodiment, the inactivation resistant FVIII of the present invention may be induced to bind to von Willebrand factor (vWF). It has been found that in the presence of an anti-light chain antibody, ESH8, the inactivation resistant FVIII of the present invention, which lacks the vWF binding site, has an increased binding affinity to vWF. Such an antibody or other cross-linking agent which induces binding to vWF may, therefore, be used to further stabilize the inactivation resistant FVIII of the present invention.

In another embodiment, the nucleic acid sequences of the present invention encode APC resistant FVIII amino acid sequences having a mutation at residue 309, phenylalanine. Preferably, Phe309 is deleted or substituted with another amino acid, e.g., serine. The nucleic acid sequences of the present invention may also encode an activation resistant FVIII amino acid sequences having a mutation at Phe309. Again, Phe309 is preferably deleted or substituted with another amino acid, e.g., serine. It will further be appreciated that the nucleic acid sequences of the present invention may encode APC resistant FVIII and inactivation resistant FVIII amino acid sequences having a mutated B-domain, i.e. the addition of N-linked glycosylation sites in an otherwise BDD-FVIII.

Thus, the nucleic acid sequences of the present invention encode FVIII proteins that exhibit inactivation resistance and/or increased secretion.

It will be appreciated to those skilled in the art that due to the inactivation resistance of the proteins of the present invention and accompanying increased specific activity, a lower dosage of protein may be administered to hemophiliac patients during FVIII replacement therapy. Thus, by utilizing the proteins of the present invention, the total exposure of protein to the patient is reduced, thereby lowering the likelihood of inhibitor formation. It will further be appreciated that the novel FVIII of the present invention will also be useful in gene therapy applications.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 1A is a diagram of the wild-type FVIII and FV domain structures;

FIG. 1B is a diagram of the inactivation resistant FVIII of the present invention;

FIG. 2 is a table showing secretion activity of the A-1 mutated FVIII proteins of the present invention compared to wild-type FVIII;

FIG. 23 is a graph illustrating vWF binding to inactivation resistant FVIII immobilized on Mab NMC-VIII/5;

FIGS. 25A and 25B are graphs illustrating the binding affinity of the inactivation resistant FVIII/ESH8/SPIII complex to phospholipids;

FIG. 27 is a diagram that depicts vWF affinity, PL affinity, and cofactor activity in the presence of vWF for FVIII LC, FVIIIa LC, inactivation resistant FVIII/ESH8 with and without thrombin;

DETAILED DESCRIPTION OF THE PREFERRED EMBODIMENTS

Novel purified and isolated nucleic acid sequences encoding procoagulant-active FVIII are provided. Nucleic acid sequences encoding amino acid sequences corresponding to known human FVIII sequences, that include an A1-domain mutation are provided. More specifically, nucleic acid sequences are provided that encode amino acid sequences corresponding to known human FVIII sequences wherein amino acid residue 309, phenylalanine, is mutated. In a preferred embodiment, Phe309 is either deleted or substituted with any other amino acid residue, preferably serine. In another embodiment, the human FVIII sequences are B-domain deleted (BDD-FVIII). The resulting FVIII protein is capable of secretion at levels higher than typically obtained with wild-type FVIII and retains procoagulant activity.

In another embodiment, the nucleic acid sequences of the present invention encode FVIII B-domain mutants, wherein a portion of the B-domain is deleted. In particular, it has been shown that the addition of N-linked glycosylation sites can improve the secretion of BDD-FVIII up to 10-fold, as well as increase FVIII expression in vivo. In one embodiment, the nucleic acid sequences of the present invention encode FVIII B domain mutants, wherein the B domain is truncated i.e., the BBD-FVIII includes increasing segments from the amino-terminal end of the B domain. In one embodiment, increasing segments from the amino-terminal end by 29 amino acids demonstrated a 1.7-fold improved secretion of BDD-FVIII. In yet another embodiment, increasing segments from the amino-terminal end of the B domain by 54 amino acids demonstrated a 3.4-fold improved secretion of BDD-FVIII. In still another embodiment, increasing segments from the amino-terminal end of the B domain by 117 amino acids demonstrated a 5.3-fold improved secretion of BDD-FVIII. In a further embodiment, increasing segments from the amino-terminal end of the B domain by 163 amino acids demonstrated a 8.5-fold improved secretion of BDD-FVIII. In yet another embodiment, increasing segments from the amino-terminal end of the B domain by 226 amino acids demonstrated a 10.8-fold improved secretion of BDD-FVIII. It has thus been found that the FVIII B-domain mutants of the present invention show increased secretion proportionate to their N-linked oligosaccharide content.

Figure 28:
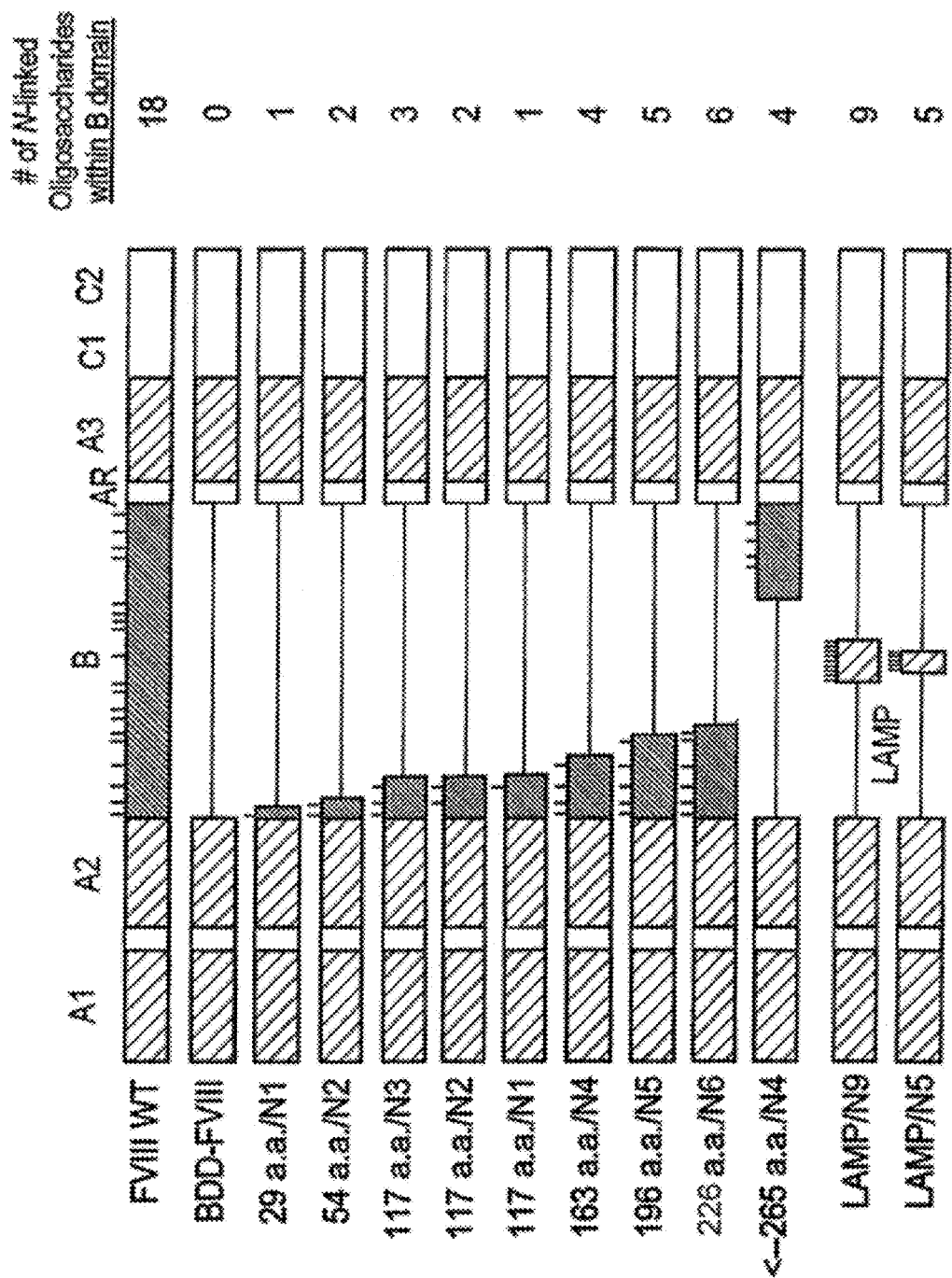
FIG. 28 is a diagram of FVIII B-domain mutants with increasing number of N-linked oligosaccharide content.

In a further embodiment, the nucleic acid sequences of the present invention encode a hybrid FVIII molecule, which includes a FVIII B-domain mutant and the Phe309 mutant, as described herein. In one embodiment, the FVIII B-domain mutant comprises 226 amino acids at the amino-terminal end of the B-domain (also referred to herein as the "b226N6 B domain variant" which includes 6 consensus sites for N-linked glycosylation, see FIGS. 28 and 29). This embodiment, yields superior expression and activity as compared to either mutation alone.

In a further embodiment, the secretion efficiency of a FVIII B-domain mutant comprises 226 amino acids at the amino-terminal end of the B domain and includes 6 consensus sites for N-linked glycosylation (also referred to herein as the "226N6 variant" or "226aa/N6 variant") and is further enhanced with the point mutation F309S. The combined F309S and B domain 226aa/N6 variant is also referred to herein as the "F309/226aa/N6 variant" or "309S/226aa/N6."

Figure 31:
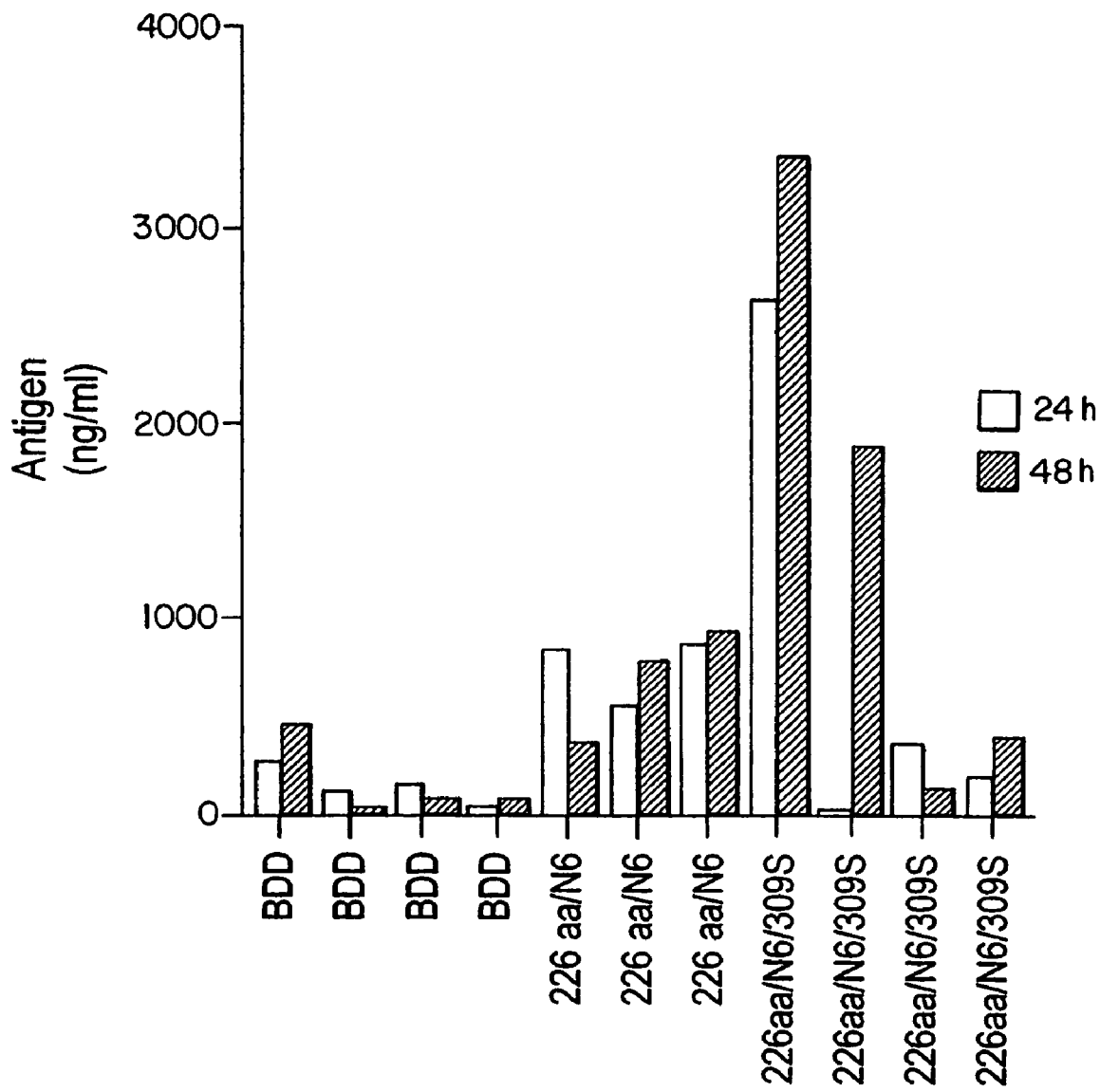
FIG. 31 is a graph that depicts expression of FVIII B domain variants in hemophilia A mice following hydrodynamic tail vein injection of plasmid DNA.

In yet another embodiment, FVIII with minimal B domain content can provide more efficient expression in vitro and in vivo (FIG. 31).

Nucleic acid sequences encoding amino acid sequences corresponding to known human FVIII sequences containing mutated APC cleavage sites are also provided. In a preferred embodiment, the APC cleavage sites Arg336 and Arg562 are mutated, preferably to isoleucine and lysine, respectively (R336I and R562K). The resulting FVIII protein is APC resistant.

Nucleic acid sequences are also provided which encode amino acid sequences corresponding to known human FVIII sequences, wherein the B-domain is deleted, the von Willebrand factor binding site (i.e., the acidic region of the amino terminus of the light chain) is deleted, a thrombin cleavage site is mutated, and an amino acid sequence spacer is inserted between the A2- and A3-domains. This embodiment may further include an APC cleavage site mutation, for example one or both of the APC cleavage site mutations described herein. In a preferred embodiment, the thrombin cleavage site Arg740 is mutated, preferably by substitution with alanine (R740A) or lysine (R740K). The amino acid sequence spacer is of a sufficient length to allow the protein to be activated by thrombin to achieve a heterodimer, wherein the A2-domain remains covalently associated with the light chain. In a preferred embodiment, the spacer is approximately 54 residues in length. In another preferred embodiment, the spacer comprises the 54 residues of the amino portion of the wild-type FVIII B-domain, i.e. residues 741 to 794, wherein residue 794 is threonine or leucine. The single-chain polypeptide upon activation with thrombin, becomes a heterodimer, having an approximate five-fold increase in specific activity compared to purified wild-type FVIII.

In a further embodiment, the inactivation resistant FVIII of the present invention may be employed in combination with an antibody or cross-linking agent which increases the protein's binding affinity to vWF. For example, when the vWF binding site-deleted inactivation resistant FVIII of the present invention is in the presence of ESH8, a commercially available mouse monoclonal antibody (American Diagnostics, Inc. Greenwich, Conn.), which recognizes an epitope at amino acids 2248 to 2285 within the C2-domain, the inactivation resistant FVIII binds to vWF. As set forth in greater detail in Example 4, the inactivation resistant FVIII of the present invention has at least a 10-fold reduced affinity for vWF compared to wild-type FVIII, however, in the presence of ESH8, it has only a 2-fold reduced affinity for vWF. It has recently been reported that ESH8 can function as an inhibitor of wild-type FVIII activation by increasing the affinity of thrombin-cleaved FVIII (FVIIIa) for vWF. Saenko, E. L. et al., *Blood* 86, Abstract No. 749 (1995). By delaying the release of FVIIIa from vWF, A2 dissociation and further proteolytic cleavages likely inactivate the FVIIIa before it can fully release from vWF and exert its cofactor function. A human inhibitor antibody that recognizes an epitope at amino acids 2218 to 2307 within the C2-domain has also been reported that appears to inhibit wild-type FVIII activation by a similar mechanism and may similarly be used to induce vWF binding. Shima, M. et al., *Blood* 86, Abstract No. 748 (1995) and Shima, M. et al., *British J. Hematol.* 91: 714-721 (1995).

In yet a further embodiment, the nucleic acid sequences of the present invention encode APC resistant FVIII described herein, having an additional mutation at Phe309. Preferably, Phe309 is deleted or substituted with another amino acid, e.g., serine. The nucleic acid sequences of the present invention may also encode inactivation resistant FVIII described herein, also having an additional mutation at Phe309. Again, Phe309 is preferably deleted or substituted with another amino acid, e.g., serine. It will further be appreciated that the nucleic acid sequences of the present invention may encode APC resistant FVIII and inactivation resistant FVIII amino acid sequences having a mutated B-domain, i.e. the addition of N-linked glycosylation sites in an otherwise BDD-FVIII. Thus, the nucleic acid sequences of the present invention encode FVIII proteins that exhibit inactivation resistance and/or increased secretion.

It will be appreciated that due to the increased specific activity of the proteins of the present invention, a lower dosage of protein may be administered to hemophiliac patients while maintaining therapeutically effective FVIII activity levels. In addition to cost savings, by utilizing the proteins of the present invention in FVIII replacement therapy, the total exposure of protein to the patient is reduced, thereby lowering the likelihood of inhibitor formation. It will further be appreciated that the proteins of the present invention are also useful in gene therapy-related treatment.

DNA sequences for human FVIII are known, as are expression methods (see, e.g. Toole et al, *Nature* 312:312-317 (1984); Wood et al., *Nature* 312:330-337, Vehar et al., *Nature* 312:337-342, U.S. Pat. No. 4,757,006, WO 87/04187, WO 88/08035 and WO 88/03558). The novel purified and isolated nucleic acid sequences encoding the FVIII protein of the present invention, i.e. a nucleic acid sequence encoding a polypeptide sequence substantially the same as human FVIII or variants thereof modified as is known in the art and described herein, may be made by conventional techniques. For example, the mutations at Phe309 and the APC and thrombin cleavage sites may thus be made by site-directed mutagenesis of the cDNA. One of skill in the art will recognize that "mutation" refers to any alteration including but not limited to, substitutions, insertions and deletions. It will further be appreciated that the remainder of the FVIII nucleic acid sequence may vary from the wild-type FVIII by containing additional modifications such as those disclosed in U.S. Pat. No. 5,004,803, WO 86/06101, and WO 87/07144. FVIII analogs have been developed to better understand the specific structural requirements for FVIII activatibility, inactivatibility, and in vivo efficacy and are also within the scope of the present invention. Included among the features to be optimized are simplified preparation, ease of administration, stability, improved clearance/distribution characteristics, reduced immunogenicity, and prolonged half-life. Moreover, it will be appreciated that variant FVIII nucleic acid sequences in accordance with the present invention also include allelic variations, i.e. variations in sequence due to natural variability from individual to individual, or with other codon substitutions or deletions which still retain FVIII-type procoagulant activity.

Alternate nucleic acid forms, such as genomic DNA, cDNA, and DNA prepared by partial or total chemical synthesis from nucleotides, as well as DNA with mutations, are also within the contemplation of the invention.

Association of nucleic acid sequences provided by the invention with homologous or heterologous species expression control sequences, such as promoters, operators, regulators, and the like, allows for in vivo and in vitro transcription to form mRNA which, in turn, is susceptible to translation to provide novel FVIII proteins and related poly- and oligopeptides in large quantities. The present invention thus comprises the expression products of the nucleic acid sequences of the invention, as well as activated forms of these expression products. In a presently preferred expression system of the invention, FVIII encoding sequences are operatively associated with a regulatory promoter sequence allowing for transcription and translation in a mammalian cell to provide, for example, FVIII having clotting activity.

As used herein the term "procoagulant-active" and "active" FVIII, may be used interchangeably to refer to one or more polypeptide(s) or proteins demonstrating procoagulant activity in a clotting assay. The term FVIII may be used herein to encompass FVIIIa and one skilled in the art will appreciate from the context in which the terms are used which term (pre-thrombin activated FVIII or thrombin activated FVIII (FVIIIa)) is intended. As used herein, the term "polypeptides" includes not only full length protein molecules but also fragments thereof which, by themselves or with other fragments, generate FVIII procoagulant activity in a clotting assay. It will be appreciated that synthetic polypeptides of the novel protein products of the present invention are also within the scope of the invention and can be manufactured according to standard synthetic methods. It will also be appreciated that in the amino acid numbering system used herein, amino acid residue 1 is the first residue of the native, mature FVIII protein. It will further be appreciated that the term "domain" refers to the approximate regions of FVIII, known to those skilled in the art.

As used herein, the phrase "a sequence substantially corresponding to the sequence" is meant to encompass those sequences which hybridize to a given sequence under stringent conditions as well as those which would hybridize but for the redundancy of the genetic code and which result in expression products having the specified activity. Stringent conditions are generally 0.2× SSC at 65° C. The phrase "substantially duplicative" is meant to include those sequences which, though they may not be identical to a given sequence, still result in expression product, proteins, and/or synthetic polypeptides that have FVIII activity in a standard clotting assay.

The incorporation of the sequences of the present invention into prokaryotic and eucaryotic host cells by standard transformation and transfection processes, potentially involving suitable viral and circular DNA plasmid vectors, is also within the contemplation of the invention. Prokaryotic and eucaryotic cell expression vectors containing and capable of expressing the nucleic acid sequences of the present invention may be synthesized by techniques well known to those skilled in this art. The components of the vectors such as the bacterial replicons, selection genes, enhancers, promoters, and the like, may be obtained from natural sources or synthesized by known procedures (see, e.g. Kaufman et al., *J. Mol. Biol.* 159:601-621 (1982) and Kaufman, *PNAS* 82:689-693 (1995)). Expression vectors useful in producing proteins of this invention may also contain inducible promoters or comprise inducible expression systems as are known in the art.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Candidate cells need not be genotypically deficient in the selection gene so long as the selection gene is dominantly acting.

The use of mammalian host cells provides for such post-translational modifications, e.g. proteolytic processing, glycosylation, tyrosine, serine, or threonine phosphorylation, as may be made to confer optimal biological activity on the expression products of the invention. Established mammalian cell lines are thus preferred, e.g. CHO (Chinese Hamster Ovary) cells. Alternatively, the vector may include all or part of the bovine papilloma virus genome (Lusky et al., *Cell* 36:391-401 (1984)) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines, and the like.

Whichever type of expression vector is used, it may be preferable to co-express the FVIII nucleic acids of the present invention with a nucleic acid sequence encoding von Willebrand factor (vWF) or an analog thereof, e.g. as described in WO 87/06101, WO 88/08035 and U.S. Pat. No. 5,250,421. It may also be preferred to express the protein in media containing a protease inhibitor such as aprotinin, e.g. in an amount from about 0.01 to about 5%, preferably from about 0.5 to about 1.0%, (vol/vol) (Aprot., 15-30 Trypsin inhibitor units (TIU)/ml, Sigma) or corresponding amounts of activity units of other protease inhibitors.

Stable transformants are screened for expression of the procoagulant product by standard immunological or activity assays. The presence of the DNA encoding the procoagulant proteins may be detected by standard procedures such as Southern blotting. Transient expression of the procoagulant genes during the several days after introduction of the expression vector into suitable host cells such as COS-1 monkey cells, is measured without selection by activity or immunologic assay of the proteins in the culture medium. Following the expression of the DNA by conventional means, the protein so produced may be recovered, purified and/or characterized with respect to physicochemical, biochemical and/or clinical parameters, all by known methods.

In a further embodiment, the nucleotide sequences of the present invention may be used in gene therapy applications, e.g. to treat hemophilia caused by deficiency of FVIII. Due to the increased specific activity of the FVIII proteins of the present invention, therapeutically effective FVIII activity may be achieved with lower protein expression levels as compared to other forms of FVIII including wild-type FVIII. The methods of this invention thus comprise the step of introducing the nucleotide sequences of the present invention into a target cell. In order to effectuate transfer, the nucleotide sequences to be transferred must be associated with a vehicle capable of transducing the target cell. Those skilled in the art will appreciate that such vehicles include known gene therapy delivery systems including, but not limited to, adenoviral, retroviral and adeno-associated viral vectors, as well as liposomes and DNA-protein complexes.

The invention will be further understood with reference to the following illustrative examples and procedures, which is purely exemplary, and should not be taken as limiting the true scope of the present invention. Example 1 describes the preparation and analysis of the A1-domain mutated FVIII of the present invention. Example 2 describes the preparation and analysis of the APC resistant FVIII of the present invention. Example 3 describes the preparation and analysis of the inactivation resistant FVIII of the present invention. Example 4 describes the characterization of the intermolecular protein-protein interactions stabilizing FVIIIa. Example 5 describes the increase of the plasma stability of FVIIIa in vivo. Example 6 describes inducible vWF-binding of the inactivation resistant FVIII of the present invention. Example 7 describes the affinity and activity of inactivation resistant FVIII of the present invention. Example 8 describes the pharmacokinetics and efficacy of the inactivation resistant FVIII and inactivation resistant FVIII/ESH8 complex in animals. Example 9 describes the preparation and analysis of the FVIII B domain mutants of the present invention. Example 10 describes the characterization and analysis of the FVIII B domain mutants of the present invention. Example 11 describes expression of bioengineered FVIII in vivo. Example 12 describes pharmaceutical compositions and methods of use of the FVIII proteins and nucleotide sequences of the present invention.

EXAMPLE 1

Preparation and Analysis of A1-domain Mutated Factor VIII

A statistical algorithm (Blond-Elguindi, S. et al., *Cell* 75:717-728 (1993)) was applied to predict the BiP binding potential of 7-mer peptides to the 226-336 region of FVIII (residue 1 is the first amino acid residue of the native, mature FVIII protein). Residues Leu303 to Phe309 were found to have a BiP binding score of +14 where any score over +10 has an extremely high probability of binding BiP. Fay, P. J. et al., *J. Biol. Chem.* 266:8957-8962 (1991). This region contains a hydrophobic cluster where 7 of 11 amino acid residues are Leu or Phe.

Initially all 7 Leu and Phe residues in the potential BiP binding pocket were mutated to Ala. Site-directed mutagenesis by oligonucleotide overlap-extension polymerase chain reaction (PCR) mutagenesis was utilized. A FVIII/FV chimeric was produced wherein residues 226-336 of FVIII were replaced with the homologous residues from FV (residues 198-313). Marquette, K. A. et al., *J. Biol. Chem.* 270:10297-10303 (1995). Partially complementary primers that contained the mutation were utilized with two primers directed at the MluI sites at 226 and 336 in the FVIII/FV chimeric cDNA to amplify two overlapping products that contain the directed mutation. These two fragments were isolated and fused together by PCR using the two MluI site containing primers. The resultant MluI fragment was then subcloned into the MluI digested FVIII/FV 226-336 chimera within the expression vector pMT2. All mutations were confirmed by DNA sequencing over the PCR amplified region. Expression vectors encoding these mutants were transfected into COS-1 cells and the conditioned medium taken at 60 hr for analysis of FVIII activity by Coatest activity assay. When all 7 Leu and Phe residues in the potential BiP binding pocket were mutated to Ala, the molecule was not secreted. Subsequently, the Phe residues were individually mutated to the respective amino acid residues in FV. The secretion of the F309S mutants (either alone or in combination with other mutants) were reproducibly increased 2-fold in several transfection experiments. As shown in FIG. 2, mutations at other adjacent residues (F293S, F306W) did not improve secretion. The increased secretion of the F309S mutants correlated with a 2-fold increase in FVIII antigen, indicating a specific activity similar to wild-type FVIII. Metabolic labeling with [$^{35}$S]-methionine for 20 min with a 4 hr chase in medium containing excess unlabeled methionine indicated that the increased secretion of the F309 and Q,F305/309K,S mutants correlated with increased secretion compared to wild-type FVIII.

Stably transfected CHO cell lines were engineered that express the F309S mutant. Of 35 original transfected CHO cell clones selected for dihydrofolate reductase expression, 5 clones were obtained that express significant levels of FVIII (approximately 1 U/ml/$10^6$ cells/day). Two of these clones express the same level of FVIII as the original 10A1 cell line that was obtained by screening over 1000 original transfected cell clones. Kaufman, R. J. et al., *J. Biol. Chem.* 263:6352-6362 (1988). Thus, in low concentrations of methotrexate, the mutation permits high level FVIII expression to be obtained more readily.

Further selection in methotrexate is performed to determine if the maximum productivity of FVIII/cell is improved. Experiments are performed to measure BiP interaction and ATP dependence for secretion for the F309W/S functional FVIII mutant in the stably transfected CHO cells.

EXAMPLE 2

Preparation and Analysis of APC Resistant Factor VIII

Experimental Procedures

Materials. FVIII deficient plasma and normal pooled human plasma were obtained from George King Biomedical, Inc. (Overland Park, Kans.). Monoclonal antibody to the heavy chain of FVIII (F8) coupled to CL4B-sepharose was used and may be prepared by known methods. Activated partial thromboplastin (Automated APTT reagent) was purchased from General Diagnostics Organon Teknika Corporation (Durham, N.C.). Soybean trypsin inhibitor, phenylmethylsulfonylfluoride (PMSF) and aprotinin were purchased from Boehringer, Mannheim GmbH (Mannheim, Germany). Human á-thrombin was obtained from Sigma Chemical Co. (St. Louis, Mo.). Human APC was purchased from Enzyme Research Laboratories, Inc. (South Bend, Ind.). Dulbecco's modified eagle medium (DMEM), á-modification of Eagle's Medium (á-MEM) and methionine-free DMEM were obtained from Gibco BRL (Gaithersburg, Md.). Fetal bovine serum was purchased from PAA Laboratories Inc. (Newport Beach, Calif.).

Plasmid construction. Site-directed oligonucleotide-mediated mutagenesis was performed by the gapped-heteroduplex procedure to introduce Arg336Ile (R336I) and/or Arg562Lys (R562K) mutations into the FVIII cDNA cloned into the expression vector pED6, as described previously. Pittman, D. D. et al., *Method in Enzymology* Vol. 222 (San Diego, Calif.; Academic Press, Inc.) p. 236 (1993)) and Toole, J. J. et al., *PNAS* (*USA*) 83:5939 (1986). The mutations were confirmed by extensive restriction endonuclease digestion and DNA sequence analysis. The resultant molecules were designated R336I or R562K and the double mutant, referred to herein as APC resistant FVIII, was designated R336I/R562K. In addition, a R336I/K338I double mutant was also constructed.

Analysis of synthesis and secretion. Plasmid DNA was transfected into COS-1 cells by the diethyl aminoethyl (DEAE)-dextran procedure as described. Pittman, D. D. et al., *Method in Enzymology* Vol. 222 (San Diego, Calif.; Academic Press, Inc.) p. 236 (1993). Conditioned medium was harvested 60 hours post transfection in the presence of 10% heat-inactivated fetal bovine serum (FBS) for FVIII assay. Subsequently, cells were metabolically labeled with [$^{35}$S]-methionine as described before. Pittman, D. D. et al., *Method in Enzymology* Vol. 222 (San Diego, Calif.; Academic Press, Inc.) p. 236 (1993). Labeled conditioned medium was harvested and immunoprecipitated with F8 antibody coupled to CL4B sepharose. Immunoprecipitated proteins from the conditioned medium were washed with PBS containing Triton X-100, resuspended 50 mM Tris-HCl pH 7.5, 150 mM NaCl, 2.5 mM $CaCl_2$ and 5% glycerol (buffer A), and were treated with or without 8.5 U/ml of thrombin at 37° C. for 1 hour. Samples were analyzed by sodium dodecyl sulfate-polyacrylamide gel electrophoresis (SDS-PAGE) under reducing conditions and visualized by autoradiography after fluorography by treatment with En3hance (Dupont; Boston, Mass.).

Analysis of APC cleavage of FVIII. Radiolabeled and immunoprecipitated FVIII was resuspended with buffer A and treated with 30 ìg/ml of bovine APC in the presence of 100 ìg/ml inosithin and 10 mM $CaCl_2$ at 37° C. for 1.5 hr. The resulting polypeptides were separated by SDS-PAGE and visualized by autoradiography as described above.

Generation of CHO cell lines and purification of FVIII. In order to obtain large amounts of FVIII, stably transfected CHO cells lines were engineered containing DNA encoding the wild-type and APC resistant FVIII. The expression plasmids were digested with Cla1 and transfected into CHO cells using the lipofection method. Pittman, D. D. et al., *Method in Enzymology* Vol. 222 (San Diego, Calif.; Academic Press, Inc.) p. 236 (1993). Conditioned media were applied to a column of F8 antibody coupled CL-4B sepharose. The bound FVIII was eluted in buffer containing 60% ethylene glycol and concentrated by dialysis against a 10% polyethylene glycol (MW 15K-20K) containing buffer. Fay, P. J. et al., *J. Biol. Chem.* (in press) (1996). Concentrated samples were dialyzed against modified buffer A containing 5mM $CaCl_2$ (buffer B). The FVIII clotting activity of the purified preparations were about 20 U/ml. The structure of purified proteins was evaluated by SDS-PAGE and silver staining (Bio-Rad Laboratories; Hercules, Calif.).

FVIII assay. FVIII activities were measured in a one stage clotting assay using FVIII deficient plasma as substrate. One unit of FVIII activity is the amount measured in 1 ml of normal human pooled plasma. For thrombin activation, conditioned medium was diluted into buffer A and incubated at room temperature with 1 U/ml thrombin. After incubation for increasing periods of time, aliquots were diluted and assayed for FVIII activity.

APC inactivation of FVIII. Purified FVIII samples diluted to 3 U/ml in buffer B were mixed with 100 ìg/ml inosithin and human APC 100 ng/ml or buffer alone as a control. After increasing periods of time at 37° C., aliquots were diluted and the residual FVIII was determined.

Effect of APC resistant FVIII in the APC resistance assay. Twenty U/ml of purified FVIII was diluted with FVIII deficient plasma to 1 U/ml. These samples were tested by the commercialized APC resistance assay kit (Coatest APC Resistance; Chromogenix, Molndal, Sweden) according to the manufacturer.

Results

R336I, R562K, and R336I/R562K mutant FVIII molecules are efficiently secreted with FVIII activity similar to wild-type FVIII. The activity and secretion of FVIII mutants were measured by transient DNA transfection of COS-1 monkey cells. The FVIII clotting activity in the conditioned medium demonstrated that all mutants had FVIII activity similar to wild-type FVIII, approximately 300 mU/ml (see Table 1). Thrombin activation of the conditioned medium samples indicated that there was no difference in the rate of thrombin activation and decay of procoagulant activity. As shown in FIG. 3, all samples were immediately activated (3-5 fold) at 10 seconds after thrombin addition and were immediately inactivated. In FIG. 3, the symbols represent wild-type FVIII (X), R336I (•), R562K (◇) and R336I/R562K (⮝). To measure FVIII secretion, transfected cells were metabolically labeled with [$^{35}$S]-methionine for 2 hr and then chased for 4 hr in medium containing excess unlabeled methionine. The secreted proteins were analyzed by immunoprecipitation of labeled conditioned medium. As shown in FIG. 4A, wild-type FVIII and all mutants were secreted at similar levels as a 300 kDa single chain and a 200 kDa heavy chain and an 80 kDa light chain. As shown in FIG. 4B, thrombin cleavage for all molecules generated the light chain migrating at 73 kDa and the heavy chain derived fragments corresponding to the 50 kDa A1-domain and 43 kDa A2-domain as expected (FIG. 4B). In addition, for wild-type FVIII and R562K (FIG. 4B, lanes 7 and 9) there was some cleavage at residue 336 to yield a 45 kDa species. In contrast, R336I and R336I/R562K (FIG. 4B, lanes 8 and 10) mutants did not generate the 45 kDa species, indicating that isoleucine mutation at residue 336 is resistant to cleavage by excess thrombin. For FIGS. 4A and 4B, the molecular size markers are shown on the left, "Mock" represents cells that did not receive DNA, and sc, hc and lc represent single chain, heavy chain and light chain, respectively.

TABLE 1

| FVIII Clotting Activity in Conditioned Medium From Transfected COS-1 Cells | |
|---|---|
| | FVIII Clotting Activity (mU/ml) (n = 5) |
| Wild-type | 318.8 ± 36.3 |
| R336I | 306.4 ± 51.2 |
| R562K | 340.0 ± 44.8 |
| R336I/R562K | 308.4 ± 76.9 | data represents mean ± SD

R562K is completely resistant and R336I is mostly resistant to APC cleavage at the mutated site. APC cleavage of FVIIIa was evaluated by treating [$^{35}$S]-methionine labeled immunoprecipitated FVIII with APC. Analysis of APC cleavage products of wild-type FVIII analyzed by SDS-PAGE on a 5-15% gradient gel detected the heavy chain fragments of 50 kDa and 45 kDa representing the A1-domain, and of 43 kDa representing the A2-domain, that were not present in the conditioned medium of cells that did not receive DNA. As shown in FIG. 5A, lane 2, a lower molecular weight product at 25 kDa was detectable, representing the carboxy-terminus of A2-domain. As shown in FIG. 5A, lane 3, R336I FVIII was partially resistant to cleavage at residue 336, as indicated by an increase in the 50 kDa and a reduction of the 45 kDa cleavage products compared to wild-type. The R336I displayed no change in the amount of the 25 kDa species indicating efficient cleavage at residue 562. As shown in FIG. 5A, lane 4, R562K mutant FVIII was resistant to cleavage at residue 562 as indicated by the increase in the 43 kDa fragment and loss of the 25 kDa fragment. However, the R562K mutant was efficiently cleaved at 336 as indicated by an intense 45 kDa fragment. APC treatment of the R336I/R562K double mutant yielded an increase in the 50 kDa and 43 kDa species, and the reduction of 45 kDa and loss of 25 kDa species compared to wild-type FVIII (see FIG. 5A, lane 5). The migration of the 45 kDa fragment derived from APC cleavage of the R336I mutant was slightly reduced upon analysis by SDS-PAGE on an 8% polyacrylamide gel (see FIG. 5B, compare lanes 7 and 8). In order to determine whether this mutant may be cleaved at the adjacent lysine at residue 338, an R336I and K338I double mutant was made by site-directed mutagenesis. The R336I/K338I mutant did not generate the 45 kDa fragment upon APC digestion (see FIG. 5B, lane 9). In FIGS. 5A and 5B, molecular size markers are shown on the left and "Mock" represents cells that did not receive DNA.

Mutagenesis at both Arg336 and Arg562 in FVIII are required for resistance to APC inactivation. von Willebrand Factor (vWF) inhibits APC inactivation of FVIII. Koedam, J. A. et al., *J. Clin. Invest.* 82:1236 (1988) and Fay, P. J. et al., *J. Biol. Chem.* 266:2172 (1991). Therefore, to study APC inactivation, stably transfected CHO cells that express wild-type and the APC cleavage site mutants FVIII molecules were engineered. Conditioned medium was collected for FVIII purification. As shown in FIG. 6, analysis of the purified proteins by SDS-PAGE under reducing conditions and silver staining demonstrated that all molecules have similar polypeptide compositions of heavy chain (hc) and light chain (lc) with minimal degradation and absence of vWF. These purified proteins were then analyzed for functional inactivation by APC. As shown in FIG. 7A, the activity of all samples, except the R336I/R562K (⮝) double mutant, were reduced to 80% after 10 min incubation at 37° C. in the absence of APC and were subsequently stable for 60 min thereafter. In the presence of APC, wild-type FVIII (X) had residual activity of 38% at 10 min and 8% at 60 min. In the presence of APC, the inactivation of R336I (•) and R562K (◊) single mutants were similar and both slower than wild-type FVIII. After 60 min 41% and 30% of initial activity remained for the R336I and R562K mutants, respectively. In contrast, the R336I/R562K (▲) double mutant was resistant to inactivation and retained 76% activity after 60 min. The results thus demonstrate that the R336I/R562K double mutant was mostly resistant and both single mutants were only partially resistant to APC inactivation.

Ability of APC resistance assay kit to detect APC resistant FVIII. Presently, a commercially available APC resistance assay kit (Coatest APC Resistance; Chromogenix, Molndal, Sweden) is used to screen the plasma of patients with thrombotic disease associated with the FV R506Q mutation. The ability of this kit to detect APC resistant FVIII was tested by reconstitution of FVIII deficient plasma with either purified wild-type or purified mutant FVIII. The APC resistance ratio was calculated by the measure of the clotting time in the presence of APC divided by the clotting time in the absence of APC (see Table 2). Only the R336I/R562K double mutant demonstrated a lower APC resistance ratio than 2, a value indicative of an APC resistance phenotype. Svensson, P. J. et al., *N. Engl. J. Med.* 336:517 (1994).

TABLE 2

APC-Resistance Ratio of Wild-Type FVIII and Mutants in the Commercialized Assay Kit

| | APC-Resistance Ratio (n = 3) |
|---|---|
| Wild-type | 2.13 ± 0.06 |
| R336I | 2.10 ± 0.00 |
| R562K | 2.13 ± 0.06 |
| R336I/R562K | 1.73 ± 0.06 | data represents mean ± SD

Discussion

All mutants were efficiently secreted from COS-1 cells with a FVIII activity similar to wild-type FVIII. Analysis of APC cleavage was performed by [$^{35}$S]-methionine labeling of protein and analysis of FVIII in the conditioned medium after immunoprecipitation. The R336I mutant was partially resistant to cleavage at residue 336, but was sensitive to cleavage at Arg562. On the other hand, the R562K mutant was completely resistant to cleavage at residue 562, but was sensitive to cleavage at Arg336. These results indicate that either single mutation at Arg336 or Arg562 affects cleavage at the mutated site and that there is not a required order for APC cleavage at these two sites in FVIII. The double mutant R336I/R562K was partially resistant to cleavage at residue 336 and completely resistant at residue 562. The cleavage of R336I likely occurred at an adjacent residue, Lys 338, since a double mutant R336I/K338I was completely resistant to cleavage at this site. These results show that APC cleavage of FVIII can be ragged, i.e. it does not have a stringent spacing requirement for cleavage.

Analysis of the kinetics of APC cleavage in FVIII indicated that Arg562 was preferentially cleaved compared to Arg336 and this initial cleavage most closely correlated with the loss of cofactor activity. Fay, P. J. et al., *J. Biol. Chem.* 266:20139 (1991) The slower inactivation of the R562K single mutant as a consequence of cleavage resistance at residue 562 is consistent with the hypothesis, and that the resultant inactivation was due to cleavage at Arg336. However, the R336I single mutant was only partially inactivated by cleavage at Arg562. It has been shown that both single cleavage site mutants were inactivated at similar rates under the conditions described herein. Assuming that cleavage at Arg336 and Arg562 occur at the same time, the effect of cleavage at either Arg336 or Arg562 for inactivation of FVIII appear to be similar. The rapid inactivation of wild-type FVIII may be due to synergistic roles of cleavage at Arg336 and Arg562 for inactivation of FVIII.

At present, there are no reports describing patients with mutations in the APC cleavage sites of FVIII. To evaluate whether these mutations would have an APC resistance phenotype, the APC resistant FVIII molecules were tested in the commercially available APC resistance assay kit (Coatest APC Resistance; Chromogenix, Molndal, Sweden). Only the R336I/R562K double mutant demonstrated a lower APC-resistance ratio. This assay kit can not therefore, detect either single APC cleavage site mutants of FVIII. In contrast to FVIII, both FV APC single cleavage site mutants, Arg306Gln and Arg506Gln, showed reduced APC-resistance ratios in this assay. The results thus show that the commercially available APC resistance kit will not detect FVIII APC resistant mutants unless both APC cleavages are inhibited.

EXAMPLE 3

Preparation and Analysis of Inactivation Resistant Factor VIII

Experimental Procedures

Materials. Anti-heavy chain factor VIII monoclonal antibody (F-8), F-8 conjugated to CL-4B Sepharose and purified recombinant factor VIII protein were obtained from Genetics Institute Inc. (Cambridge, Mass.). Anti-human vWF horseradish peroxidase(HRP)-conjugated rabbit antibody was obtained from Dako Corp. (Carpinteria, Calif.). Anti-light chain factor VIII monoclonal antibodies, ESH-4 and ESH-8, were obtained from American Diagnostica, Inc. (Greenwich, Conn.). Factor VIII-deficient and normal pooled human plasma were obtained from George King Biomedical, Inc. (Overland Park, Kans.). Activated partial thromboplastin (Automated APTT reagent) and $CaCl_2$ were obtained from General Diagnostics Organon Teknika Corporation (Durham, N.C.). Human thrombin, soybean trypsin inhibitor, phenylmethylsulfonylfluoride and aprotinin were obtained from Boehringer, Mannheim GmbH (Mannheim, Germany). O-phenylendiamine dihydrochloride (OPD) was obtained from Sigma Chemical Co. (St. Louis, Mo.). [$^{35}$S]-methionine (>1000Ci/mmol) was obtained from Amersham Corp. (Arlington Heights, Ill.). En$^3$Hance was obtained from Dupont (Boston, Mass.). Fetal bovine serum was obtained from PAA Laboratories Inc. (Newport Beach, Calif.). Dulbecco's modified Eagle's medium (DMEM), methionine-free DMEM, OptiMEM, Biotin N-hydroxy succinimide ester, and streptavidin-horseradish peroxidase conjugate were obtained from Gibco BRL (Gaithersburg, Md.).

Plasmid mutagenesis. Mutagenesis was performed within the mammalian expression vector $pMT_2$(37) containing the FVIII cDNA($pMT_2$VIII). Mutant plasmids were generated through oligonucleotide site-directed mutagenesis utilizing the polymerase chain reaction (PCR). For a detailed description of oligonucleotide-directed mutagenesis, see Smith, M., *Annu. Rev. Genet.* 19:423 (1985).

Construction 1—90/73 R740K. Vector $pMT_2$90/73 was used as the DNA template. The 90/73 construct is described in Nesheim, M. et al., *J. Biol. Chem.* 266: 17815-17820 (1991) and Pittman, D. et al., *Blood* 70, Abstract No. 392 (1987). Generally, the 90/73 construct is wild-type FVIII cDNA sequence in which the B-domain and the vWF binding site (acidic region of the light chain) have been deleted (del 741-1689). Oligonucleotide-directed mutagenesis was used to create a PCR fragment, KpnI/R740K/ApaI, and was ligated into KpnI/ApaI digested pMT$_2$90/73.

Construction 2—90/b/73 R740K. Vector pMT$_2$VIII was used as the DNA template. Oligonucleotide-directed mutagenesis was used to create a PCR fragment, KpnI/b/1689 MluI (where b represents a DNA sequence encoding for amino acid residues 741 to 793 of the wild-type sequence followed by an MluI site predicting amino acids threonine and arginine at residues 794 and 795/1689), which was ligated into KpnI/MluI digested vector pMT$_2$ VIII/1689/MluI. The following amino acid sequence (and nucleotide sequence encoding same) is the preferred amino acid sequence spacer, wherein residue 794 may be threonine or leucine and is preferably threonine:

```
5' AGC TTC TCC CAG AAT TCA AGA CAC CCT AGC    (SEQ ID NO:
    S   F   S   Q   N   S   R   H   P   S     1)
                                               (SEQ ID NO:
                                               2)

ACT AGG CAA AAG CAA TTT AAT GCC ACC ACA ATT
 T   R   Q   K   Q   F   N   A   T   T   I

CCA GAA AAT GAC ATA GAG AAG ACT GAC CCT TGG
 P   E   N   D   I   E   K   T   D   P   W

TTT GCA CAC AGA ACA CCT ATG CCT AAA ATA CAA
 F   A   H   R   T   P   M   P   K   I   Q

AAT GTC TCC TCT AGT GAT TTG TTG ATG CTC TTG 3'
 N   V   S   S   S   D   L   L   M   L   L
```

Construction 3—90/b/73 R740A. Vector 90/b/73 was used as the DNA template (wherein b is described above and encodes threonine at residue 794). Oligonucleotide-directed mutagenesis was used to create a PCR fragment, KpnI/R740A/b/ApaI, which was ligated into KpnI/ApaI digested pMT$_2$90/73.

Construction 4—90/b/73 R740A/R1689A (DM1). Vector 90/b/73 R740A was used as the DNA template (wherein b is described above and encodes leucine at residue 794). Oligonucleotide-directed mutagenesis was used to create PCR fragment, KpnI/R740A/b/R1689A/ApaI, which was ligated into KpnI/ApaI digested pMT$_2$90/73.

Construction 5—90/b/73 R336I/R740A (DM2). Vector PMT$_2$VIII/R336I was digested with SpeI and KpnI. The fragment was ligated into SpeI/KpnI digested 90/b/73 R740A (wherein b is described above and encodes threonine at residue 794).

Construction 6—90/b/73 R336I/R562K/R740A (IR8). Vector PMT$_2$VIII/R562K was digested with BglII and KpnI. The BglII/R562K/KpnI fragment was ligated into BglII/KpnI digested 90/b/73 R336I/R740A (wherein b is described above and encodes threonine at residue 794).

The plasmid containing the wild-type FVIII cDNA sequence was designated FVIII WT. All plasmids were purified by centrifugation through cesium chloride and characterized by restriction endonuclease digestion and DNA sequence analysis.

DNA transfection and analysis. Plasmid DNA was transfected into COS-1 cells by the DEAE-dextran method. Conditioned medium was harvested at 64 hours post-transfection in the presence of 10% fetal bovine serum. FVIII activity was measured by one-stage APTT clotting assay on a MLA Electra 750. Protein synthesis and secretion were analyzed by metabolically labeling cells at 64 hours post-transfection for 30 minutes with [$^{35}$S]-methionine (300 mCi/ml in methionine-free medium), followed by a chase for 4 hours in medium containing 100-fold excess unlabeled methionine and 0.020% aprotinin. Cell extracts and conditioned medium containing labeled protein were harvested. WT and mutant FVIII proteins were immunoprecipitated from equal proportions of cell extract and conditioned medium with F-8 coupled to CL-4B Sepharose. Immunoprecipitates were washed and resuspended in Laemmli sample buffer. Samples were analyzed by electrophoresis on a reducing SDS-low bis-8% polyacrylamide gel. The gels were treated with En$^3$Hance and the proteins visualized by autoradiography.

Protein purification. Partially purified IR8 protein was obtained from 200 mls of conditioned medium from transiently transfected COS-1 cells by immunoaffinity chromatography. Partially purified FVIII WT protein was obtained from 200 mls of conditioned medium from stably transfected CHO cells and immunoaffinity purified in the same manner. The proteins eluted into the ethylene glycol-containing buffer were dialyzed and concentrated against a polyethylene glycol (MW ~15-20,000)-containing buffer and stored at −70° C.

FVIII activity assay. FVIII activity was measured in a one-stage APTT clotting assay by reconstitution of human FVIII-deficient plasma. For thrombin activation, protein samples were diluted into 50 mM Tris-HCl pH 7.5, 150 mM NaCl, 2.5 mM CaCl$_2$ and 5% glycerol, and incubated at room temperature with 1 U/ml thrombin. After incubation for increasing periods of time, aliquots were diluted and assayed for FVIII activity. One unit of FVIII activity is the amount measured in 1 ml of normal human pooled plasma.

FVIII antigen determination. FVIII antigen was quantified using a sandwich ELISA method utilizing anti-light chain antibodies ESH4 and ESH-8. Purified recombinant FVIII protein was used as a standard.

Results

Generation of FVIII inactivation resistance. All of the above constructs are based upon 90/73, wherein the B-domain (residues 795 to 1647) and the vWF binding site (residues 1648 to 1688, also referred to as the acidic region of the amino terminus of the light chain), have been deleted. Nesheim, M. et al., *J. Biol. Chem.* 266: 17815-17820 (1991) and Pittman, D. et al., *Blood* 70, Abstract no. 392 (1987). FIG. 8 sets forth the domain structures of wild-type FVIII and the above constructs as well as the mutations at the APC and thrombin cleavage sites. As described herein and in FIG. 8, “b” represents the amino acid sequence spacer which is of a sufficient length to allow the protein to be activated by thrombin to achieve a heterodimer, wherein the A2-domain remains covalently associated with the light chain. In a preferred embodiment, the amino acid sequence spacer is preferably the amino portion of the wild-type B-domain, i.e. amino acid residues 741 to 793 followed by an MluI site (for cloning purposes) predicting amino acids threonine or leucine, preferably threonine, at residue 794 and arginine at 795/1689.

Figure 3:
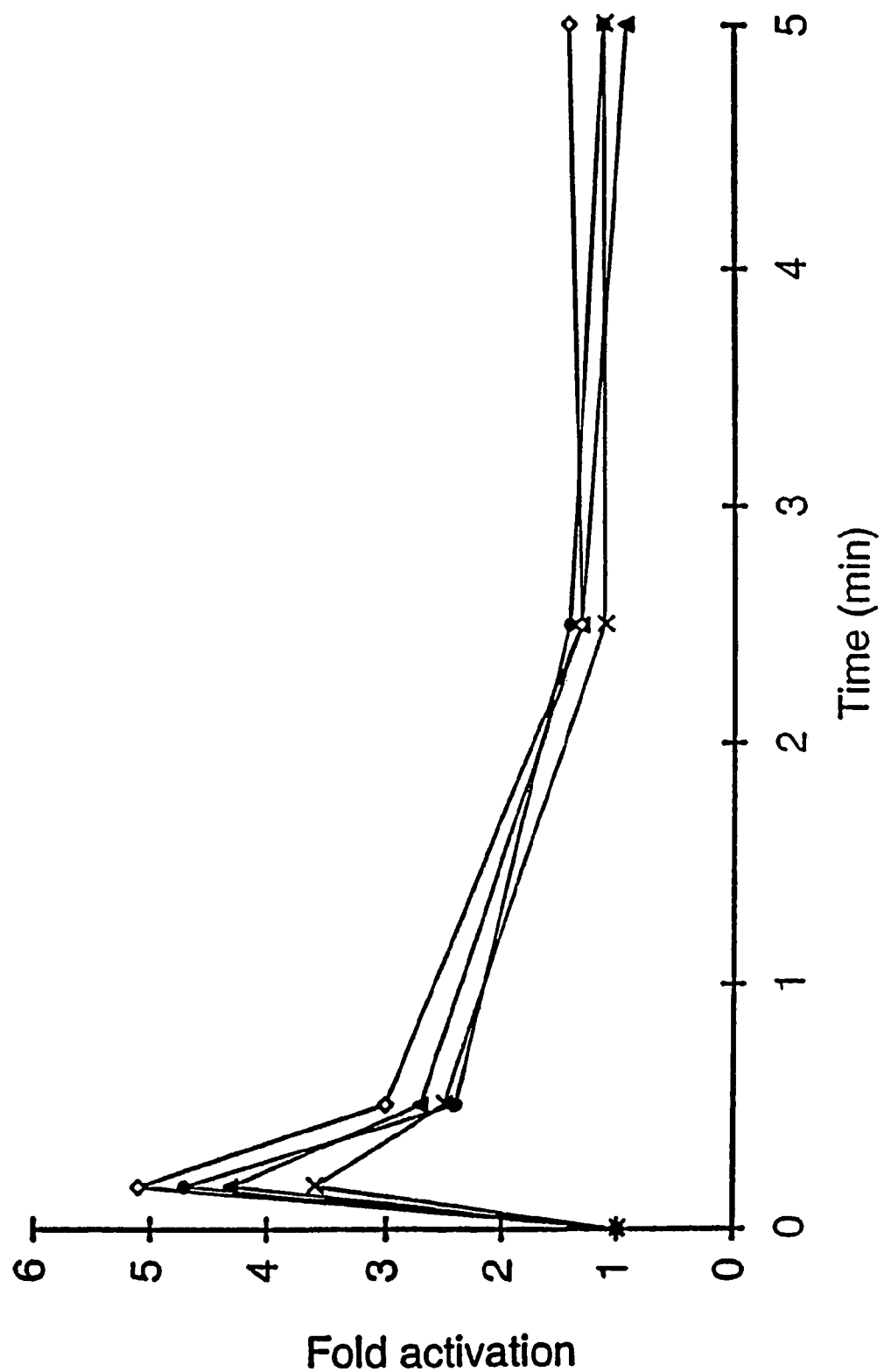
FIG. 3 is a graph showing the thrombin activation of APC resistant FVIII of the present invention and wild-type FVIII.
Figure 4A:
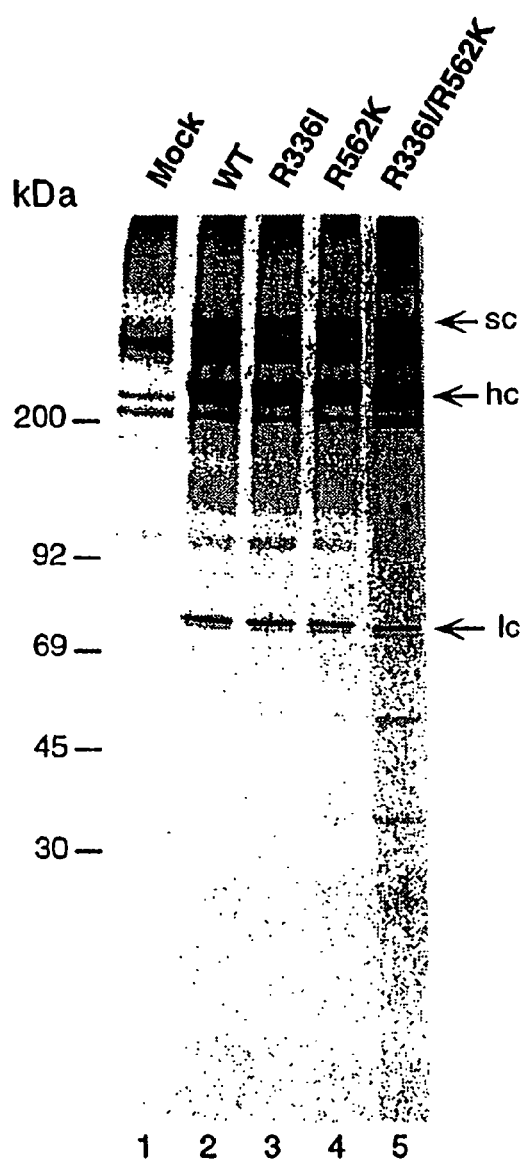
FIGS. 4A and 4B are photographs of gels showing the expression and thrombin cleavage of the APC resistant FVIII of the present invention.
Figure 4B:
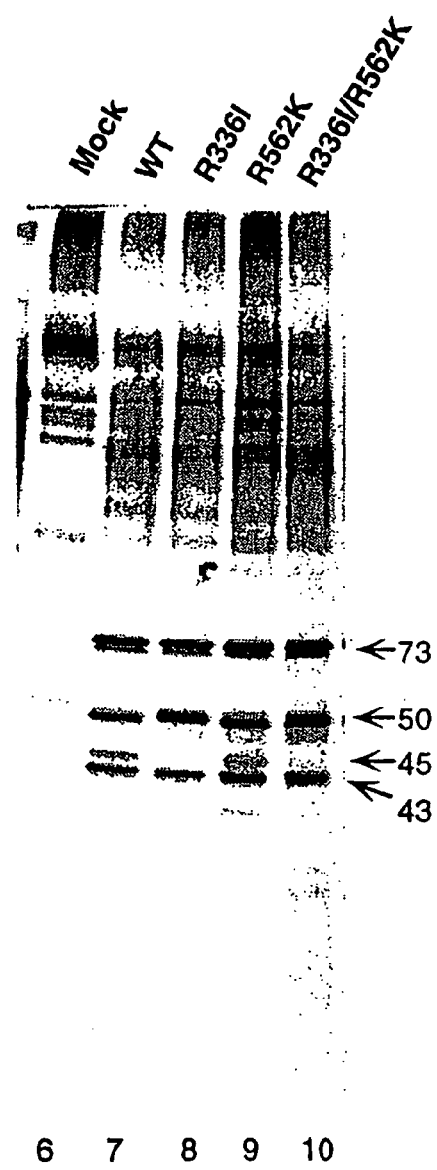
Figure 5A:
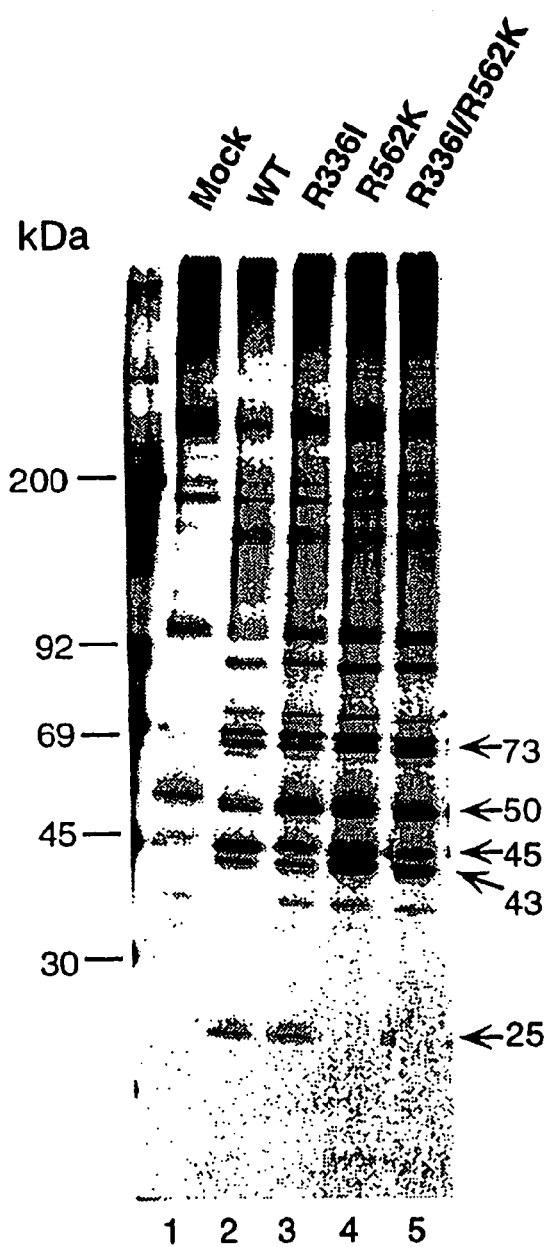
FIGS. 5A and 5B are photographs of gels showing APC cleavage of the APC resistant FVIII of the present invention.
Figure 5B:
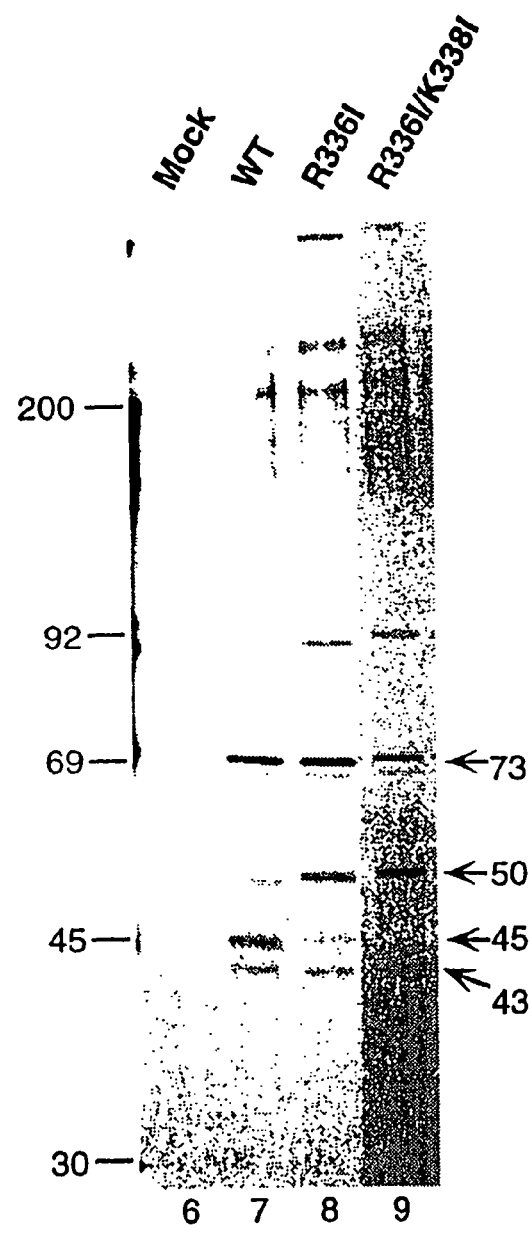
Figure 6:
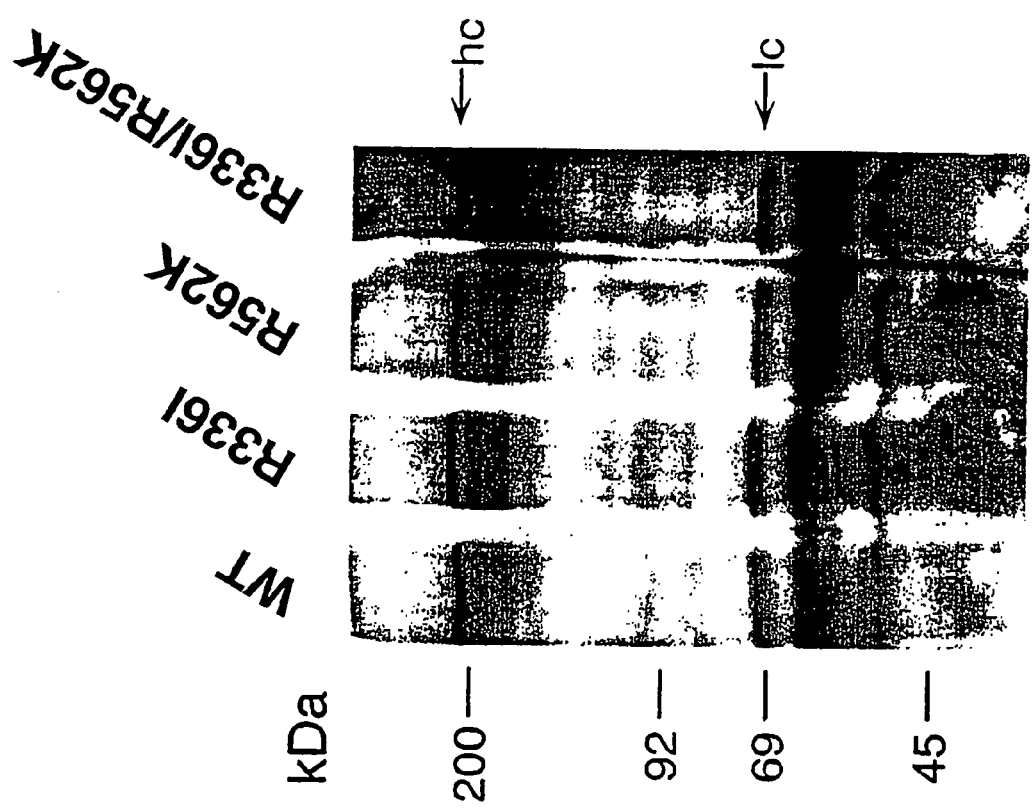
FIG. 6 is a photograph of a gel showing purified wild-type and APC resistant FVIII of the present invention.
Figure 7A:
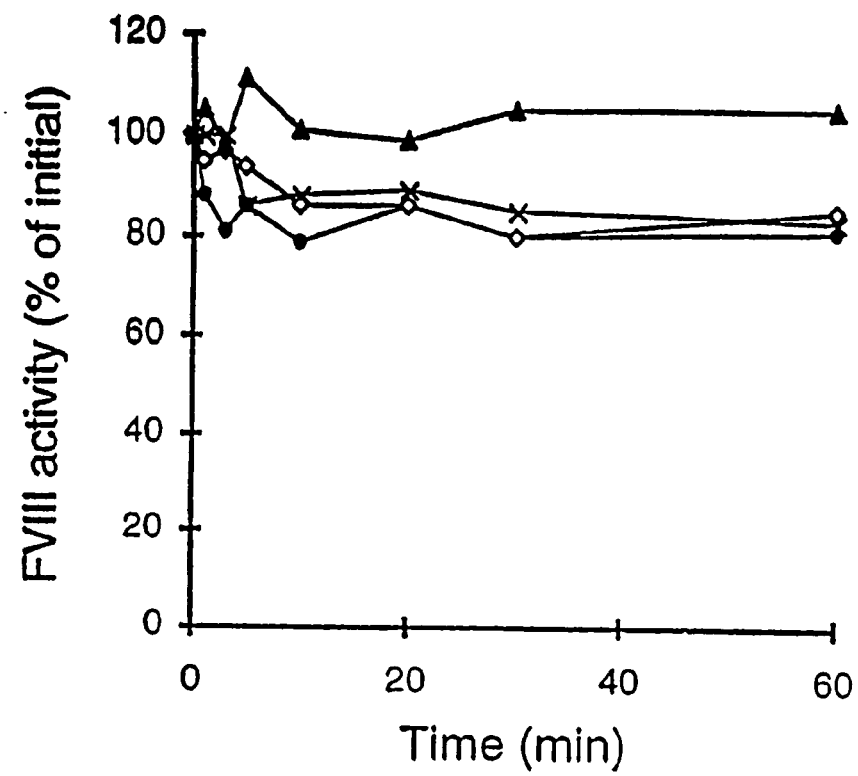
FIGS. 7A and 7B are graphs showing APC-mediated functional inactivation of wild-type and APC resistant FVIII of the present invention.
Figure 7B:
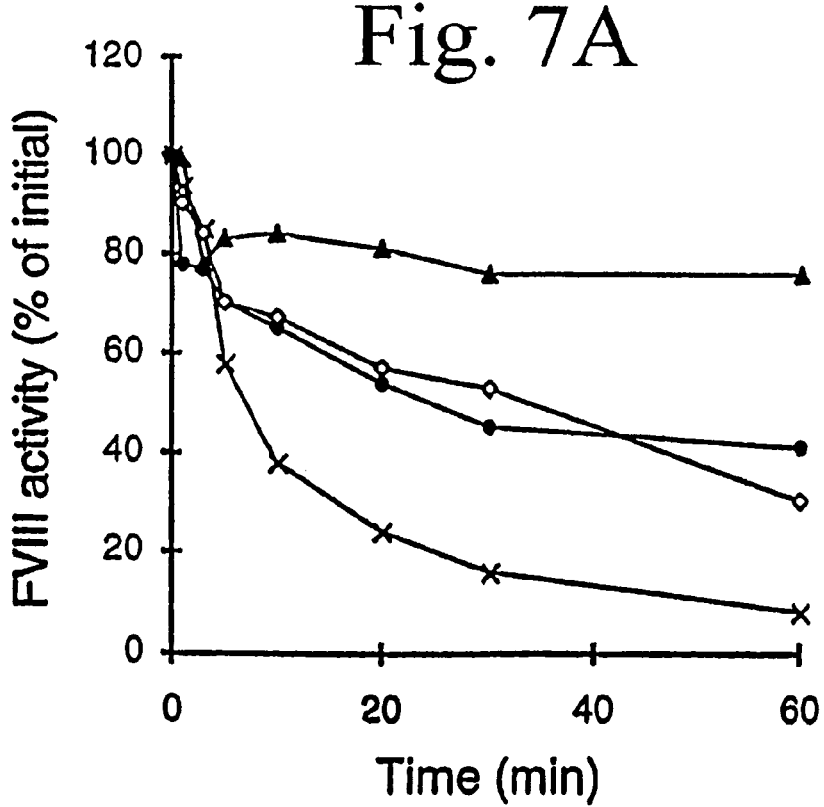
Figure 8:
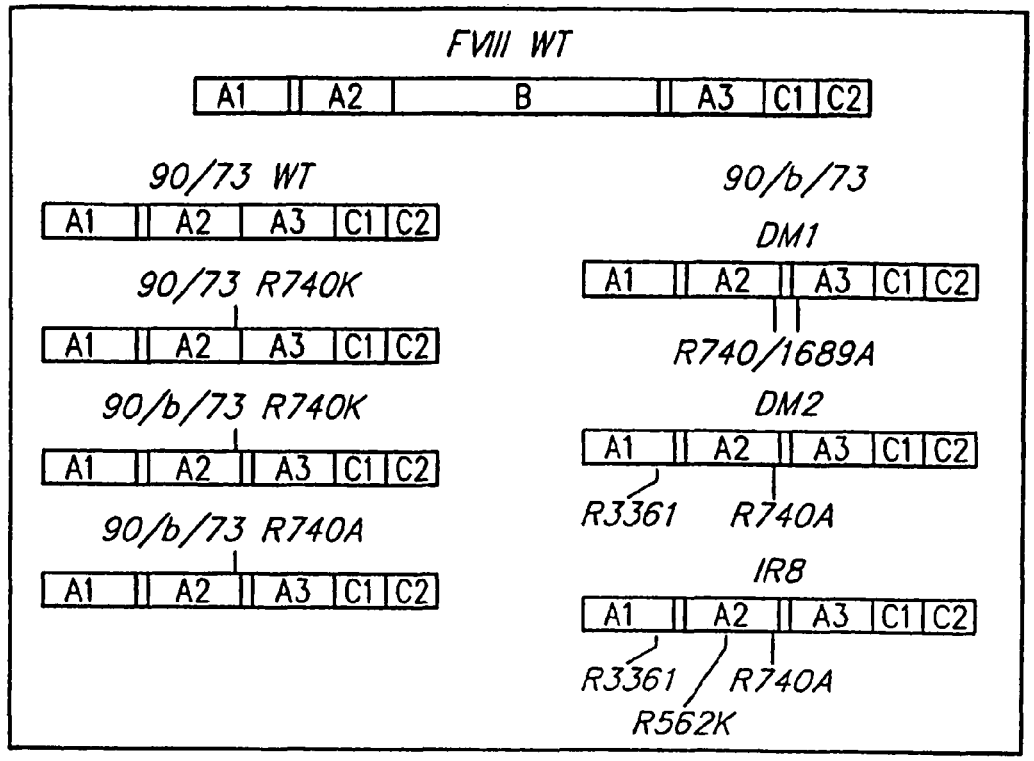
FIG. 8 is a diagram of the domain structure of the single-chain inactivation resistant FVIII of the present invention.
Figure 9:
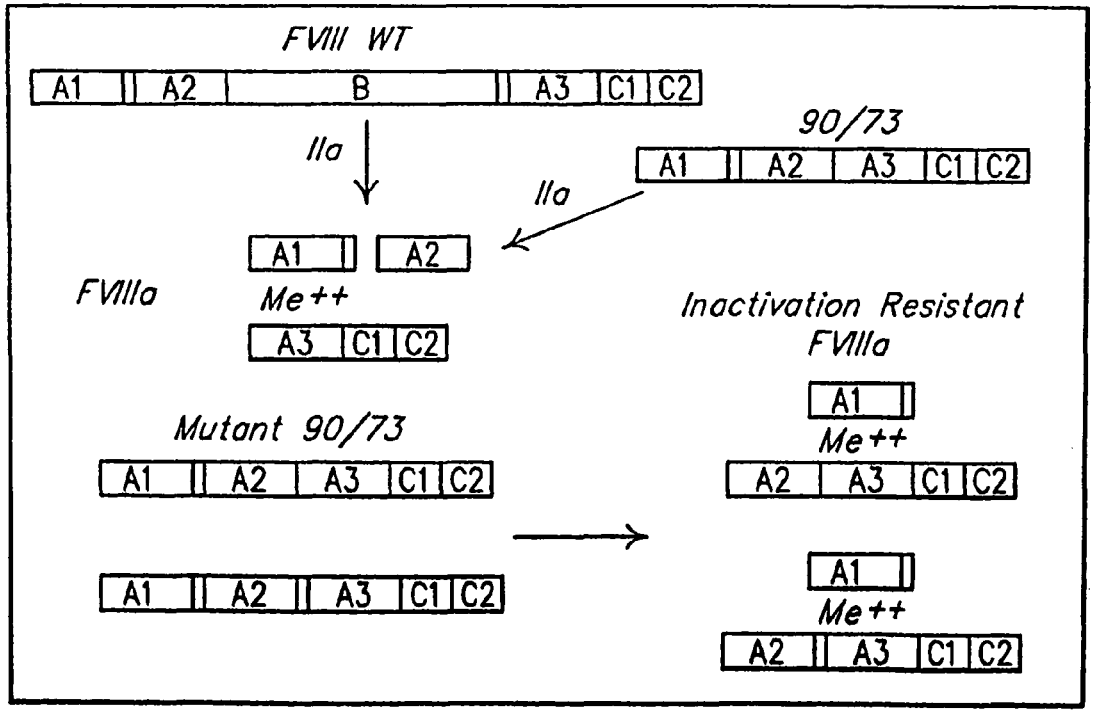
FIG. 9 is a diagram of the domain structure of the inactivation resistant heterodimer FVIII protein of the present invention.

FIG. 8 sets forth a model of activation of the constructs of the present invention. Wild-type FVIII and the mutant 90/73 both achieve a heterotrimer upon thrombin activation. When an amino acid sequence spacer is introduced between the A2- and A3-domains of 90/73 containing a mutation at the thrombin cleavage site (del795-1688/Arg336Iso/Arg562Lys/Arg740Ala), upon activation with thrombin, cleavage only occurs after Arg372, generating a FVIIIa heterodimer. This novel FVIII protein designated IR8, maintains stable activity following thrombin activation.

Figure 10:
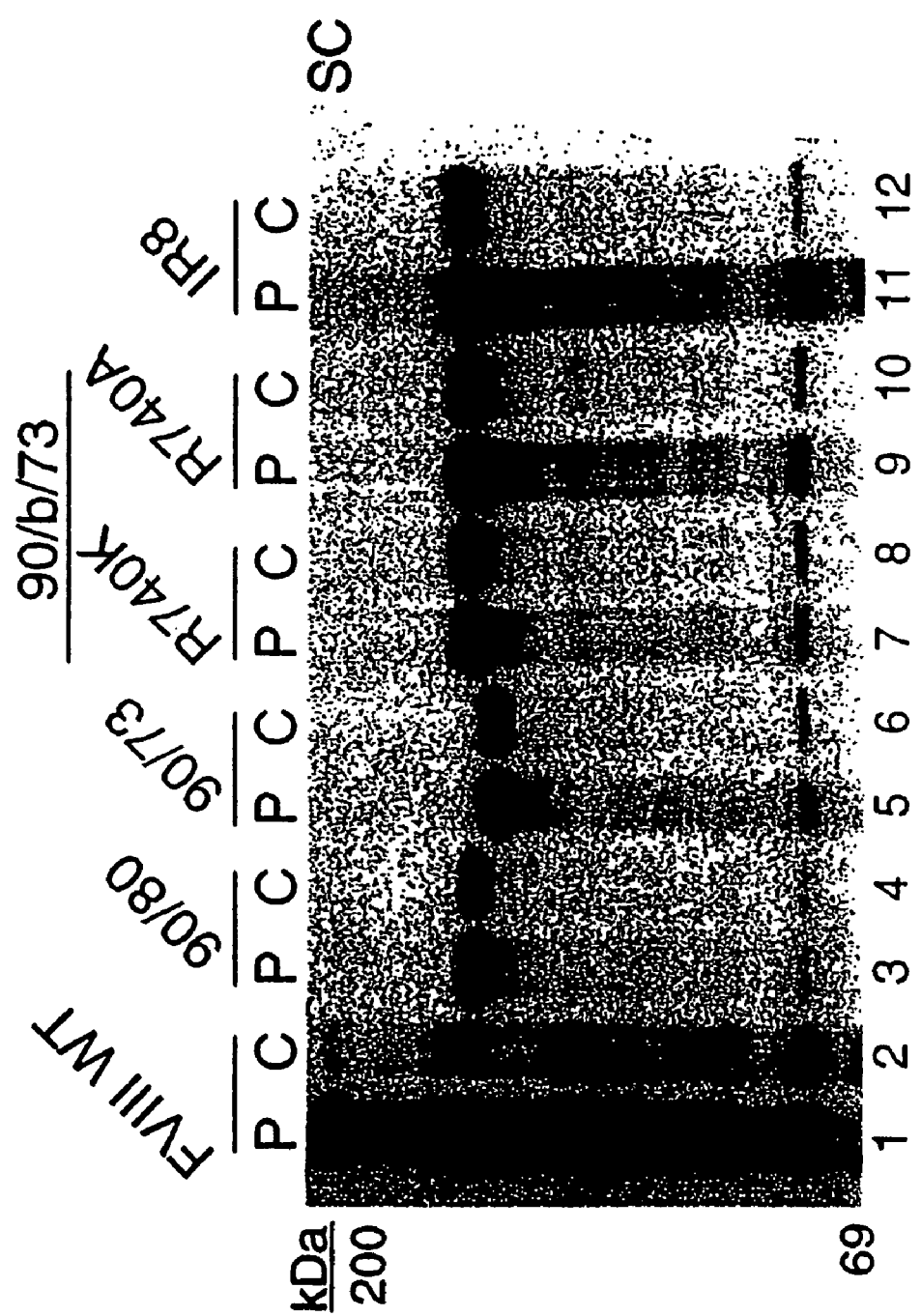
FIG. 10 is a photograph of a gel showing relative synthesis and secretion levels of the inactivation resistant FVIII of the present invention.
Figure 11:
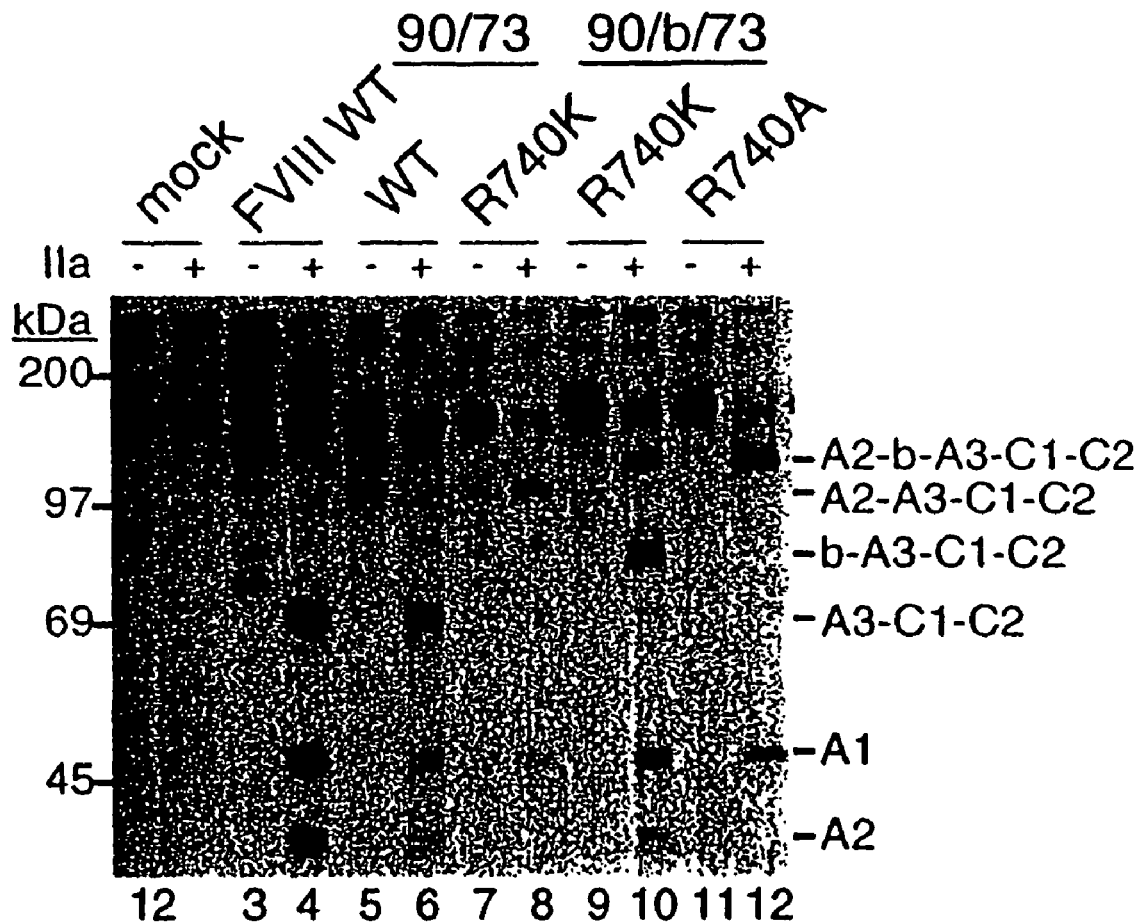
FIG. 11 is a photograph of a gel showing the cleavage patterns of the inactivation resistant FVIII of the present invention.

Synthesis and secretion of IR8. FVIII WT and the various inactivation-resistance mutants were compared by transient DNA transfection of the cDNA expression vectors into COS-1 monkey cells. At 60 hours following transfection, the rates of synthesis were analyzed by immunoprecipitation of cell extracts from [$^{35}$S]-methionine pulse-labeled cells. Intracellular FVIII WT was detected in its single chain form and migrated at approximately 250 kDa (FIG. 10, lane 1). The mutant 90/80 is a BDD FVIII mutant (del741-1648) previously characterized, that migrates at ~170 kDa and demonstrates an increased intensity from pulse-labeled cell extracts consistent with increased efficiency of synthesis (FIG. 10, lane 3). 90/73 migrates slightly faster due to the additional deletion of the residues of the acidic region (FIG. 10, lane 5). All the 90/b/73 based constructs including IR8 exhibited similar band intensity to the 90/80 and 90/73 constructs suggesting that the multiple missense mutations did not interfere with efficient protein synthesis. Additional bands within the cell extract are not observed in mock cell extract immunoprecipitated with an anti-FVIII specific antibody and represent both FVIII specific proteins and co-immunoprecipitating intracellular proteins. Following a 4 hour chase period, the majority of FVIII WT is lost from the cell extract (FIG. 10, lane 2) and can be recovered from chase conditioned medium in its 280 kDa single chain, 200 kDa heavy chain and 80 kDa light chain forms (FIG. 10, lane 3). Although all of the BDD and inactivation-resistance mutants demonstrated significant amounts of their primary translation products remaining within the cell extract following the 4 hour chase (FIG. 10, lanes 4, 6, 8, 10, 12), they were all recovered from the chase conditioned medium as single chain species (FIG. 11, lanes 5, 7, 9, 11, 13). Therefore the various alterations of the FVIII construct did not have significant impact on secretion.

Structural stability of IR8 following thrombin cleavage. The labeled FVIII proteins immunoprecipitated from the chase conditioned medium were incubated with thrombin (1 U/ml) for 30 minutes prior to SDS-PAGE analysis. FVIII WT was efficiently cleaved into a heterotrimer of fragments consisting of a 50 kDa A1 subunit, 43 kDa A2 subunit and 73 kDa thrombin-cleaved light chain, A3-C1-C2 (FIG. 11, lane 4). 90/73 WT was also cleaved into a heterotrimer of subunits similar to FVIII WT (FIG. 11, lane 6) consistent with previous observations and depicted in FIG. 1A. 90/73 Arg740Lys generated a heterodimer of thrombin-cleaved subunits consistent with a 50 kDa A1 subunit and an A2-A3-C1-C2 fused light chain (FIG. 11, lane 8). 90/b/73 Arg740Lys demonstrated thrombin cleavage fragments consistent with 2 heteromeric species, a 50 kDa A1/120 kDa A2-b-A3-C1-C2 heterodimer, as well as a 43 kDa A2 subunit and an ~85 kDa fragment consistent with a b-A3-C1-C2 fused light chain (FIG. 11, lane 10). The appearance of the A2 subunit following incubation with thrombin suggested that Lys740 did not completely abrogate thrombin cleavage in the presence of the b spacer. With the more radical missense mutation to Ala740, a stable heterodimeric species was demonstrated (FIG. 11, lane 12). This stable heterodimeric structure following thrombin cleavage was maintained for IR8 with additions of the missense mutations Arg336Iso and Arg562Lys (FIG. 11, lane 14).

Figure 12:
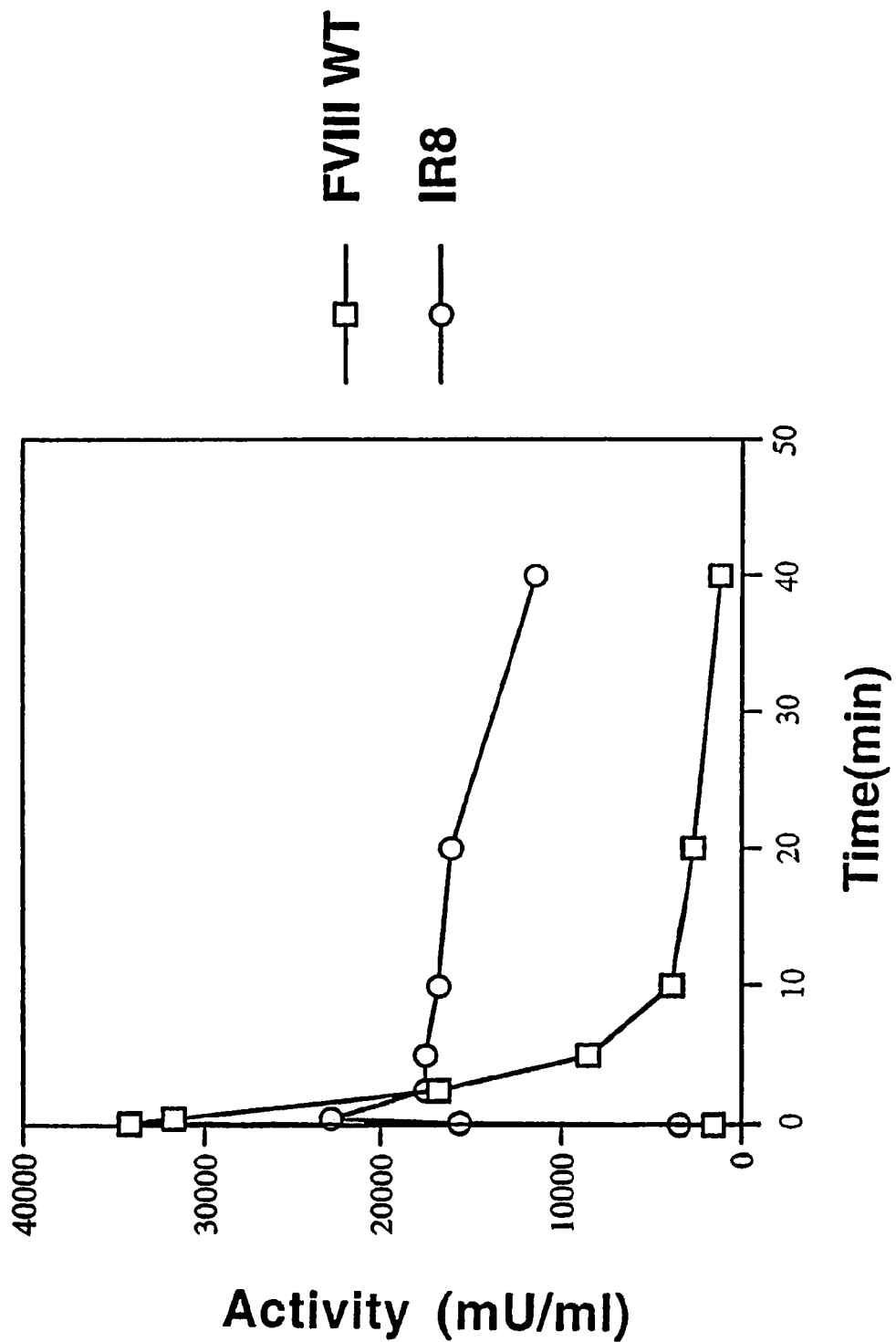
FIG. 12 is a graph showing the functional activation and inactivation of the inactivation resistant FVIII of the present invention as compared to wild-type FVIII.

Functional stability of IR8 following thrombin activation. Having demonstrated the structural integrity of the IR8 heterodimer upon thrombin cleavage, the functional consequence of this modification on activation and inactivation was examined in an in vitro functional assay. Immunoaffinity purified FVIII WT and IR8 were incubated with thrombin and assayed for FVIII activity by a one stage APTT clotting assay. An example of the functional activation and inactivation is depicted in FIG. 12 and is typical of multiple repeat experiments. Under these conditions, FVIII WT was maximally activated within the first 10 seconds of incubation with thrombin, then rapidly inactivated over the next 5 minutes. IR8 did not reach peak activity until 30 seconds incubation with thrombin, suggesting a modestly reduced sensitivity to thrombin activation compared to FVIII WT. In addition, the peak activity for thrombin activated IR8 was lower (74.7+ 6.7% of peak thrombin activated FVIII WT activity, n=3), suggesting some reduced efficiency, as a cofactor. However, IR8 demonstrated significant retention of peak activity over the first 10 minutes of incubation with thrombin (66.9+5.3% of peak IR8 activity, n=3), a period in which FVIII WT was almost completely inactivated. Although there is a gradual loss of peak IR8 activity with prolonged incubation with thrombin, IR8 still retained ~38% of peak activity after 4 hours incubation with thrombin.

Figure 13:
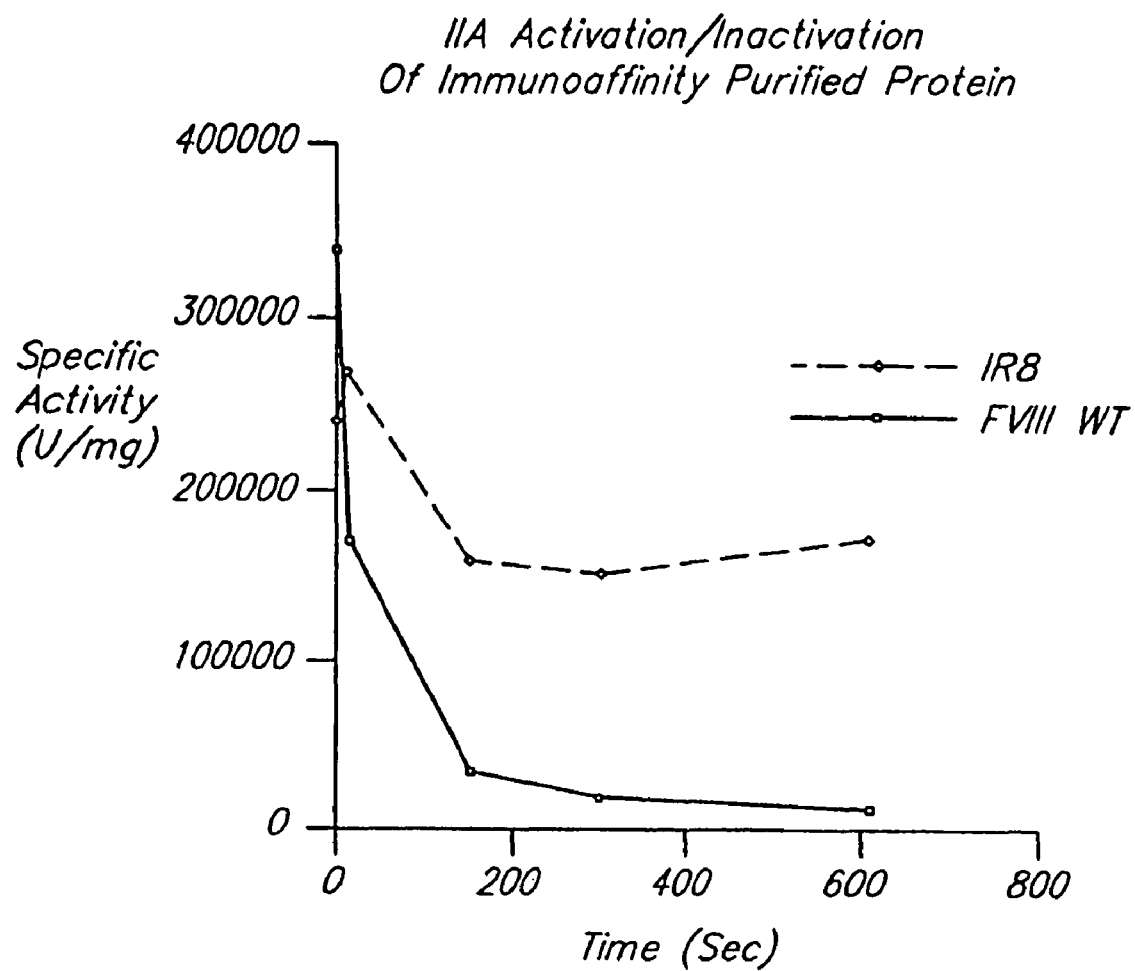
FIG. 13 is a graph showing the activation and reduced rate of inactivation of immunoaffinity purified inactivation resistant FVIII of the present invention as compared to wild-type FVIII.

IR8 demonstrates increased FVIII specific activity in vitro. Immunoaffinity purified FVIII WT and IR8 were assayed for FVIII activity utilizing a standard one stage APTT clotting assay, wherein the first time point was 10 seconds. Antigen determinations were made utilizing a FVIII light chain based ELISA. FIG. 13 shows the activation and reduced rate of inactivation expressed as specific activity. The specific activity values for IR8 were calculated based on a correction for its molecular weight. IR8 was observed to have a 5-fold increased specific activity compared to FVIII WT (102±43 versus 18.6±7.4 U/mg of protein).

EXAMPLE 4

Characterization of the Intramolecular Protein-protein Interactions Stabilizing FVIIIa Instability of FVIIIa Leads to One-stage/Two-stage Activity Discrepancy Experimental Procedures To demonstrate how instability of FVIIIa leads to one-stage/two-stage (1-st/2-st) activity discrepancy, a modification of the chromogenic two-stage assay was used. In particular, an analysis of the proteins with increasing duration of incubation during the first stage of the assay was performed.

Results

Wild-type FVIII continued to generate increasing amounts of FXa throughout 16 minutes of the first stage incubation.

However, the R531H, A284E and S289L could generate no more FXa after 8 and 16 minutes than that observed at 4 minutes, consistent with increased rate of inactivation of the mutant FVIIIa molecules early within the first stage of the assay.

Mutations within A2-A3 Subunit Interface Exhibit One-stage/Two-stage Activity Discrepancy Experimental Procedures Mutations within the predicted A2-A3 subunit interface that exhibit similar 1-st/2-st activity discrepancy were also assessed. Missense mutations N694I, R698L and R698W were expressed within a B-domainless FVIII vector by transient expression in COS-1 cells. Each of the mutations resulted in a secreted protein with 1-st/2-st activity discrepancy similar to that reported from patient plasmas.

Results

Upon thrombin cleavage, purified R698L and R698W proteins exhibited, respectively, twofold and threefold increased rate of A2 subunit dissociation, compared to a B domainless FVIII control, as analyzed in an optical biosensor. Thus, these mutations along the predicted A2-A3 subunit interface exhibit the same molecular mechanism of increased instability of FVIIIa as those mutations described along the A1-A2 interface. This suggests that the entire tightly packed hydrophobic core within the predicted pseudo-threefold axis contributes to stabilization of FVIIIa. Pipe, S. W. et al., *Blood* 97:685-691 (2001) and Pipe, S. W. et al., *Poster presentation at Congress of the International Society on Thrombosis and Haemostasis*, Paris, France, Jul. 6-12 (2001), both of which are incorporated herein by reference.

Stabilization of a Functional Form of FVIIIa by a Strategically Placed Disulfide Bond Experimental Procedures Generation of COS-1 cell lines for in vitro analysis. Cysteine mutations were introduced into each of the following sites: $^{CYS}$282, $^{CYS}$284 and $^{CYS}$531 separately through oligonucleotide-directed mutagenesis and expressed the mutant plasmids in COS-1 cells for in vitro analysis. Each of the mutants were expressed successfully and active. Two complementary cysteine mutations were then introduced into both the A1 and A2 subunits. It is believed that the sulfhydryl groups from either $^{CYS}$282 or $^{CYS}$284 were close enough to potentially form a disulfide bond with the sulfhydryl group of $^{CYS}$531. Standard protein analysis techniques were used to demonstrate the presence of a disulfide bond between the resulting A1 and A2 subunits.

It has been shown that an A2-A3 disulfide bond may be obtained based on a molecular model of the A domains of FVa (Pellequer et al., Thrombosis Haemostatis, 84:849-57 (2000)), indicating that the molecular model could not predict which cysteine mutations would work, as only one successful disulfide bond resulted from several strategies attempted.

Results

Without being bound by theory, it is believed that the introduction of a disulfide bond stabilizes the A2-A3 interaction, and may thereby increase the affinity of A2 with the A1/A3-C1-C2 heterodimer. Cysteine mutations are made at residues predicted to be adjacent in the model and as suggested from studies of the hemophilia point mutations at $^{ASN}$694, $^{ARG}$698 and $^{MET}$1947. Mutation at the A2-A3 interface is thought to have a less disturbing structural effect on the FVIII and enable more efficient expression for detailed analysis.

EXAMPLE 5

Increase of the Plasma Stability of FVIIIa In Vivo

Experimental Procedures

Methods. Three FVIII mutants were prepared in which amino acid(s) were changed to the homologous residues of FV, according to the methods described herein. Mutants were expressed in COS cells and protein purified by immunoaffinity chromatography.

Results

Reduction in specific activity. Mutants M/F 2199/2200 W/W, L/L 2251/2252 L/S (L2252S), and M/F/L 2199/2200/2252 W/W/S had specific activity in the range of 90-180% of wild type FVIII in both 1-stage and 2-stage commercial aPTT assays that contain a large excess of PL. In a PL-limiting Xase assay (sonicated vesicles of PS:PE:PC 4:20:76, 0.15 μM PL) the mutants had >95%, >95%, and 85% reduction, respectively, in specific activity. Phospholipid titration indicated that maximum activity for the mutants occurred at concentrations of 800, 800, and 200 μM versus 1 μM for wild type FVIII. In a Xase assay with saturating PL, 1000 μM, the apparent affinity of factor IXa for the mutants was decreased approximately 4-fold for the three mutants and the maximum catalytic rate decreased by approximately 50, 80, and 50%, respectively. When the PS content of was increased from 4% to 15% PS, all three mutants supported Xase activity within 60% of wild type FVIII although the apparent affinity for factor IXa was reduced 5-fold.

Specific interactions with phospholipid and Factor IXa. Together these results indicate that the hydrophobic spikes composed of M/F 2199/2200 and L/L 2251/2252 have specific interactions with both phospholipid and factor IXa that are distinct from those of the homologous residues of factor V. Equal or increased activity of M/F/L 2199/2200/2252 W/W/S versus either mutant, in which a single hydrophobic pair was altered, suggests that the two hydrophobic pairs may interact cooperatively in the presence of PL and factor IXa. See Gilbert G E, et al. *J. Biol. Chem*., in press (2002); Gilbert, G E, et al. *Oral presentation at the annual meeting of the American Society of Hematology*, Orlando, Fla., Dec. 10, 2001; and Saenko E. L. et al., VOX SANG, in press (2002), all of which are incorporated herein by reference.

EXAMPLE 6

Inducible vWF-binding of Inactivation Resistant Factor VIII

Experimental Procedures

Immulon 2 microtiter wells (Dynatech Laboratories, Inc., Chantilly, Va.) were coated with FVIII antibody at a concentration of 2 ìg/ml overnight at 4° C. in a buffer of 0.05 M sodium carbonate/bicarbonate pH 9.6. Wells were washed with TBST (50 mM Tris HCL/pH 7.6, 150 mM NaCl, 0.05% Tween 20) then blocked with 3% bovine serum albumin (BSA) in TBST. Protein samples were diluted in TBST, 3% BSA, 1% factor VIII-deficient human plasma +/− ESH8 (molar ratio of ESH8:FVIII protein=2:1). Samples were incubated for 2 hours at 37° C. in 1.7 ml microfuge tubes. Samples were then incubated for an additional 2 hours in the blocked and washed microtiter wells. Wells were then washed in TBST containing 10 mM $CaCl_2$. Anti-vWF-HRP antibody was diluted in TBST, 3% BSA, 10 mM $CaCl_2$ and incubated in the wells for 2 hours at 37° C. Following additional washing with TBST containing 10 mM $CaCl_2$, OPD substrate was added to the wells and incubated for 3 minutes. The color reaction was stopped with 2 M $H_2SO_4$ and the optical density (O.D.) read at 490 nm using an EL 340 automated microplate reader (Biotek Instruments Inc., Winooski, Vt.).

Results

Figure 14:
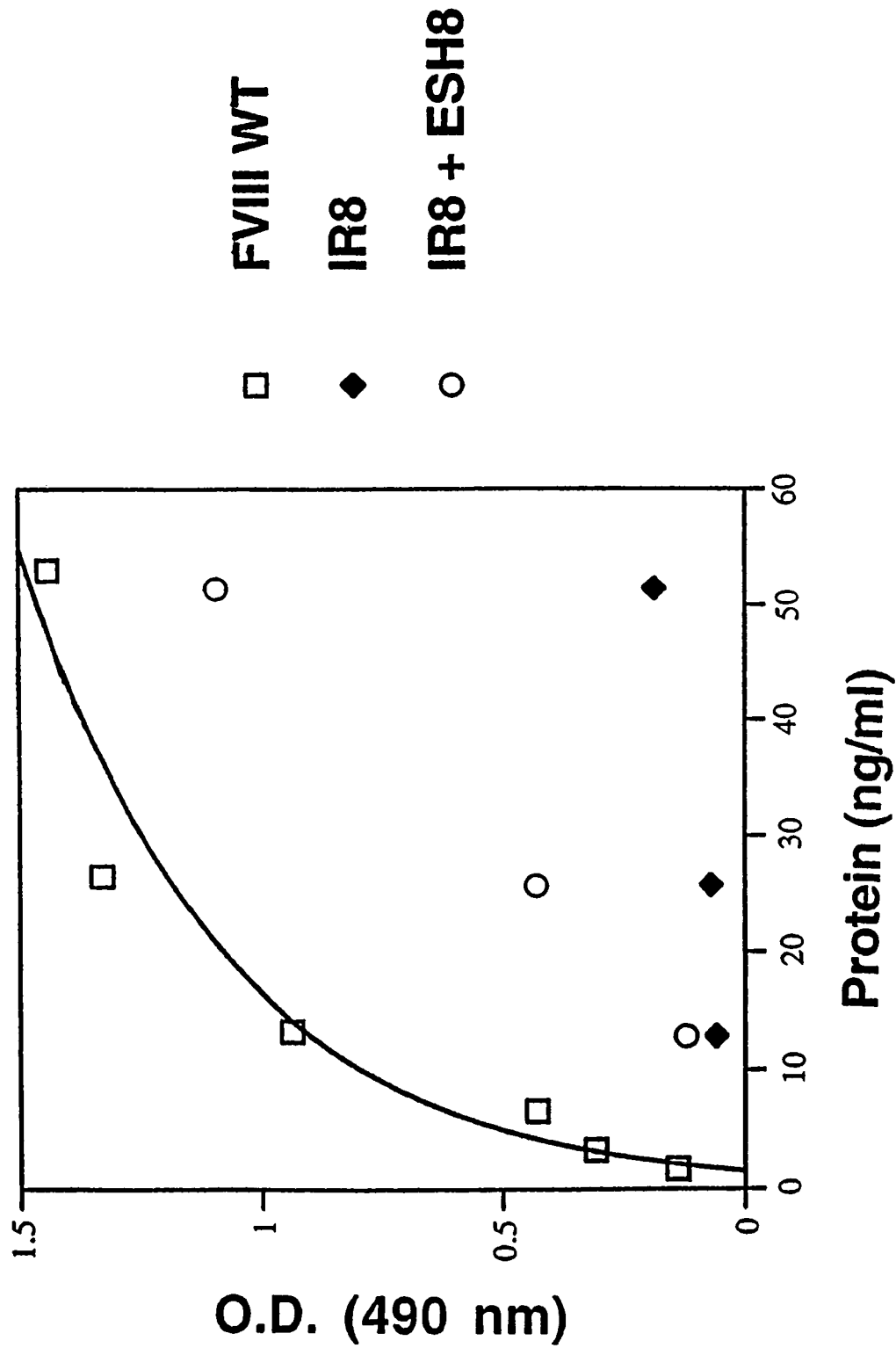
FIG. 14 is a graph illustrating the results of an ELISA assay demonstrating antibody-inducible vWF binding of the inactivation resistant FVIII of the present invention.

FVIII-vWF binding. FIG. 14 shows the results of the FVIII-vWF binding ELISA. An anti-A2 domain trap was used. After a 4 hour incubation with FVIII-deficient plasma (1:100 dilution), binding was detected by perioxidase conjugated anti-vWFab. As shown in FIG. 14, a 10-fold lower binding affinity of IR8 to vWF is observed in the absence of ESH8 compared to wild-type FVIII, and a 2-fold lower binding affinity is observed in the presence of ESH8.

Figure 15:
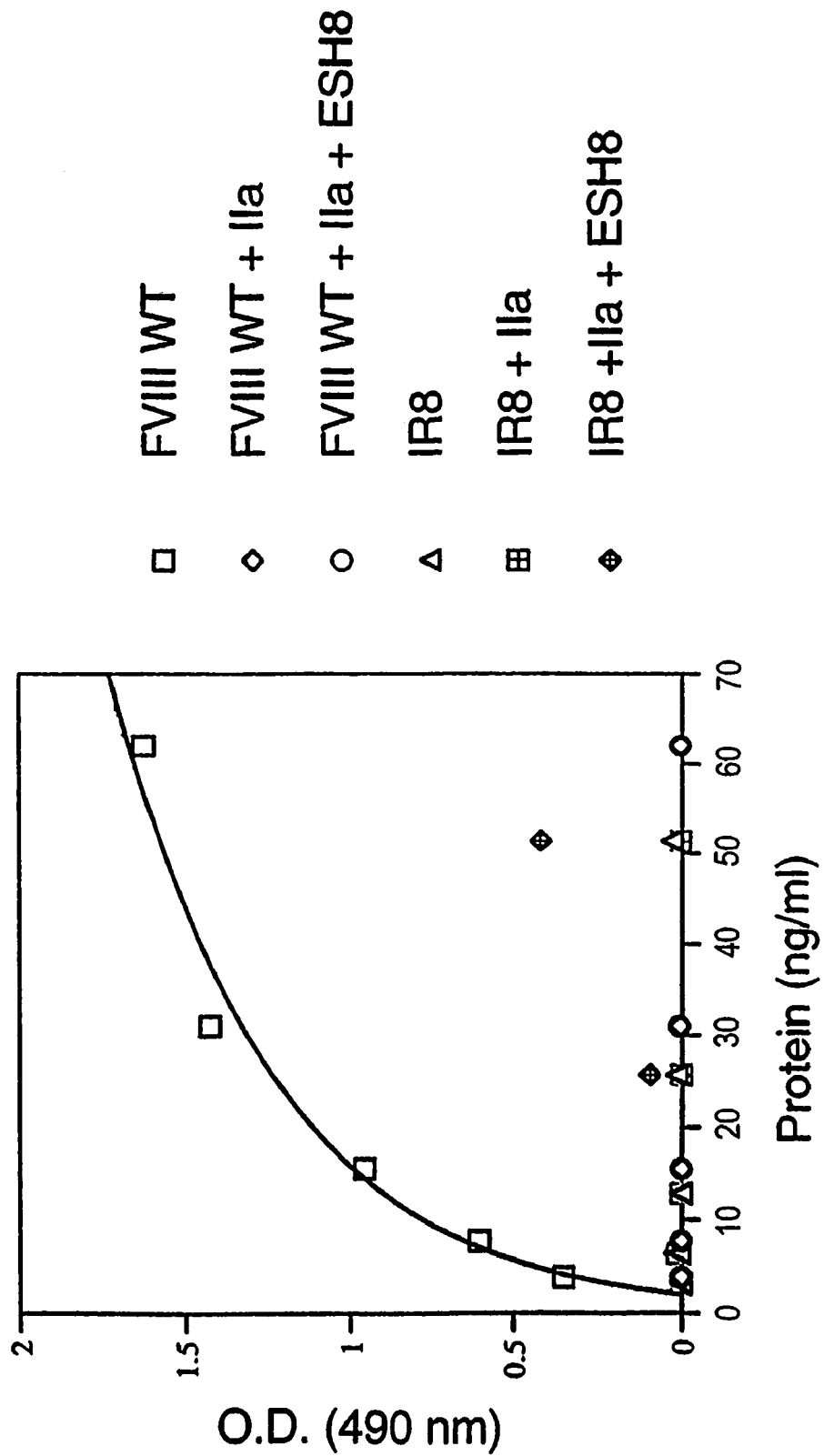
FIG. 15 is a graph illustrating the results of an ELISA assay demonstrating antibody-inducible vWF binding of the inactivation resistant FVIII of the present invention following thrombin activation.

FIG. 15 shows the results of the FVIII-vWF binding ELISA with thrombin (IIa) and/or ESH8. The same ELISA method was used however a 2-fold molar excess of ESH8 was employed as well as a 4 hour incubation with IIa (1 U/ml) in the presence of FVIII deficient plasma. As shown in FIG. 15, IR8 retains activity for vWF after thrombin activation suggesting that the heterodimer is intact after thrombin cleavage and ESH8 stabilizes the light chain confirmation such that it retains some affinity for vWF.

Since the binding assays described above utilize a "trap" antibody that only recognizes the A2-domain of FVIII, it will only detect FVIII-vWF complexes that recognize the A2-domain in association with the rest of the protein. Therefore, following the 4 hour incubation of the protein in the presence of excess thrombin, FVIII wild-type will not only have been fully activated but it will have also have been completely inactivated through A2 dissociation and/or further proteolytic cleavages, and will no longer associate with vWF in a complex that will be recognized by this assay. The inactivation resistant FVIII of the present invention thus retains inducible binding even following complete activation by thrombin.

Figure 16:
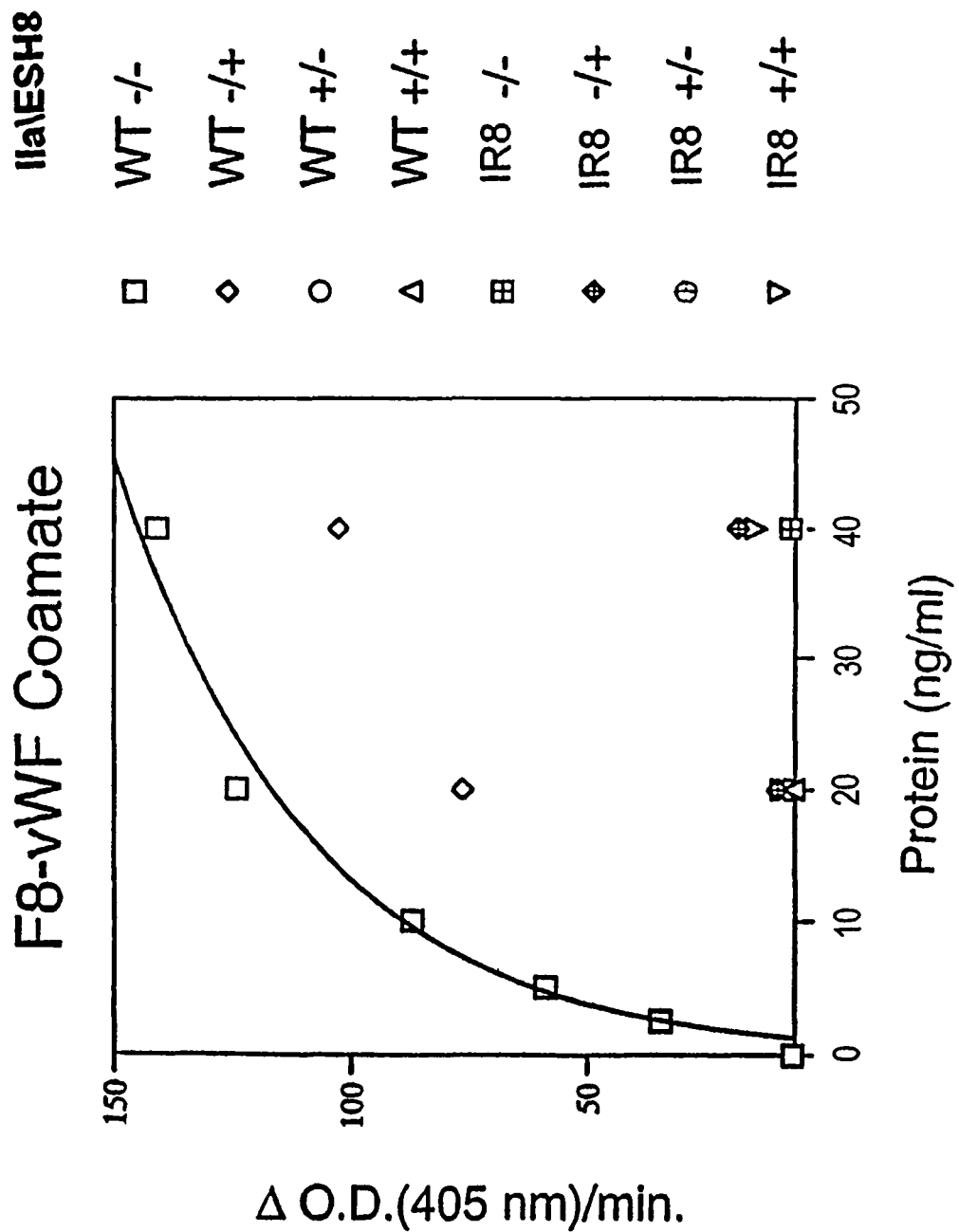
FIG. 16 is a graph illustrating the results of an ELISA assay demonstrating antibody-inducible vWF binding of the inactivation resistant FVIII of the present invention following thrombin activation, and retained FVIII activity.
Figure 17:
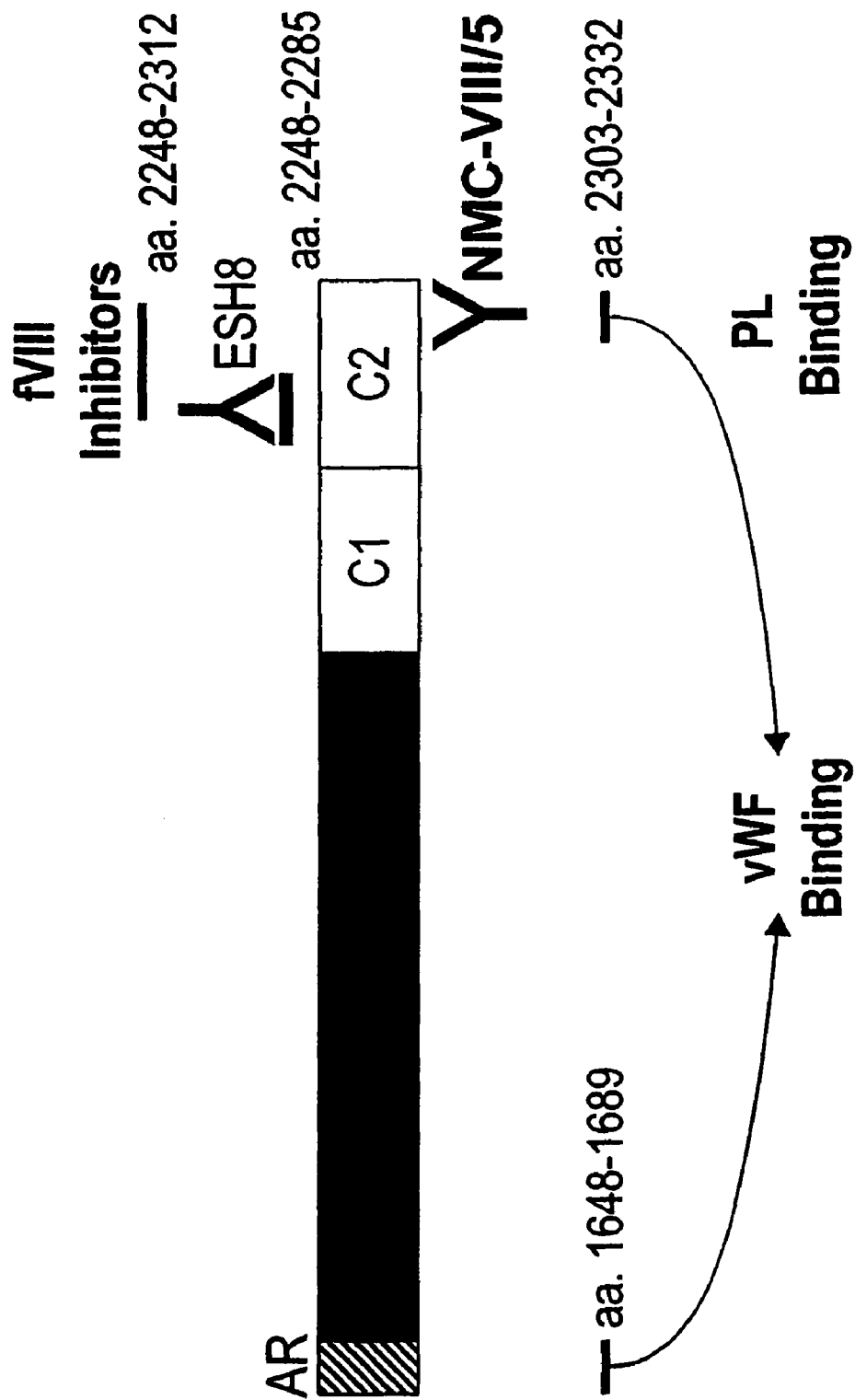
FIG. 17 is a diagram of the FVIII light chain epitopes.
Figure 18:
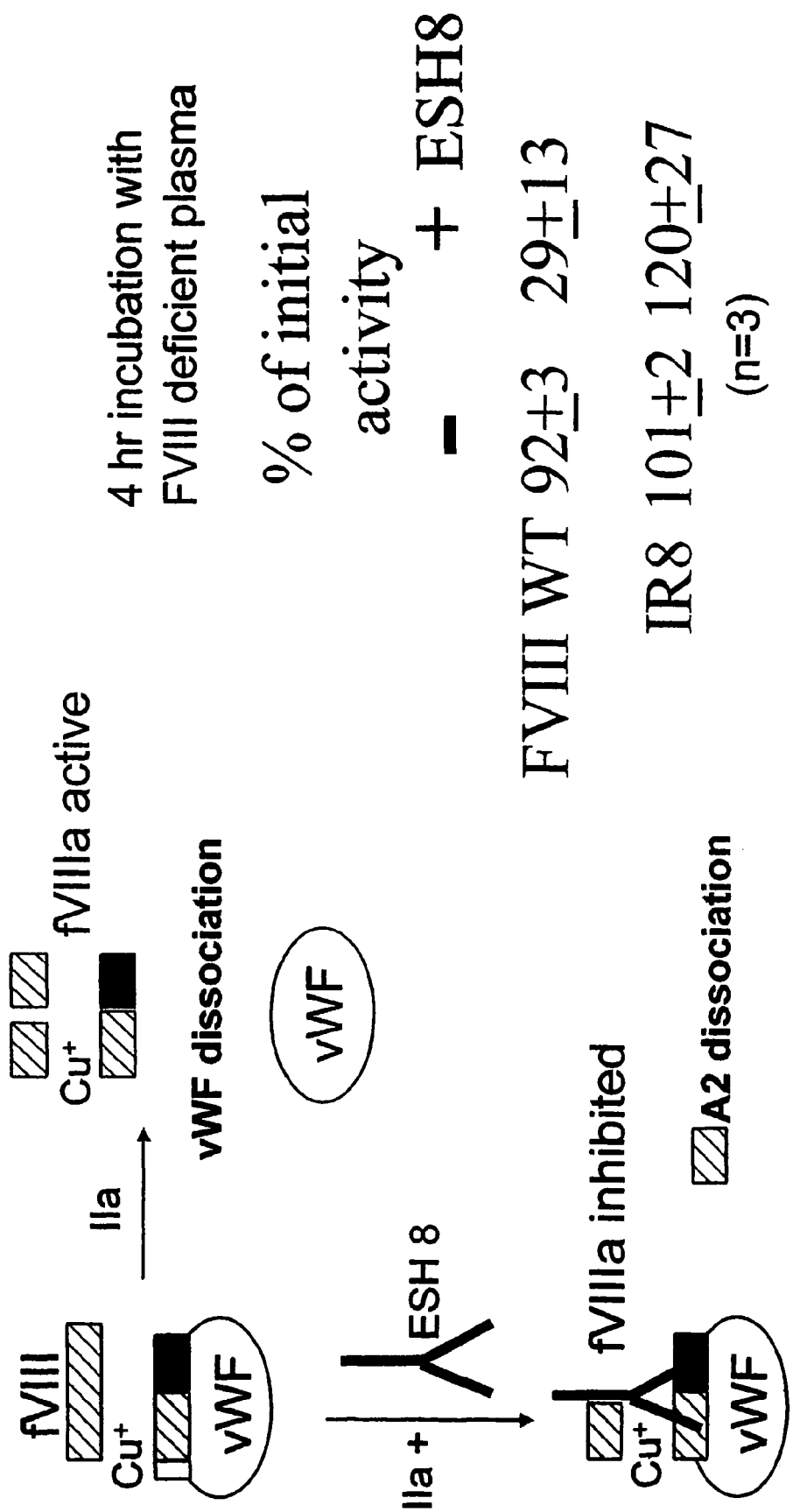
FIG. 18 is a diagram showing that ESH8 does not inhibit inactivation resistant FVIII activity in the presence of vWF.

It was also shown that the inducible vWF-binding form of the inactivation resistant FVIII of the present invention retained activity. In this assay, an anti-vWF antibody was used as the "trap" for the ELISA. The same incubation was performed in the presence and absence of thrombin and ESH8. Following immobilization of the FVIII-vWF complex on the plate, FVIII activity was measured using a chromogenic FVIII assay kit (Coamatic, Pharmacia Hepar, Franklin, Ohio.) within the ELISA wells. As shown in FIG. 16, following activation by thrombin, no demonstrably active FVIII-vWF complexes were observed for FVIII wild-type. However, the inactivation resistant FVIII still had detectable activity under the same conditions. This suggests that following thrombin activation, the inactivation resistant FVIII is cleaved to a heterodimer of A1 in association with a modified light chain of A2-b-A3-C1-C2 that has ESH8-inducible binding to vWF, and retains FVIII activity.

The functional impact of this ESH8-induced IR8-vWF complex was also evaluated by assaying for FVIII activity via APTT (Table 3). In the absence of ESH8, immunoaffinity purified FVIII WT and IR8 demonstrated minimal loss of activity over a 4 hour incubation at 37° C. with FVIII-deficient plasma. In the presence of ESH8, FVIII WT activity was inhibited by approximately 70%, whereas IR8 retained 100% of its initial activity. These results suggest that inactivation of WT FVIII in the presence of ESH8 may be due to A2 subunit dissociation and IR8 is resistant to inactivation by ESH8 because it is not susceptible to A2 subunit dissociation.

TABLE 3

ESH8 Does Not Inhibit IR8 Activity In Presence Of vWF

| Protein | % Of Initial Activity | |
|---|---|---|
| | −ESH8 | +ESH8 |
| FVIII WT | 92 ± 3 | 29 ± 13 |
| IR8 | 101 ± 2 | 120 ± 27 |

EXAMPLE 7

Affinity and Activity of IR8

Figure 22:
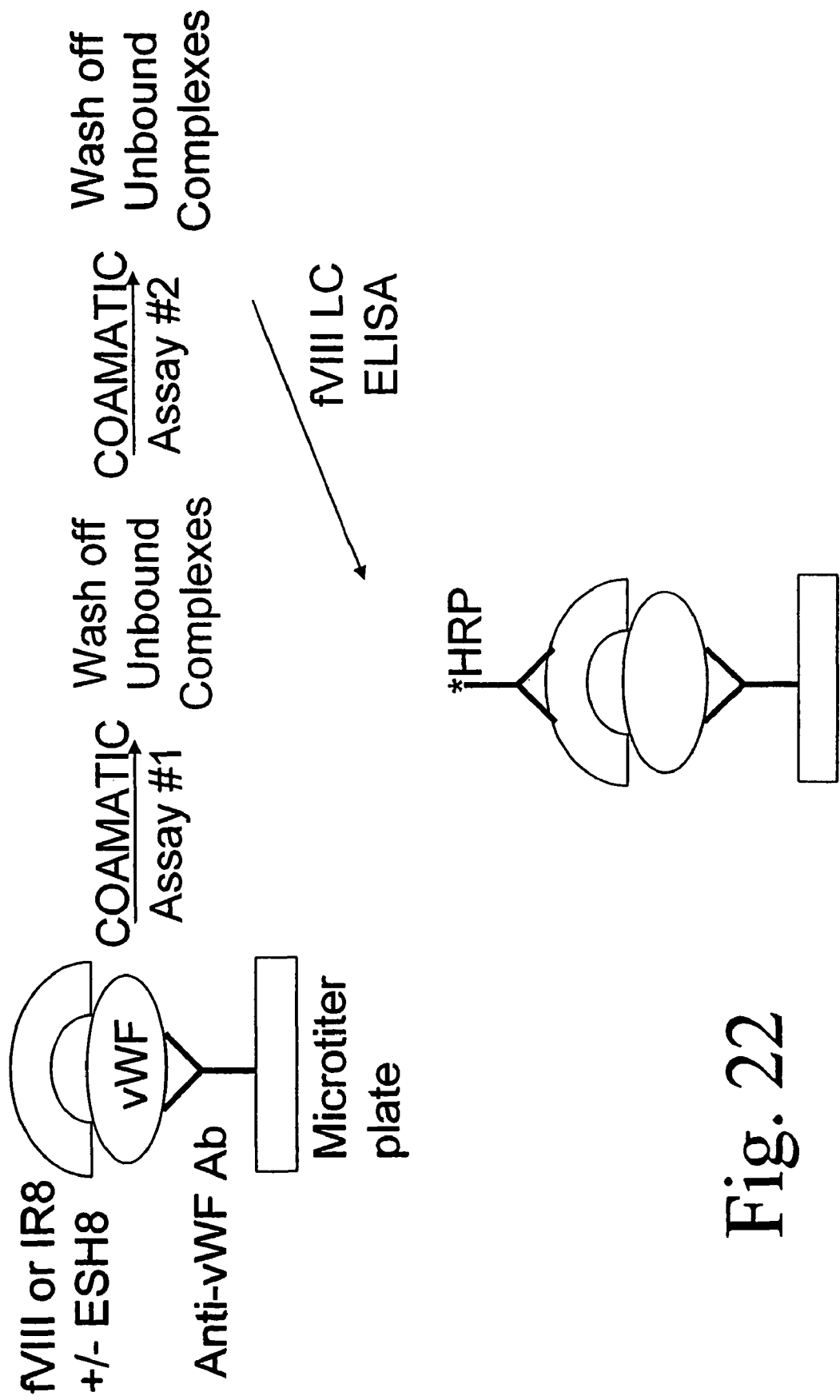
FIG. 22 depicts the activity of bound FVIII-vWF complexes with and without ESH8.
Figure 24B:
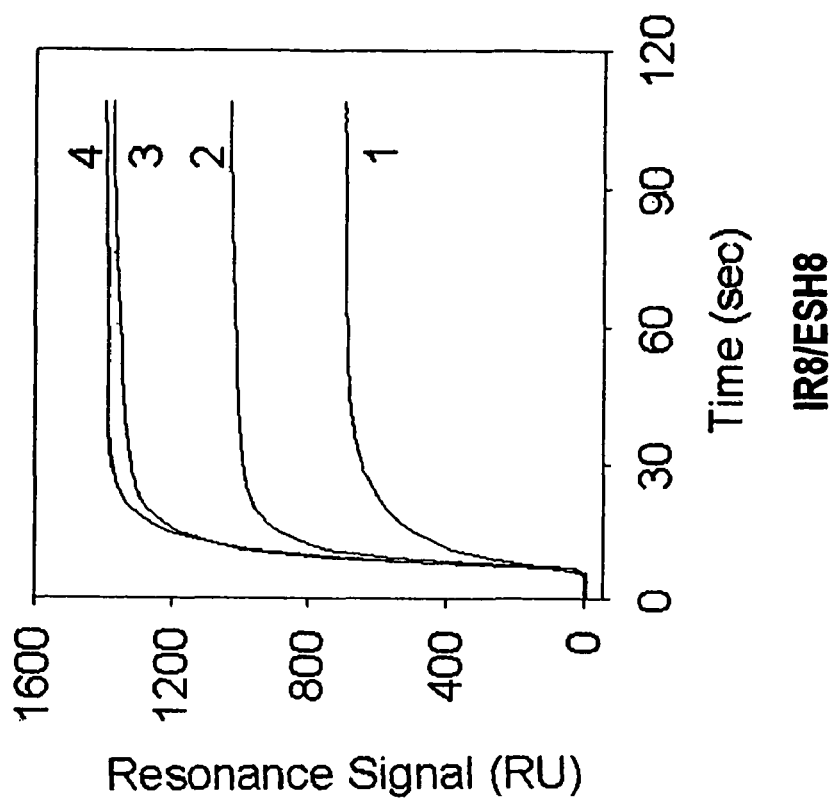
FIGS. 24A and 24B are graphs illustrating that increasing concentrations of vWF does not inhibit binding of inactivation resistant FVIII/ESH8 complexes to phospholipids.
Figure 24A:
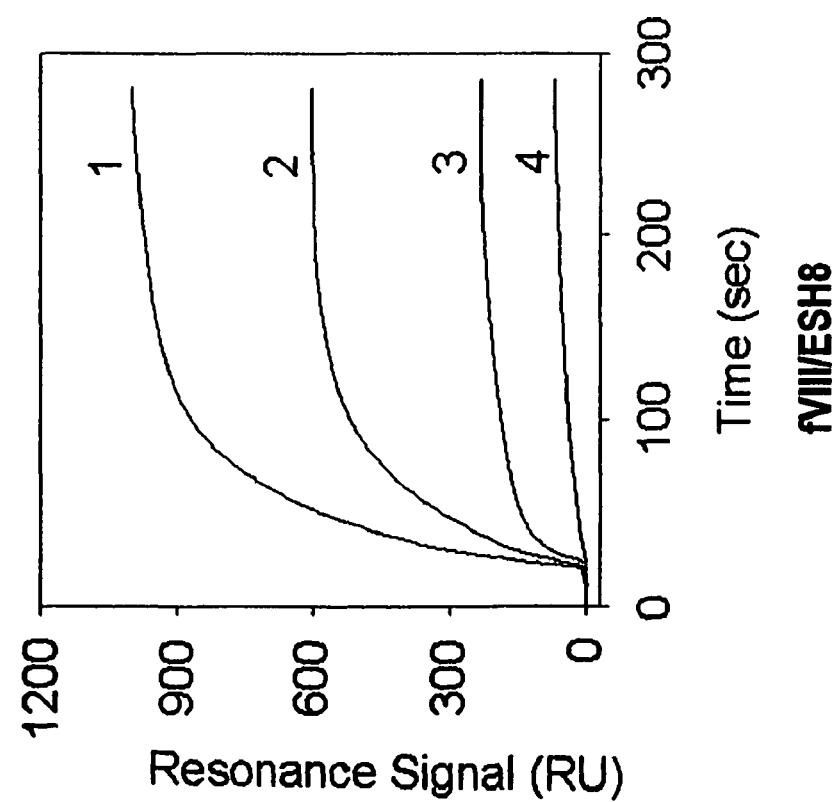

IR8 Affinity for von Willebrand factor and phospholipid. ELISA and affinity biosensor analysis demonstrated IR8 had a 20-fold reduced affinity for von Willebrand factor (vWF), but a 34-fold increased affinity for phospholipid (PL) compared to rFVIII. These changes were attributed to deletion of the AR. In contrast to wild-type FVIII, these affinities were not changed upon thrombin activation of IR8. The monoclonal antibody ESH8 increases the affinity of the thrombin-cleaved FVIII LC to vWF by preventing a LC conformational change that follows proteolytic removal of the AR in vitro (FIG. 22).

Figure 19:
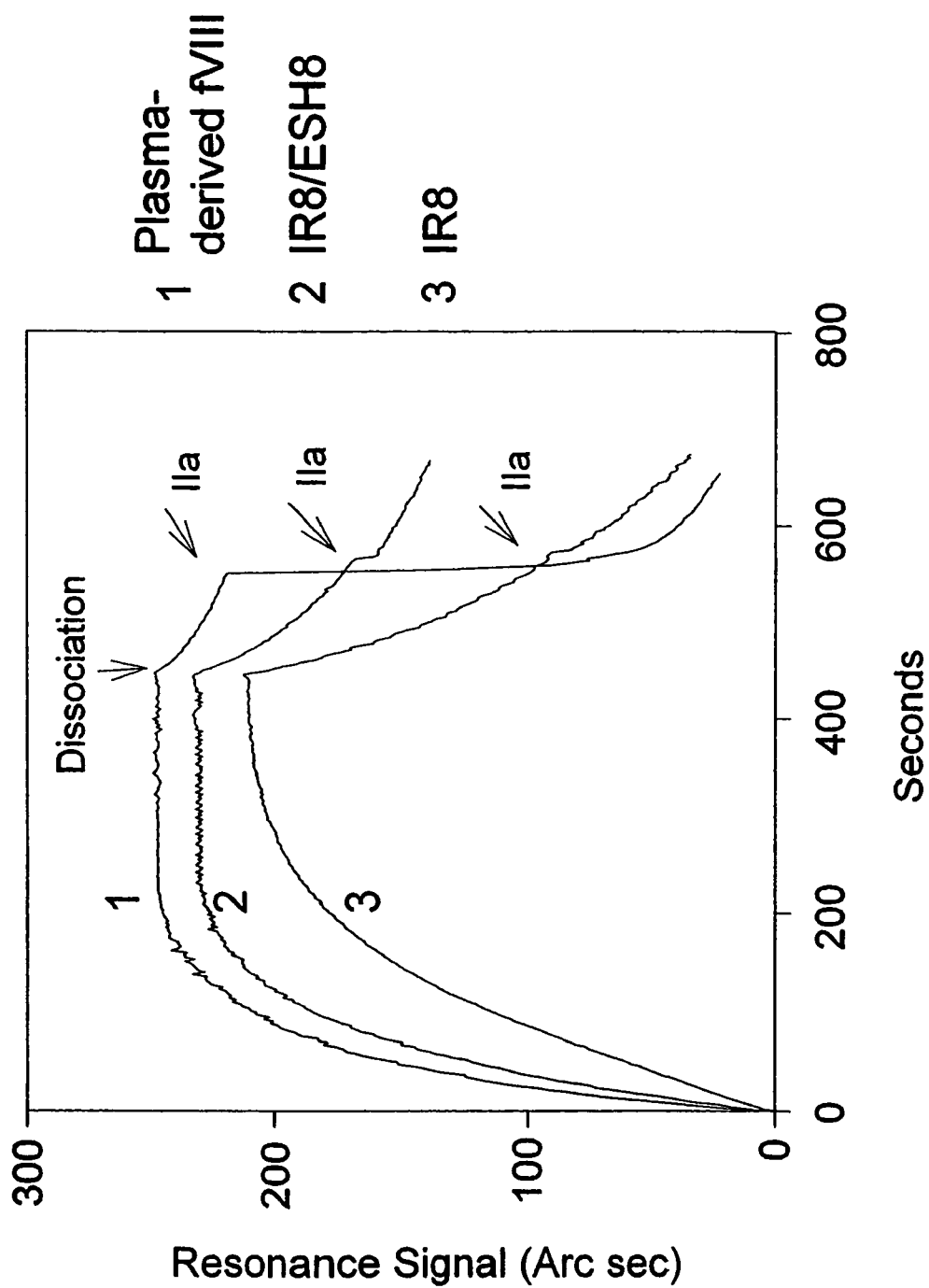
FIG. 19 is a graph illustrating that thrombin activation of inactivation resistant FVIII/ESH8 does not alter vWF dissociation.

It was proposed that ESH8 inhibits FVIII activity in vitro by reducing the rate of vWF dissociation from FVIII upon thrombin activation. However, a complex of IR8/ESH8 demonstrated increased affinity for vWF in vitro (IR8 versus rFVIII, $K_d$=1.3 nM versus 0.3 nM), while retaining full activity bound to vWF. Anti-FVIII antibodies specific for the PL binding site were still able to bind, suggesting that the PL binding site and the vWF binding site do not overlap within this LC conformation. Moreover, in contrast to FVIII WT, thrombin activation of IR8/ESH8 does not alter vWF dissociation (FIG. 19).

Figure 20:
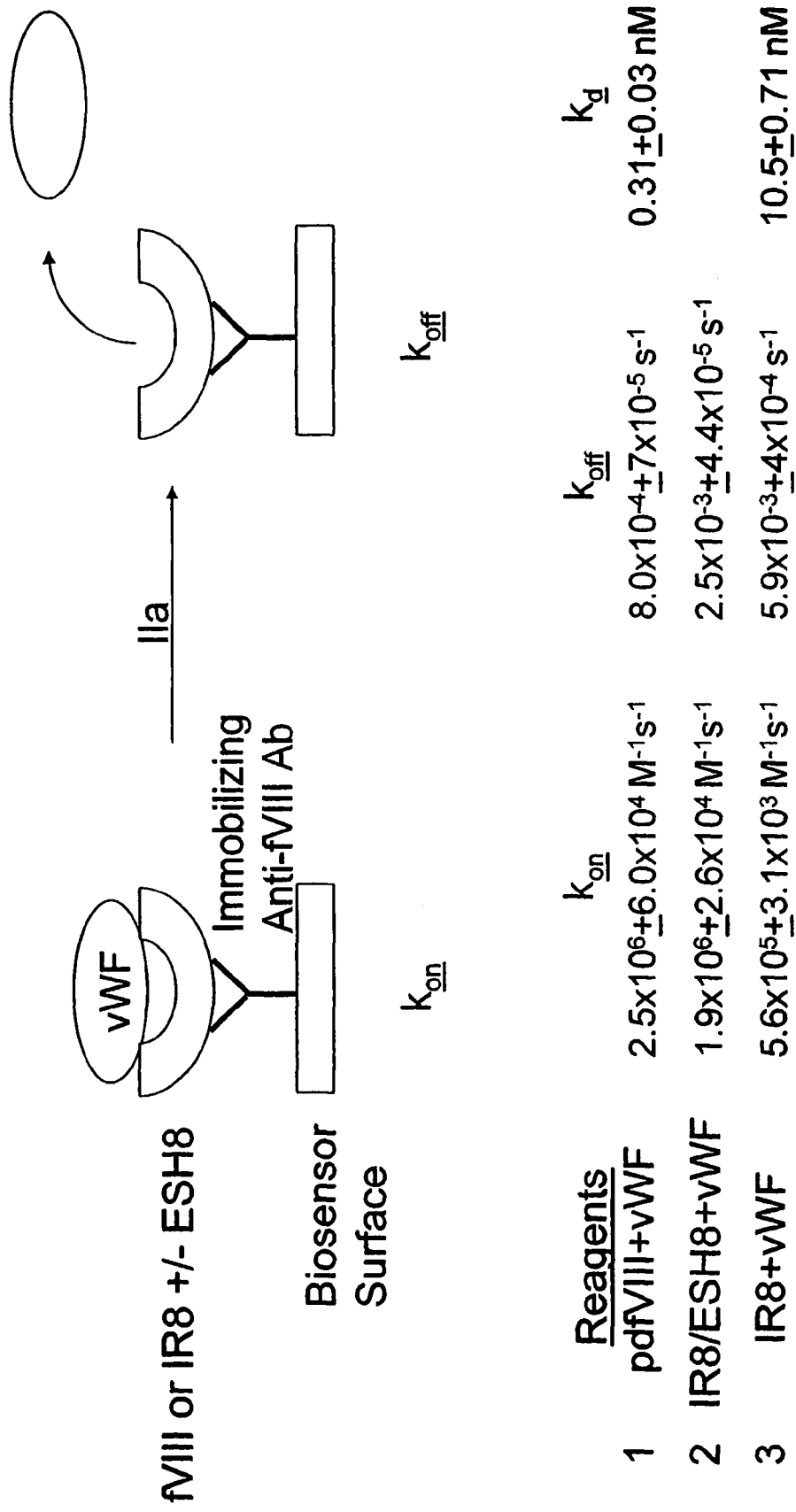
FIG. 20 depicts the kinetics of inactivation resistant FVIII-vWF association and dissociation.
Figure 21A:
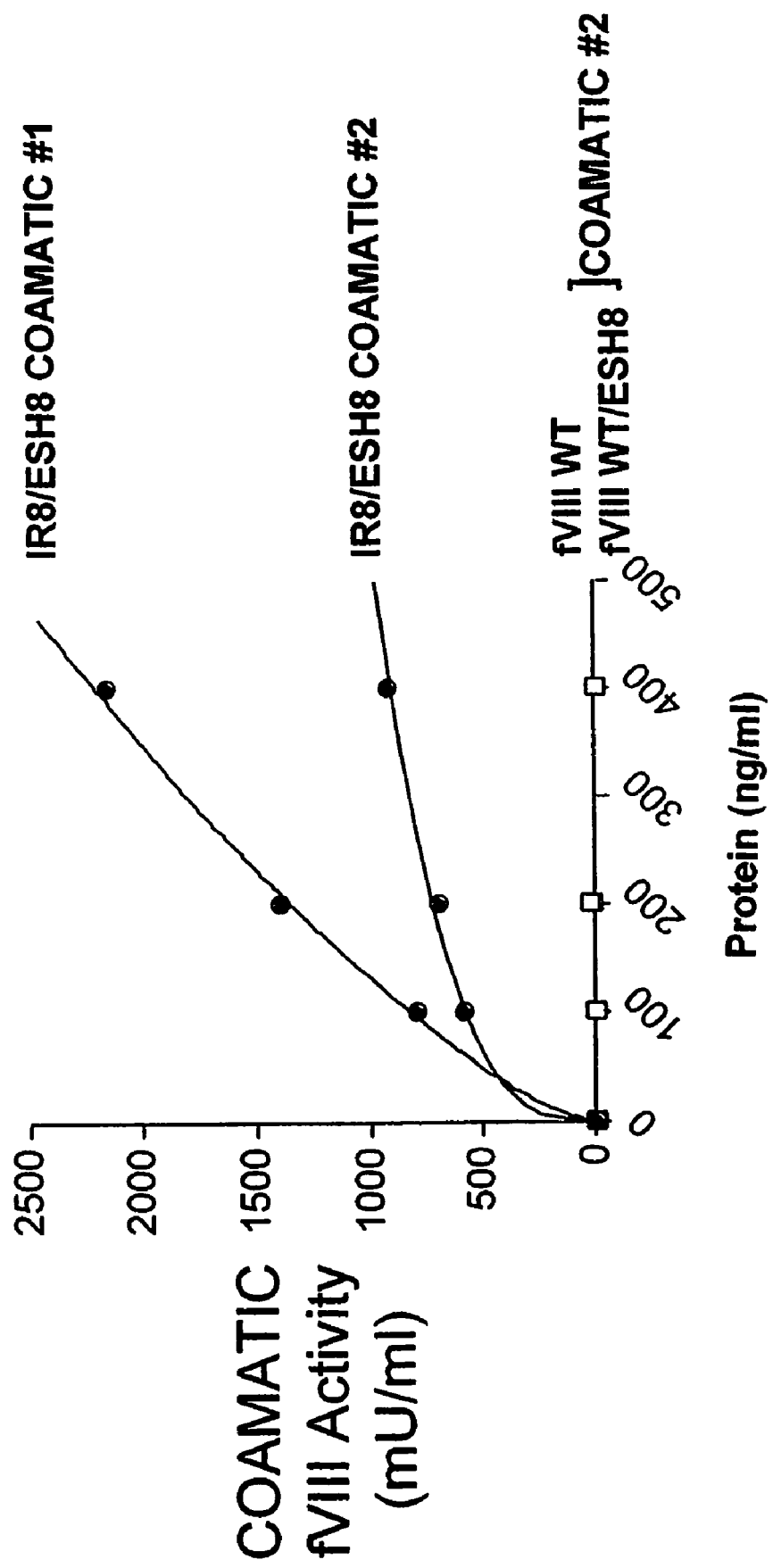
FIGS. 21A and 21B depict the kinetics of thrombin activation.
Figure 21B:
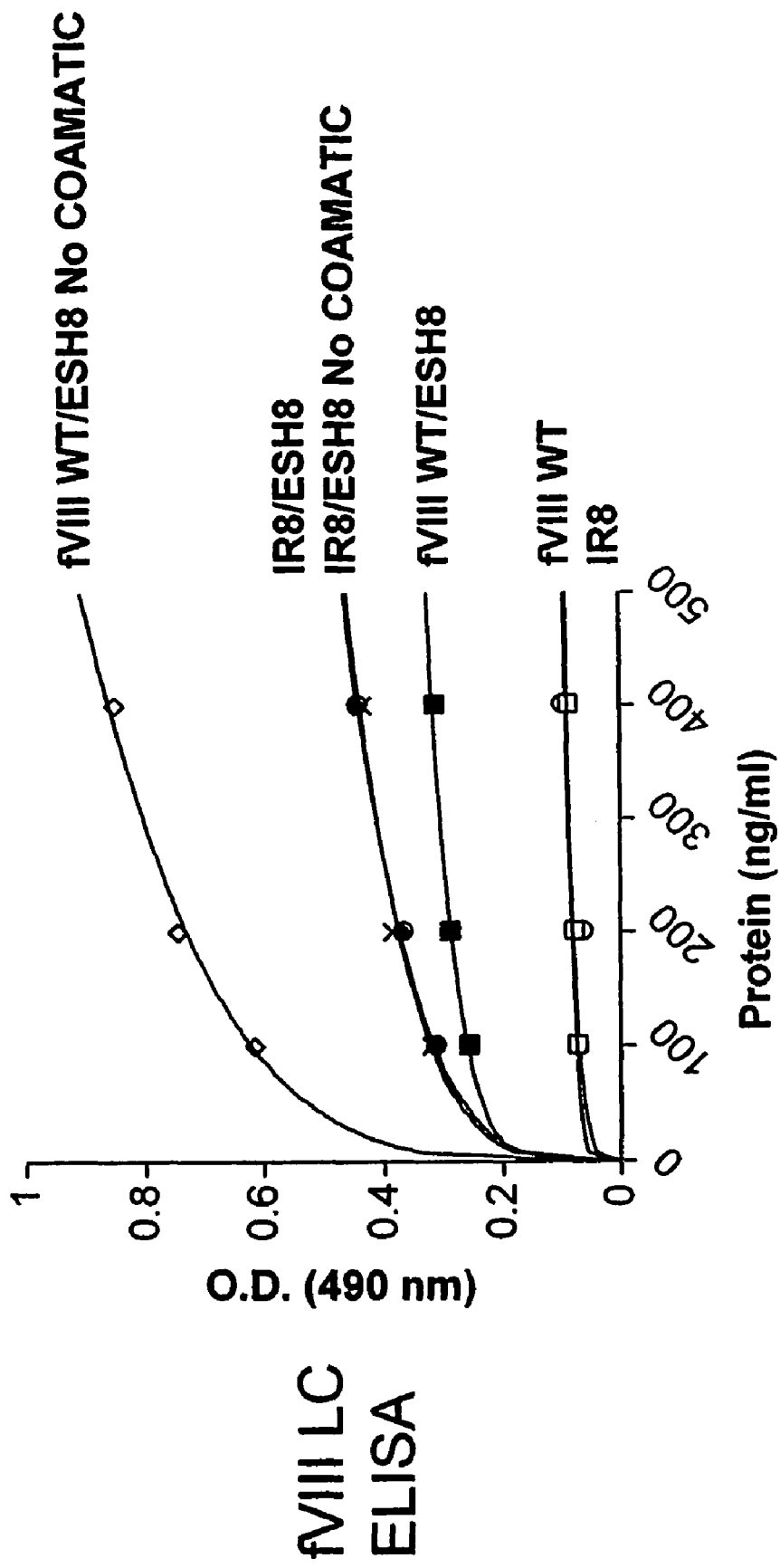

Kinetics of IR8 and vWF. The kinetics of IR8-vWF association and dissociation are set forth in FIG. 20. The kinetics of thrombin activation of IR8 shows a loss of activity within the first 30 seconds and then remains stable at approximately 40% of peak activity for several hours (Pipe, S. W. et al., PNAS (USA) 94(22):11851-6 (1997)). The difference in the activity of IR8 between COAMATIC #1 and #2 is consistent with this observation (FIG. 21). The post-COAMATIC ELISA confirms that IR8/ESH8 is retained in complex with vWF throughout the assay. Because the ELISA detects LC, FVIII/ESH8 is detected partially complexed with vWF in an inactive form, which may be due to A2 subunit dissociation or the PL binding site is blocked while the FVIII LC is bound to vWF.

Although the affinity of IR8 for vWF is greater than 10-fold lower than FVIII WT, ESH8 induces an IR8-vWF interaction similar to FVIII WT that does not change upon thrombin activation. These results suggest that ESH8 induces a conformation of the LC that retains high affinity for vWF that is independent of the presence of the AR. Without being bound by theory, the AR may be responsible for regulating FVIII cofactor activity as the presence of the AR induces a high affinity vWF binding LC conformation and blocks that PL binding site and the absence of the AR results in a LC conformation that has low affinity for vWF thus the PL binding site is not blocked.

IR8-vWF Interaction is not Blocked by Mab NMC-VIII/5

Experimental Procedures 30 nM of IR8 or FVIII WT were added to Mab NMC-VIII/5 immobilized at 10 ng/mm². Following immobilization, the ligand was replaced by buffer at the first arrow and then after 30 sec, vWF was added (first arrow) at 10 nM (FIG. 23).

Results

No signal was observed for vWF binding to immobilized FVIII WT, indicating NMC-VIII/5 completely blocks the vWF binding site. In contrast, vWF binds to IR8 captured on NMC-VIII/5 ($k_{on}=1.4\times10^5$ $M^{-1}s^{-1}$, $k_{off}=4.2\times10^{-3}s^{-1}$, $k_d=29.6$ nM). At the second arrow, dissociation of vWF from IR8 was initiated (FIG. 23). The rate of spontaneous dissociation of IR8 or FVIII WT from NMC-VIII/5 is negligible (FIG. 23).

Increased Concentrations of vWF does not Inhibit Binding of IR8/ESH8 Complexes to Phospholipids Experimental Procedures SPIII is a 340 kDa homodimeric disulfide-linked vWF fragment (residues 1-1365 of vWF) and has affinity for FVIII similar to intact vWF. Saenko, E. L. et al., *J. Biol. Chem.* 270:13826-13833 (1995). The effect of the increasing concentrations of SPIII (no SPIII in curve 1, 10 nM SPIII in curve 2, 25 nM SPIII in curve 3, 50 nM SPIII in curve 4) on binding of FVIII/ESH8 complex to PSPC monolayer is set forth in FIG. 24.

Results

The increasing concentrations of SPIII progressively inhibited binding of FVIII/ESH8 (10 nM) to PSPC (FIG. 24, Panel A). The effect of SPIII was similar to that of vWF added at the same concentration (assuming a molecular weight of 270 kDa per vWF monomer). In contrast, preincubation (30 min, room temperature, HBS, 5 mM $CaCl_2$) of IR8/ESH8 (3.2 nM) with the increasing concentrations of SPIII fragment lead to increase of the plasmon resonance signal observed when the mixture was added to the PSPC monolayer (FIG. 24, Panel B). Upon increase of SPIII concentration (to 50 nM) the signal increased saturation at the level approximately 2-fold greater than that in the absence of SPIII. This is consistent with formation of the IR8/ESH8/SPIII complex (1:1:1) which binds to the PSPC monolayer.

Determination of the Binding Affinity of IR8/ESH8/SPIII Complex to Phospholipids Experimental Procedures Preparation of the IR8/ESH8/SPIII complex. The IR8/ESH8/SPIII complex was prepared by incubation (30 min, RT) of 200 nM SPIII, 200 nM ESH8 with varying concentrations of IR8 (0.1 nM-6.4 nM). Association of IR8/ESH8/SPIII with PSPC (25/75) was measured in HBS, 5 mM $CaCl_2$ until equilibrium was approached. The concentration of the IR8/ESH8/SPIII complex corresponding to curves 1-8 are 0, 0.1, 0.2, 0.4, 0.8, 1.6, 3.2 and 6.4 nM, respectively (FIG. 25, Panel A).

$K_d$ value. Determination of the $K_d$ value for IR8/ESH8/SPIII binding to PSPC monolayer is set forth in Panel B of FIG. 25. The open symbols are the values of equilibrium binding ($B_e$) determined from curves 1-7. The solid line shows the best fit of the $B_e$ values to the equation: $R_e=R_{max}F/(K_d+F)$, describing equilibrium binding. In the equation, F is the concentration of unbound ligand, $R_{max}$–maximal binding capacity of the PSPC monolayer.

Results

The $K_d$ value determined for binding of IR8/ESH8/SPIII complex to PSPC monolayer is 0.286±0.022 nM and similar to that for IR8/ESH8 binding to PSPC (0.242 nM), indicating that SPIII does not significantly affect affinity of IR8/ESH8 for PSPC.

EXAMPLE 8

Plasma Pharmacokinetics and Efficacy of IR8 and IR8/ESH8 Complex in Animals

Methods in Use

The plasma pharmacokinetics and efficacy of IR8 and IR8/ESH8 complex ere evaluated in the Chapel Hill strain of hemophilia A dogs. IR8 protein was produced in Chinese hamster ovary cells and compared to rFVIII (Baxter).

Experimental Procedures

Hemophilia A dogs were infused with either IR8 or recombinant FVIII (35 units/kg iv) with and without Mab ESH8. Both IR8 and rFVIII corrected the whole blood clotting time (WBCT) to the normal range. A 32% recovery was detected for rFVIII and 11% for IR8. The plasma half-life was reduced for IR8 compared to rFVIII (2 h versus 7 h). Both the reduced recovery and short half-life of IR8 relative to rFVIII are consistent with the reduced vWF-binding affinity of IR8.

To determine if enhancing the ability of IR8 to complex with vWF would improve its recovery or lengthen the circulating half-life, both IR8 and rFVIII were mixed with the Mab ESH8 at a protein concentration four times greater than the coagulant protein. In the presence of ESH8, the plasma recovery of FVIII WT following infusion was reduced (16%); however, the half-life of clearance was unchanged consistent with inhibition of FVIII WT activity by ESH8 similar to in vitro results (FIG. 26). In contrast, the half-life of IR8 was doubled to 4 hours in the presence of IR8 with no reduction in the plasma recovery, consistent with stabilization in the plasma through increased binding to vWF, but no inhibition of cofactor activity (FIG. 26).

Significantly, IR8 corrected the secondary cuticle bleeding time in the hemophilia A dogs to the normal range in both the presence and absence of ESH8 showing no inhibition of cofactor activity in vivo.

Results

Plasma recovery and clearance were monitored by COAMATIC assay, whole blood clotting times, and ELISA. Plasma recovery of IR8 was reduced (11% versus 32%) and the plasma half-life ($t_{1/2}$) was significantly shorter (2 h versus 7 h) than rFVIII. These results are consistent with a lack of vWF binding to IR8 in vivo and are comparable to the $t_{1/2}$ of FVIII infused into patients with vWF deficiency. Despite this, IR8 was still able to correct the cuticle bleeding time (CBT), similar to rFVIII. IR8/ESH8 complex was prepared by incubating purified IR8 with a 4-fold excess of ESH8. The recovery of IR8 in this complex measured by activity and ELISA assay was still reduced at 11% but the plasma $t_{1/2}$ was doubled to 4 hours consistent with increased stabilization through binding to vWF. The IR8/ESH8 complex also corrected the CBT, indicating that IR8/ESH/vWF complex may be active in vivo.

Figure 26B:
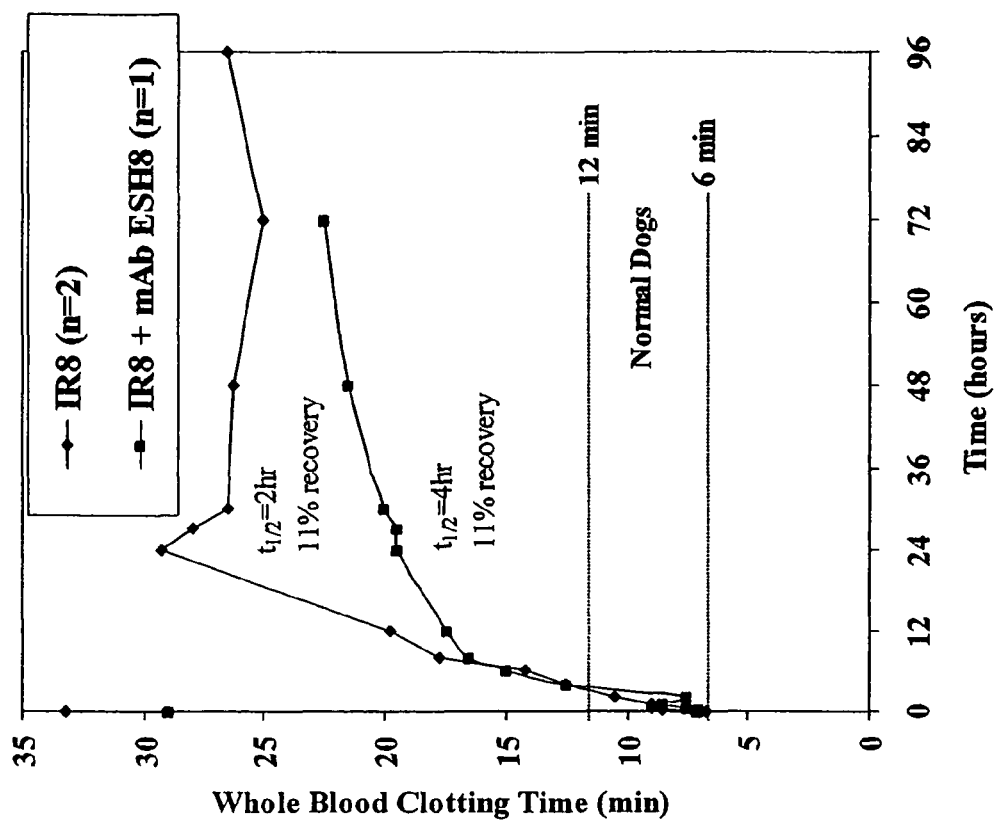
FIGS. 26A and 26B are graphs illustrating that ESH8 increases the half-life of inactivation resistant FVIII in vivo, but in contrast to FVIII WT, does not inhibit activity.
Figure 26A:
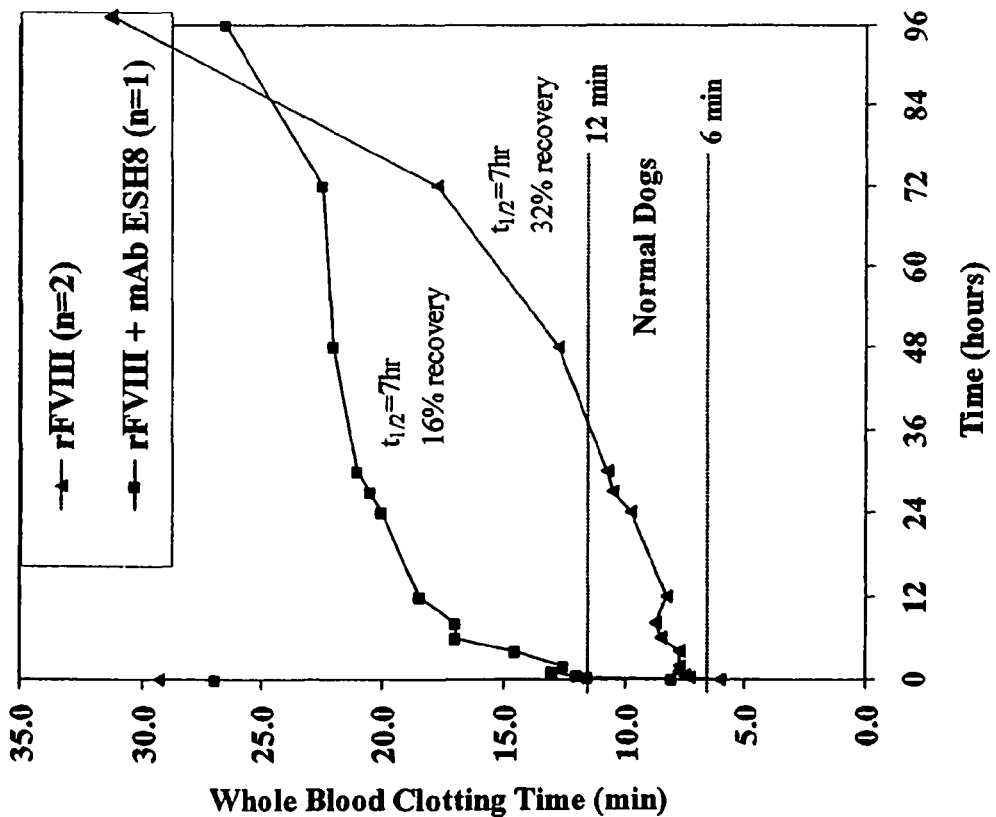

These results are consistent with ESH8 inducing a LC vWF-binding conformation within IR8 that is similar to intact FVIII LC. However, in sharp contrast to rFVIII, this IR8 LC conformation allows simultaneous high affinity PL binding and does not interfere with cofactor activity (FIG. 26).

In summary, upon removal of the AR, there is a FVIII LC conformation that retains high vWF and PL binding affinity (FIG. 27). The results also demonstrate that the vWF and PL binding sites are not overlapping and competitive in all FVIII LC conformations. The IR8/ESH8 complex has a unique LC confirmation that retains both high affinity vWF and PL affinity. Moreover, the IR/ESH8/vWF complex is stable and active both in vitro and in vivo.

EXAMPLE 9

FVIII B Domain Mutants Show Increased Secretion Proportionate to Their N-linked Oligosaccharide Content Experimental Procedures Preparation of FVIII mutants. FVIII wild-type (intact B domain) and a full B domain-deletion molecule were used as controls. Since FVIII is stabilized in conditioned medium through binding to vWF, all of the FVIII mutants were initially prepared within a BDD-FVIII vector that has no light chain acidic region (90/73) and therefore markedly reduced affinity for vWF. Thus, any improvement in FVIII recovered from the conditioned medium could be more easily attributed to increased rate of secretion. Increasing lengths of B domain sequences were introduced into 90/73 that all started with amino acid (aa) residue 741 of FVIII. Each incremental increase in the size of the B domain included one additional N-linked glycosylation site. The resultant proteins were expressed by transient transfection in COS-1 cells. The relative rates of secretion were determined by FVIII ELISA of the conditioned medium collected from 36 to 60 hours post-transfection.

The N-linked glycosylation sites were then mutated (to glutamine) within the 117 amino acid B domain containing construct (which has 3 putative N-linked oligosaccharides), and the relative rates of secretion were determined as before. This experiment was also repeated with constructs that contained the LC acidic region. Because vWF is limited in serum-containing medium, the same experiment was performed by co-transfection of a vWF expression vector along with the FVIII mutants.

Results

Increased secretion. All expressed proteins were synthesized efficiently and retained high specific activity that was comparable to their relative secretion. Average secretion of 90/73 was 7.9 ng/ml and that of FVIII wild-type was 62 ng/ml. Increasing segments from the amino-terminal end of the B domain improved FVIII secretion as follows: 29 amino acids, 1.7-fold; 54 amino acids, 3.4-fold; 117 amino acids, 5.3-fold; 163 amino acids, 8.5-fold; and 226 amino acids, 10.8-fold (see FIG. 28). Thus, with increasing size of the B domain, and therefore, the number of glycosylation sites, there was an ~10-fold increased secretion.

Compared to the native 117 amino acid B domain construct (5.3-fold increased secretion compared to 90/73), mutation of one N-linked site reduced secretion to 4.5-fold and mutation of 2 N-linked sites reduced secretion to 2.4-fold. Therefore, despite no change in the size of the B domain spacer, decreased oligosaccharide content reduced secretion. When this experiment was repeated with constructs that contained the LC acidic region, a blunted response was observed with only a 2-3 fold increase in secretion. Therefore, the same experiment was performed by co-transfection of a vWF expression vector along with the FVIII mutants. The results demonstrated a similar pattern of increasing FVIII activity up to 10-fold recovered from the medium as the number of N-linked glycosylation sites increased.

Figure 29:
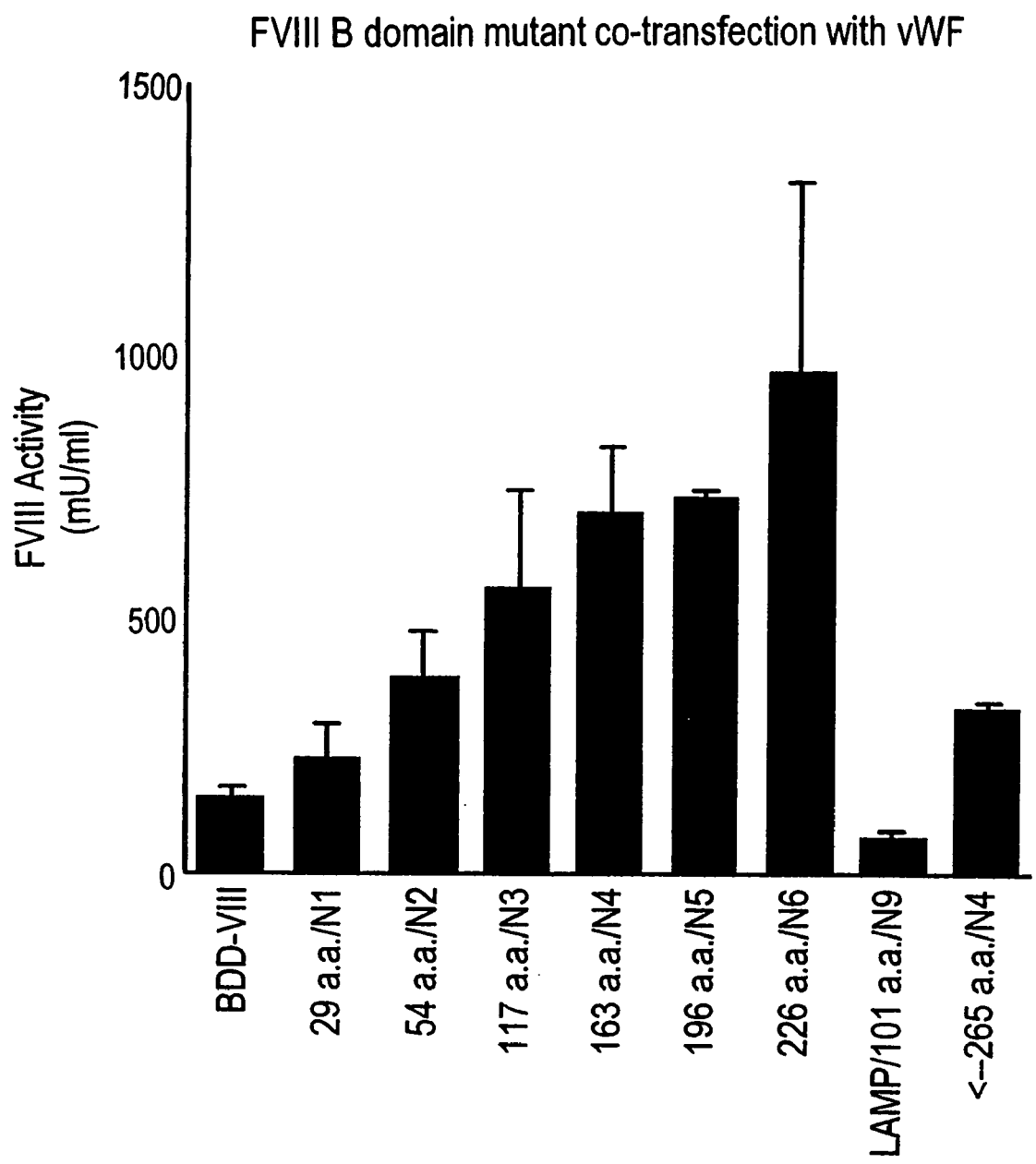
FIG. 29 is a graph depicting the relative efficiency of secretion of FVIII B domain variants.

Maximal secretion was observed with a 226 amino acid B domain and 6 N-linked oligosaccharides (FIG. 29). A non-native B domain did not facilitate increased secretion despite dense N-linked glycosylations (LAMP) (FIG. 29).

B domain mediated interaction. Without being limited by theory, it is believed that the B domain, by virtue of its rich oligosaccharide content, mediates interaction with ERGIC-53 to facilitate its ER to Golgi transport. BDD-FVIII has been used in most hemophilia A gene therapy strategies as the full-length cDNA is too large for most viral vectors. These results suggest that addition of N-linked glycosylation sites can improve the secretion of BDD-FVIII up to 10-fold and may increase FVIII expression in vivo.

Structure and function of B Domain. Further experimentation was performed to evaluate the impact of density and/or orientation of the oligosaccharides. Two densely glycosylated protein segments derived from the unrelated glycoprotein LAMP-1 (containing either 5 or 9 N-linked oligosaccharides) were substituted for B domain sequence, but did not improve secretion compared to BDD-FVIII. This suggests that the density and/or orientation of the oligosaccharides may be important.

EXAMPLE 10

Characterization and Analysis of FVIII B-domain Mutants

Experimental Procedures

A FVIII B-domain mutant (also referred to herein as the "90/80/b226N6 variant" or "b226N6 variant") includes the Phe309Ser mutant and the b226N6 B-domain variant. In particular, in one embodiment, a FVIII B-domain mutant comprises 226 amino acid B-domain with 6 consensus sites for N-linked glycosylation.

Results

The FVIII B-domain mutant achieves maximal expression in COS cell and CHO cell transient expression. The secreted protein yields FVIII with high specific activity and is secreted as a single chain without intracellular processing.

The results demonstrated that the hybrid FVIII molecule yields a 15-fold greater expression as compared to BDD-FVIII, while the Phe309Ser mutation alone shows a 6-fold increase compared to BDD-FVIII and the b226N6 mutation alone shows an 8-fold increase in expression compared to BDD-FVIII.

Figure 30:
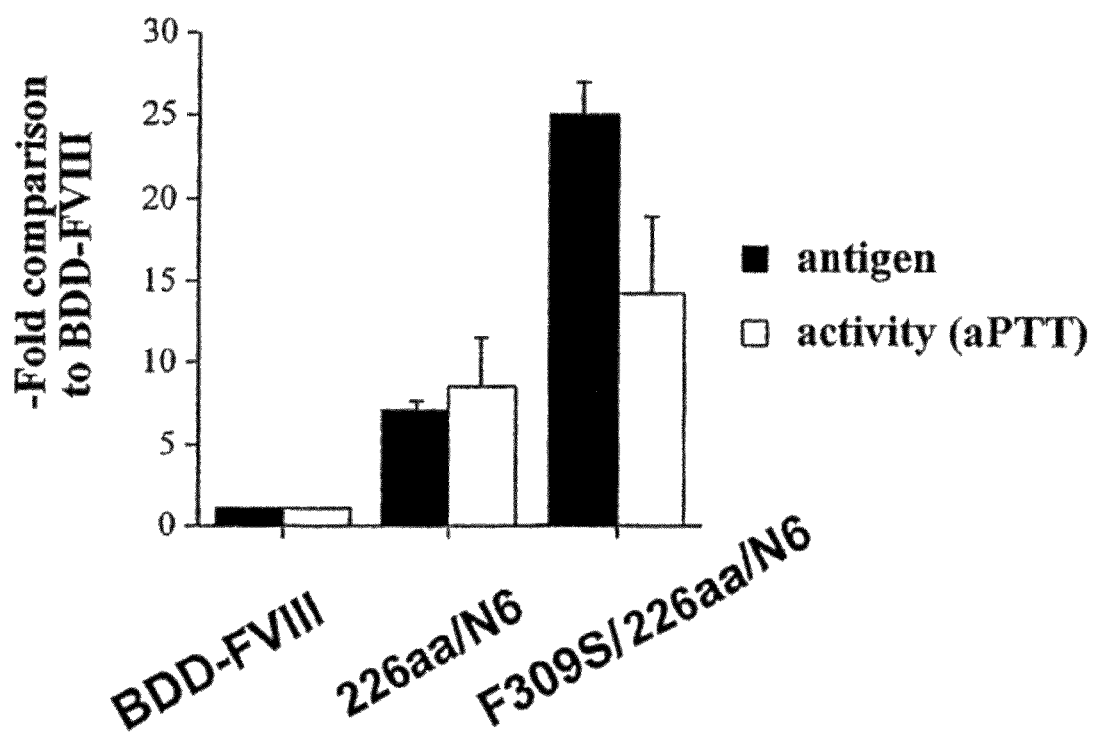
FIG. 30 is a graph that depicts the relative efficiency of secretion of the combined F309S and B domain variant 226aa/N6 ("F309/226aa/N6 variant")

The results further demonstrated that the secretion efficiency of a FVIII construct containing a mutant B domain 226aa/N6 is further enhanced with the point mutation F309S (FIG. 30).

EXAMPLE 11

Expression of Bioengineered FVIII in vivo
Experimental Procedures

A FVIII knockout mouse model of hemophilia A was utilized to analyze the in vivo expression of the FVIII molecules of the present invention.

Figure 33:
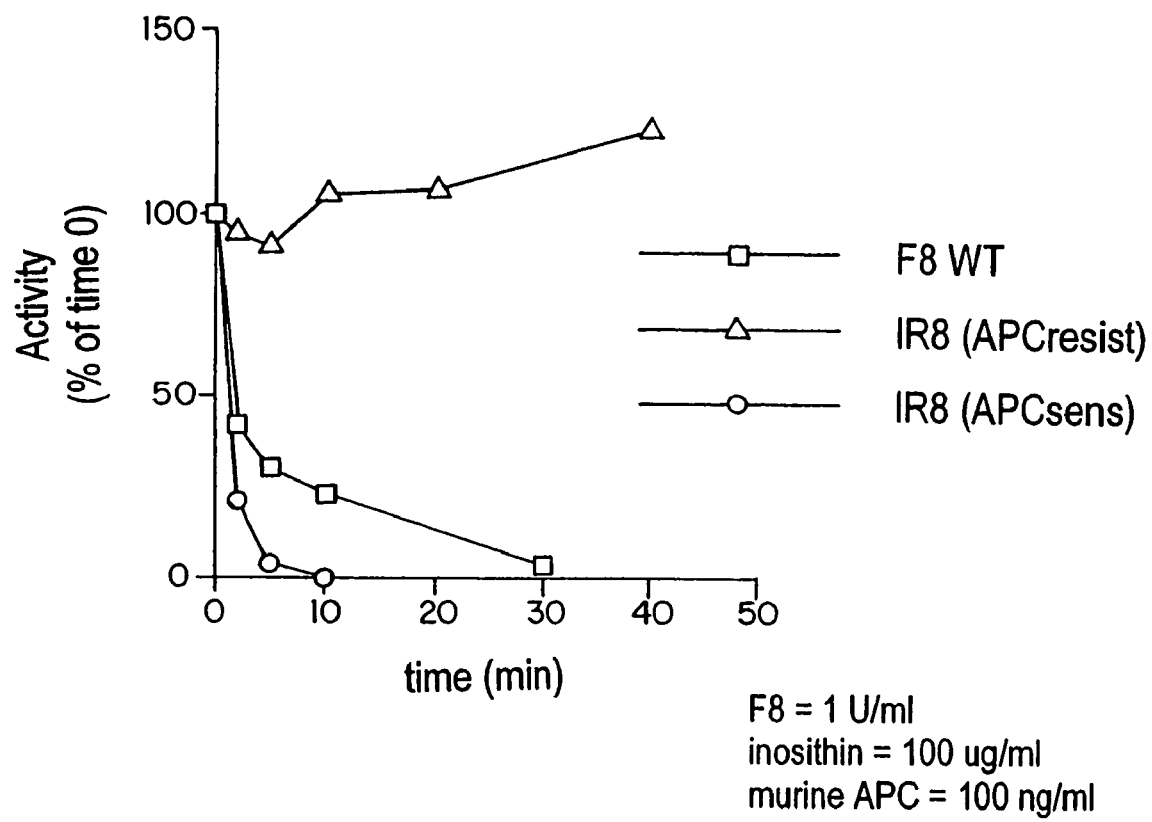
FIG. 33 is a graph that depicts FVIII activity over time in mice.
Figure 34:
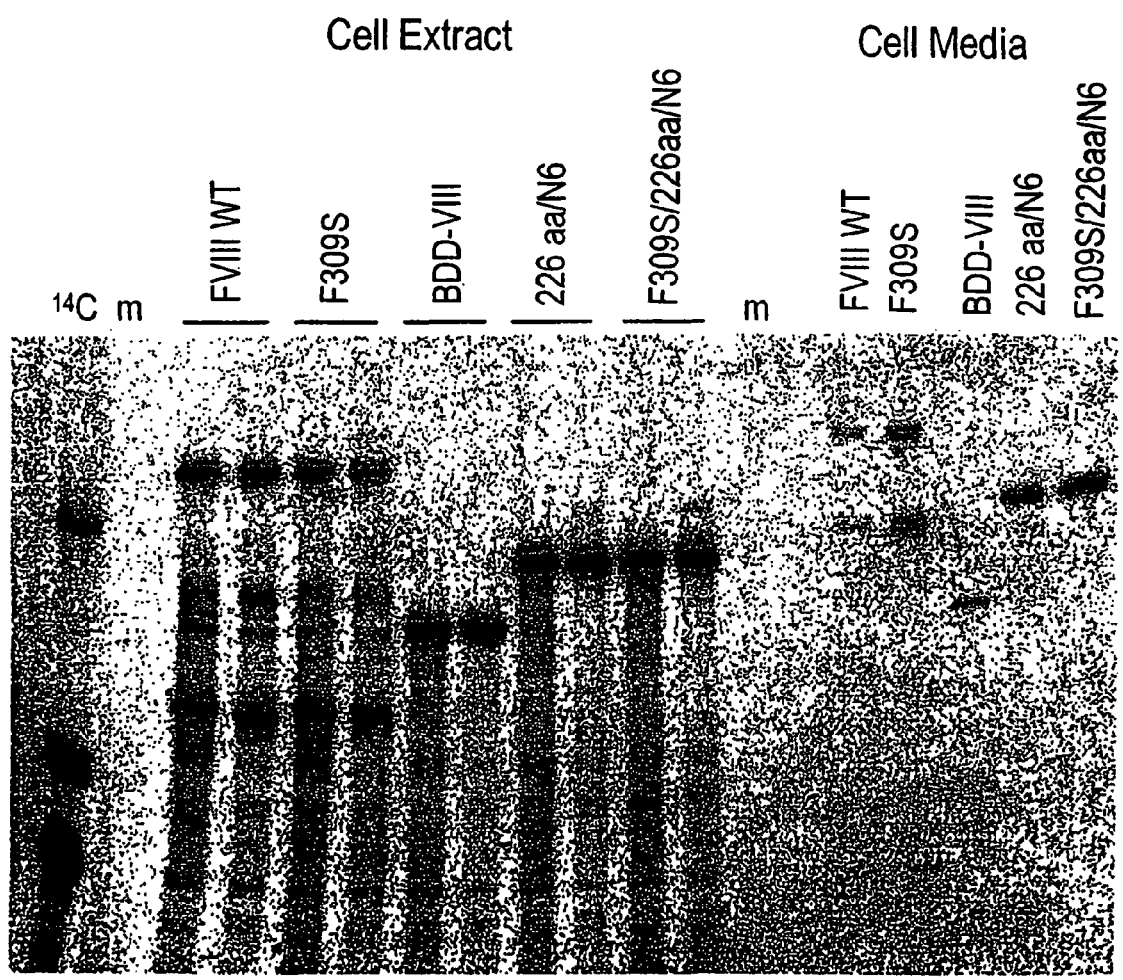
FIG. 34 depicts the presence of the FVIII B domain variants in cell extract and cell media.

Methods. Plasmid DNA (100 µg) was diluted in 2.5 ml of lactated Ringer's and infused over 10 seconds into the tail vein. Orbital blood collection was performed at 24 and 48 hours and FVIII secretion analyzed by a human FVIII-specific ELISA. The FVIII anitigen and activity were measured in blood (FIGS. 31 and 33). FIG. 34 confirms the presence of 226aa/N6 and F309S/226aa/N6 in the cell media.

Results

Figure 32:
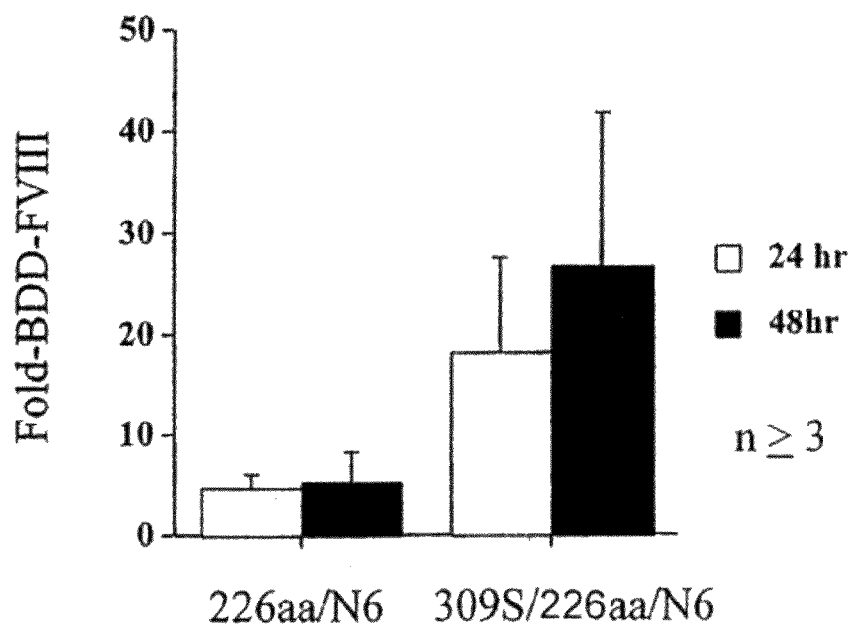
FIG. 32 is a graph that depicts in vivo expression of the FVIII B domain variants in FVIII knockout mice.

FIGS. 31 and 32 indicate increased expression of FVIII B domain variants in hemophilia A mice following hydrodynamic tail vein injection of the F309S/226aa/N6 construct. In particular, the 309S/226aa/N6 variant showed increased expression at 48 hours as compared to the 226aa/N6 variant (FIG. 32). The data derived indicated that the average BDD-FVIII expression was 123 ng/ml after 24 hours and 124 ng/ml after 48 hours (see FIG. 32).

EXAMPLE 12

Pharmaceutical Compositions and Use

Pharmaceutical Composition

The FVIII proteins of the present invention can be formulated into pharmaceutically acceptable compositions with parenterally acceptable vehicles and excipients in accordance with procedures known in the art. The pharmaceutical compositions of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g. in sealed ampoules or vials.

Such pharmaceutical compositions may also contain pharmaceutically acceptable carriers, diluents, fillers, salts, buffers, stabilizers, and/or other materials well known in the art. The term "pharmaceutically acceptable" means a non-toxic material that does not interfere with the effectiveness of the biological activity of the active ingredient(s). The characteristics of the carrier or other material will depend on the route of administration.

The amount of FVIII protein in the pharmaceutical composition of the present invention will depend upon the nature and severity of the condition being treated, and on the nature of the prior treatments which the patient has undergone. Ultimately, the attending physician will decide the amount of protein with which to treat each individual patient. The duration of intravenous therapy similarly will vary, depending on the severity of the disease being treated and the condition and potential idiosyncratic response of each individual patient.

In addition, the nucleotide sequences encoding the FVIII proteins of the present invention may be associated with a gene therapy delivery system in accordance with procedures known in the art. Such delivery systems include, without limitation, adenoviral, retroviral and adeno-associated viral vectors, as well as liposomes and DNA-protein complexes. The sequences of the present invention are contained in or operatively-linked to such delivery systems in a manner which allows for transcription, e.g., through the use of sufficient regulatory elements. It will be appreciated that a variety of strategies and methodology for creating such gene therapy delivery systems are well known to those skilled in the art.

Methods of Use

Pharmaceutical compositions containing the proteins of the present invention may be used to treat patients suffering from hemophilia caused by deficiency of FVIII.

In practicing the method of treatment of this invention, a therapeutically effective amount of FVIII protein is administered to a mammal having a hemophiliac condition caused by FVIII deficiency. The term "therapeutically effective amount" means the total amount of each active component of the method or composition that is sufficient to show a meaningful patient benefit, i.e. cessation of bleeding.

Administration of the proteins of the present invention can be carried out in a variety of conventional ways. Intravenous administration to the patient is preferred. When administered by intravenous injection, the proteins of the invention will be in the form of pyrogen-free, parenterally acceptable aqueous solutions. A preferred pharmaceutical composition for intravenous injection should contain, in addition to the proteins, an isotonic vehicle such as sodium chloride injection, Ringer's injection, dextrose injection, dextrose and sodium chloride injection, lactated Ringer's injection, or other vehicles as known in the art. The pharmaceutical composition according to the present invention may also contain stabilizers, preservatives, buffers, anti-oxidants, or other additives known to those of skill in the art.

For cutaneous or subcutaneous injection, the proteins of the present invention will be in the form of pyrogen-free, parenterally acceptable aqueous solutions. The preparation of such parenterally acceptable protein solutions, having due regard to pH, isotonicity, stability, and the like, is within the skill in the art.

As with the pharmaceutical compositions containing the proteins of the present invention, gene therapy delivery systems or vehicles containing nucleotide sequences of the present invention may also be used to treat patients suffering form hemophilia caused by deficiency of FVIII. A therapeutically effective amount of such gene therapy delivery vehicles is administered to a mammal having a hemophiliac condition caused by FVIII deficiency. It will be appreciated that administration of the vehicles of the present invention will be by procedures well established in the pharmaceutical arts, e.g. by direct delivery to the target tissue or site, intranasally, intravenously, intramuscularly, subcutaneously, intradermally and through oral administration, either alone or in combination. It will also be appreciated that formulations suitable for administration of the gene therapy delivery vehicles are known in the art and include aqueous and non-aqueous isotonic sterile injection solutions and aqueous and non-aqueous sterile suspensions.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

mains and a mutation at Arg740, wherein the spacer is of a sufficient length that upon thrombin activation, the FVIII protein becomes a heterodimer comprising an A1-domain and an A2-spacer-A3-C1-C2 chain, and wherein the mutation consists of a substitution of Arg at position 740 with Ala, and wherein the A2-domain remains covalently associated with the A3-, C1-, and C2-domains through the spacer.

2. A pharmaceutical composition comprising an effective amount of the protein of claim 1 in admixture with a parenterally acceptable vehicle or excipient.

3. The protein of claim 1, wherein the amino acid sequence spacer is at least 54 amino acid residues in length.

4. The protein of claim 1, wherein the amino acid sequence spacer consists of amino acid residues 741 to 794 of wild-type FVIII, wherein the amino acid residue at position 794 is selected from the group consisting of threonine and leucine.

We claim:

1. A FVIII protein comprising the A1-, A2-, A3-, C1- and C2-domains of human Factor VIII, said FVIII protein having an amino acid sequence spacer between the A2- and A3-do- 5. The protein of claim 4, wherein the amino acid residue at position 794 is threonine.

* * * * *

```
SEQUENCE LISTING

<160> NUMBER OF SEQ ID NOS: 2

<210> SEQ ID NO 1
<211> LENGTH: 162
<212> TYPE: DNA
<213> ORGANISM: Homo sapies
<220> FEATURE:
<221> NAME/KEY: CDS
<222> LOCATION: (1)...(162)

<400> SEQUENCE: 1 agc ttc tcc cag aat tca aga cac cct agc act agg caa aag caa ttt        48
Ser Phe Ser Gln Asn Ser Arg His Pro Ser Thr Arg Gln Lys Gln Phe
 1               5                  10                  15 aat gcc acc aca att cca gaa aat gac ata gag aag act gac cct tgg        96
Asn Ala Thr Thr Ile Pro Glu Asn Asp Ile Glu Lys Thr Asp Pro Trp
             20                  25                  30 ttt gca cac aga aca cct atg cct aaa ata caa aat gtc tcc tct agt       144
Phe Ala His Arg Thr Pro Met Pro Lys Ile Gln Asn Val Ser Ser Ser
         35                  40                  45 gat ttg ttg atg ctc ttg                                               162
Asp Leu Leu Met Leu Leu
     50

<210> SEQ ID NO 2
<211> LENGTH: 54
<212> TYPE: PRT
<213> ORGANISM: Homo sapies

<400> SEQUENCE: 2

Ser Phe Ser Gln Asn Ser Arg His Pro Ser Thr Arg Gln Lys Gln Phe
 1               5                  10                  15

Asn Ala Thr Thr Ile Pro Glu Asn Asp Ile Glu Lys Thr Asp Pro Trp
             20                  25                  30

Phe Ala His Arg Thr Pro Met Pro Lys Ile Gln Asn Val Ser Ser Ser
         35                  40                  45

Asp Leu Leu Met Leu Leu
     50
```